United States Patent
Yost et al.

(10) Patent No.: US 11,752,203 B2
(45) Date of Patent: *Sep. 12, 2023

(54) METHODS FOR TREATMENT OF AND PROPHYLAXIS AGAINST INFLAMMATORY DISORDERS

(71) Applicant: University of Utah Research Foundation, Salt Lake City, UT (US)

(72) Inventors: Christian Con Yost, North Salt Lake, UT (US); Guy A. Zimmerman, Salt Lake City, UT (US); Andrew S. Weyrich, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,221

(22) Filed: Apr. 6, 2020

(65) Prior Publication Data

US 2020/0276284 A1    Sep. 3, 2020

Related U.S. Application Data

(60) Continuation of application No. 16/255,545, filed on Jan. 23, 2019, now Pat. No. 10,646,556, which is a continuation of application No. 15/441,982, filed on Feb. 24, 2017, now Pat. No. 10,232,023, which is a division of application No. 14/904,048, filed on Jan. 8, 2016, now abandoned.

(60) Provisional application No. 61/843,618, filed on Jul. 8, 2013.

(51) Int. Cl.
| | |
|---|---|
| A61K 38/00 | (2006.01) |
| A61K 38/57 | (2006.01) |
| A61K 38/17 | (2006.01) |
| C07K 14/47 | (2006.01) |

(52) U.S. Cl.
CPC .......... A61K 38/57 (2013.01); A61K 38/1709 (2013.01); C07K 14/4703 (2013.01); *A61K 38/00* (2013.01); *Y02A 50/30* (2018.01)

(58) Field of Classification Search
CPC .......................... A61K 38/1709; A61K 38/37
See application file for complete search history.

(56) References Cited

U.S. PATENT DOCUMENTS

| | | | |
|---|---|---|---|
| 5,516,643 A | 5/1996 | Cercek et al. | |
| 8,975,224 B2 | 3/2015 | Mogelsvang et al. | |
| 9,951,104 B2 | 4/2018 | Mogelsvang et al. | |
| 10,214,562 B2 | 2/2019 | Mogelsvang et al. | |
| 10,899,797 B2 | 1/2021 | Mogelsvang et al. | |
| 11,020,462 B2 | 6/2021 | Gelber | |
| 2003/0007959 A1 | 1/2003 | Lezdey et al. | |
| 2007/0218535 A1 | 9/2007 | Lin et al. | |
| 2010/0210528 A1 | 8/2010 | Shapiro | |
| 2016/0194365 A1 | 7/2016 | Yost et al. | |
| 2021/0188912 A1 | 6/2021 | Mogelsvang et al. | |
| 2021/0369822 A1 | 12/2021 | Gelber | |
| 2022/0265761 A1 | 8/2022 | Austin et al. | |

FOREIGN PATENT DOCUMENTS

| | | | |
|---|---|---|---|
| EP | 14822757.2 | 7/2014 | |
| WO | WO-2005/112989 A1 | 12/2005 | |
| WO | WO-2012/166611 A2 | 12/2012 | |
| WO | WO-2012/178102 A2 | 12/2012 | |
| WO | WO-2012178102 A2 * | 12/2012 | ............. A61P 19/06 |
| WO | WO2013106273 | 7/2013 | |
| WO | PCT/US2014/045597 | 7/2014 | |
| WO | WO2014197524 | 12/2014 | |
| WO | WO2017040287 | 3/2017 | |
| WO | WO2022010939 | 3/2017 | |

OTHER PUBLICATIONS

Delgado, C. et al., The Uses and Properties of PEG-Linked Proteins. Crit Rev Ther Drug Carrier Syst. 1992; 9(3-4):249-304.
Ellis, T.N. et al., Interferon-? Activation of Polymorphonuclear Neutrophil Function. Immunology. 2004; 112(1):2-12.
Hamulyák, K. et al., Reevaluation of Some Properties of Fibrinogen, Purified from Cord Blood of Normal Newborns. Thromb Res. 1983; 32(3):301-10.
Simpson, R.J. et al., Proteomics-Driven Cancer Biomarker Discovery: Looking to the Future. Curr Opin Chern Biol. 2008; 12(1):72-7.
Ward, A.M. et al., Reference Ranges for Serum a1 Antitrypsin. Arch Dis Child. 1985; 60(3):261-2.
Wermuth, C.G. et al., Glossary of Terms Used in Medicinal Chemistry (IUPAC Recommendations 1998). Pure App Chem. 1998; 70(5):1129-1143.
Yost, C.C. et al., Impaired Neutrophil Extracellular Trap (NET) Formation: a Novel Innate Immune Deficiency of Human Neonates. Blood. 2009; 133(25):6419-27.
Supplementary European Search Report dated Mar. 21, 2017 by the European Patent Office for Patent Application No. 14822757.2, which was filed on Jul. 7, 2014 and published as EP 3019188 on May 18, 2016 (Inventor—Yost et al.; Applicant—University of Utah Research Foundation; (12 pages).

(Continued)

*Primary Examiner* — Jeanette M Lieb
(74) *Attorney, Agent, or Firm* — BALLARD SPAHR LLP

(57) ABSTRACT

An isolated and purified peptide, neonatal NET-inhibitory Factor (nNIF), is disclosed. Methods for treatment of and prophylaxis against inflammatory disorders are also disclosed, including methods of treatment of and prophylaxis against inflammatory disorders comprising administering NET-inhibitory peptides (NIPs), which may be a nNIF, a pharmaceutically acceptable salt of a nNIF, a nNIF analog, a pharmaceutically acceptable salt of a nNIF analog, a nNIF-Related Peptide (nNRP), including the nNRP, Cancer-Associated SCM-Recognition, Immune Defense Suppression, and Serine Protease Protection Peptide (CRISPP), a pharmaceutically acceptable salt of a nNRP, a nNRP analog, or a pharmaceutically acceptable salt of a nNRP analog, to an individual.

21 Claims, 26 Drawing Sheets

Specification includes a Sequence Listing.

(56) References Cited

OTHER PUBLICATIONS

Communication Pursuant to Article 94(3) EPC dated Mar. 11, 2019 by the European Patent Office for Patent Application No. 14822757.2, which was filed on Jul. 7, 2014 and published as EP 3019188 on May 18, 2016 (Inventor—Yost et al.; Applicant—University of Utah Research Foundation; (6 pages).
International Search Report and Written Opinion dated Dec. 5, 2014 by the International Searching Authority for Patent Application No. PCT/US2014/045597, which was filed on Jul. 7, 2014 and published as WO 2015/006228 on Jan. 15, 2015 (Inventor—Yost et al.; Applicant—University of Utah Research Foundation; (14 pages).
International Preliminary Report on Patentability dated Jan. 12, 2016 by the International Searching Authority for Patent Application No. PCT/US2014/045597, which was filed on Jul. 7, 2014 and published as WO 2015/006228 on Jan. 15, 2015 (Inventor—Yost et al.; Applicant—University of Utah Research Foundation; (12 pages).
Non-Final Office Action dated Nov. 1, 2016 by the U.S. Patent Office for U.S. Appl. No. 14/904,048, filed Jan. 8, 2016 and published as US 2016/0194365 on Jul. 7, 2016 (Inventor—Yost et al.; Applicant—University of Utah Research Foundation; (20 pages).
Non-Final Office Action dated Mar. 21, 2018 by the U.S. Patent Office for U.S. Appl. No. 15/441,982, filed Feb. 24, 2017 and issued as U.S. Pat. No. 10,232,023 on Mar. 19, 2019 (Inventor—Yost et al.; Applicant—University of Utah Research Foundation; (10 pages).
Notice of Allowance dated Oct. 24, 2018 by the U.S. Patent Office for U.S. Appl. No. 15/441,982, filed Feb. 24, 2017 and issued as U.S. Pat. No. 10,232,023 on Mar. 19, 2019 (Inventor—Yost et al.; Applicant—University of Utah Research Foundation; (6 pages).
Non-Final Office Action dated Jul. 10, 2019 by the U.S. Patent Office for U.S. Appl. No. 16/255,545, filed Jan. 23, 2019 and published as US 2019/0307865 on Oct. 10, 2019 (Inventor—Yost et al.; Applicant—University of Utah Research Foundation; (7 pages).
Notice of Allowance dated Jan. 8, 2020 by the U.S. Patent Office for U.S. Appl. No. 16/255,545, filed Jan. 23, 2019 and issued as U.S. Pat. No. 10,646,556 on May 12, 2020 (Inventor—Yost et al.; Applicant—University of Utah Research Foundation; (5 pages).
U.S. Appl. No. 61/843,618, filed Jul. 8, 2918, Christian Con Yost (Univ. Utah Res. Found.).
U.S. Appl. No. 14/904,048 (2016/0194365), filed Jan. 8, 2016 (Jul. 7, 2016), Christian Con Yost (Univ. Utah Res. Found.).
U.S. Appl. No. 15/441,982 (U.S. Pat. No. 10,232,023), filed Feb. 24, 2017 (Mar. 19, 2018), Christian Con Yost (Univ. Uath Res. Found.).
U.S. Appl. No. 16/255,545 (U.S. Pat. No. 10,646,556), filed Jan. 23, 2019 (May 12, 2020), Christian Con Yost (Univ. Utah Res. Found.).

* cited by examiner

| Proteins Identified (Mascot Search Result: NCBI Human) | Mass (kD) | Protein Score |
|---|---|---|
| 1. Intact A1AT | 44.3 | 2122 |
| 2. Angiotensinogen | 53.1 | 901 |
| 3. Serum albumin | 69.3 | 822 |
| 4. Alpha-2-macroglobulin precursor | 163.2 | 301 |
| 5. Alpha-1-antichymotrypsin | 48.6 | 195 |
| 6. CRISPP/nNIF | 4.0 | 142 |

*FIG. 4A*

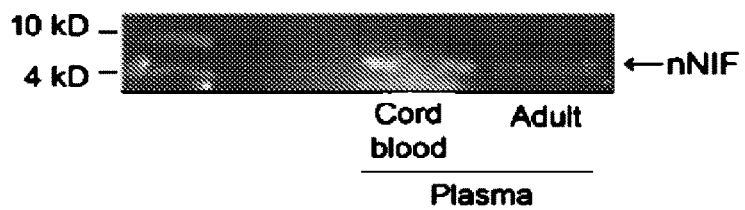

*FIG. 4B*

| A1ATm[358] | NH$_2$- pmsippevkfnkpfvflmieqntksplfmgkvvnptqk -COOH |
|---|---|
| nNIF | NH$_2$- _____kfnkpfvflmieqntksplfmgkvvnptq_ -COOH |
| Synthetic CRISPP | NH$_2$- _m_ippevkfnkpfvflmidqntkvplfmgk_____ -COOH |

*FIG. 4C*

CLD+

Preterm Lamb Control     Preterm Lamb Mechanical Ventilation

METHODS FOR TREATMENT OF AND PROPHYLAXIS AGAINST INFLAMMATORY DISORDERS

CROSS REFERENCE TO RELATED APPLICATIONS

This application is a continuation of U.S. application Ser. No. 16/255,545, filed on Jan. 23, 2019, which is a continuation of U.S. application Ser. No. 15/441,982, filed Feb. 24, 2017, which is a divisional of U.S. application Ser. No. 14/904,048, filed Jan. 8, 2016, which is a National Stage of International Application No. PCT?US2014/45597, filed Jul. 7, 2014, and which claims priority to U.S. Provisional Application No. 61/843,618, filed on Jul. 8, 2013, each of which are herein incorporated by reference in their entirety.

REFERENCE TO SEQUENCE LISTING

The Sequence Listing submitted Apr. 6, 2020 as a text file named "21101_0371U5_Sequence_Listing.txt," created on Apr. 6, 2020, and having a size of 2,497 bytes is hereby incorporated by reference pursuant to 37 C.F.R. § 1.52(e)(5).

TECHNICAL FIELD

The present disclosure is directed to methods for treatment of and prophylaxis against inflammatory disorders.

BACKGROUND

Neutrophil extracellular traps (NETs) are extracellular lattices of decondensed chromatin decorated with antimicrobial proteins extruded by polymorphonuclear leukocytes (PMNs, neutrophils) to trap and kill microbes. Although NETs aid in trapping bacteria and other pathogens, their presence also leads to inflammatory tissue damage. Indeed, NET formation contributes to the pathology of several inflammatory disorders including acute lung injury resulting from influenza or blood transfusions, sepsis, small vessel vasculitis, systemic inflammatory response syndrome (SIRS), and chronic autoimmune diseases like systemic lupus erythematosus. Furthermore, NET formation and, in particular, the release of NET-associated histones into the extravascular space directly induces both epithelial and endothelial cell death in culture.

An active cell death process distinct from necrosis and apoptosis, frequently termed "NETosis," leads to formation of three dimensional lattices studded with granule enzymes and host defense peptides that bind to nuclear chromatin before extrusion from the neutrophil. Histones, which have antimicrobial activities, are also abundant in NETs. NET formation is conserved in many species.

Deficient NET formation is a mechanism of immunodeficiency and impaired human host defense. A variety of pathogens induce NET formation. In addition to *Escherichia coli, Staphylococcus, Streptococcus, Yersinia*, and other gram positive and negative bacteria, fungi, parasites, and viruses trigger generation of NETs by human PMNs. Lipopolysaccharides (LPS) also induce NETosis, suggesting that microbial toxins may broadly have this activity. Endogenous host mediators, including interleukin-8 (IL-8), platelet activating factor (PAF), and complement factor C5a induce NET formation directly or after "priming" by other mediators. LPS stimulated mouse platelets, activated human platelets, and platelets in a murine model of transfusion-related acute lung injury (TRALI) that involves LPS priming also trigger NET formation. H1N1-infected alveolar epithelial cells induce NET formation by murine neutrophils in vitro. Thus, multiple interactions between neutrophils and microbes, host cells, and/or host mediators signal NETosis and NET formation.

NETs are also major biologic instruments of extravascular microbial containment and killing in vitro and in vivo, thus limiting the spread of pathogens. Certain pathogens, however, express endonucleases that cleave the DNA lattice or inhibitors that block antimicrobial peptides; these mechanisms act as virulence factors that limit killing and provide mechanisms for bacterial escape.

Failed NET formation appears to be a previously-unrecognized innate immune deficit that results in severe infections. Patients with chronic granulomatous disease (CGD), who are deficient in reactive oxygen species (ROS) generation and acquire recurrent, often life threatening bacterial and fungal infections, also demonstrate a defect in NET formation. Gene therapy for this immune deficiency can restore NET formation and control refractory pulmonary aspergillosis in patients with CGD. This suggests that NETs can also demonstrate protective functions in cystic fibrosis and pneumonia.

While the intracellular signaling pathways that regulate NET formation by PMNs remain largely unknown, ROS generation is considered a key event. Studies in human HL-60 myeloid leukocytes and genetically-altered mice indicate that activity of peptidylarginine deiminase 4 (PAD 4), an enzyme responsible for chromatin decondensation, is also required.

Additionally, NET formation may require enzymatic activity of neutrophil elastase (NE) to initiate degradation of core histones leading to chromatin decondensation prior to plasma membrane rupture. Alpha 1 anti-trypsin (A1AT) is a serine protease inhibitor that inactivates NE in plasma; it is, however, not expressed by human PMNs. A related serine protease inhibitor, serpin B1, which is expressed as a cytoplasmic protein by human PMNs, has been shown to restrict NET formation by mouse and human PMNs. Furthermore, treatment with recombinant serpin B1 inhibits NET formation in human PMNs stimulated with phorbol 12-myristate acetate (PMA), a robust inducer of NET formation in vitro. Recombinant A1AT, however, does not inhibit NET formation. Inhibition of specific serine proteases such as NE may effectively inhibit NET formation by human PMNs.

Although NET formation is a critical innate antimicrobial function of PMNs, there is now clear evidence that it is a mechanism of inflammatory tissue injury and thrombosis if inappropriately triggered and/or dysregulated. See Saffarzadeh and Preissner, Curr Opin Hematol, 2013, 20: 3-9; and Brinkmann and Zychlinsky, J Cell Biol, 2012, 198(5): 773-783. NETs mediate inflammatory damage in multiple models of sterile and infectious challenge. For example, NET formation may be a key mechanism in the systemic vasculopathy that is central to the pathogenesis of the acute, pro-inflammatory phase of sepsis. Bacteria including Staphylococci and *E. coli* are major causes of severe sepsis, alone or as polymicrobial infections, depending on the populations studied.

Experiments utilizing human endothelial cells (EC) and neutrophils in vitro, and an in vivo model of endotoxemia in which mice were challenged with LPS, indicate that NETs cause endothelial and liver damage, potentially mediated by neutrophil proteases associated with NETs. NE and other granule enzymes from neutrophils can potently injure endothelium and many extravascular cell types. EC activation, as occurs in sepsis, can enhance NET generation. In addition to granule enzymes, histones associated with NETs are previously-unrecognized agonists for endothelial injury in sepsis, based on experimental models and human samples.

There is also evidence that NETs and NET components are potent procoagulants, and that NET components induce thrombosis—a central pathogenetic feature of sepsis. NET components modify fibrin stability and fibrinolysis. Thus, while formation of NETs may be critical for bacterial capture and containment in the early phases of bacteremia and sepsis based on murine models, observations to date indicate that NET formation also causes damage to the host (for example, in acute septic syndromes).

Activated vascular endothelium may induce NET formation by human PMNs and lead to endothelial cell damage in vitro. Also, cellular damage may occur when human endothelial cells are incubated with activated platelets and PMNs, leading to NET formation, and liver injury may occur in vivo following NET formation. Finally, placentas from mothers with severe pre-eclampsia, a syndrome of pregnancy commonly leading to premature infant delivery, show exuberant NET formation. Thus, while essential in preventing severe infections, inappropriate NET formation appears to also be a mechanism of inflammatory vascular and tissue injury.

Inflammatory and infectious pulmonary syndromes provide another example of NET-mediated tissue injury. NETs form and contribute to vascular and alveolar dysfunction in animal models of acute lung injury and adult respiratory distress syndrome (ARDS). ARDS is a major complication of human systemic and pulmonary infection and inflammation. NETs are associated with acute lung injury in models of influenza-induced pneumonitis, a common and lethal infectious trigger for ARDS. In vitro studies indicate that NET histones may be critical mediators of alveolar endothelial and epithelial cell death.

In addition to sepsis and pulmonary injury, vasculitic syndromes are yet another example in which NETs play pathogenetic roles. As in sepsis, NETs may mediate both vascular inflammation and thrombosis in vasculitis. A variety of inflammatory stimuli and infectious agents can cause vasculitis.

Dysregulated inflammation has also been found to contribute to the pathogenesis of all the major complications of prematurity: necrotizing enterocolitis (NEC), respiratory distress syndrome (RDS), pneumonia, bronchopulmonary dysplasia (BPD), neonatal chronic lung disease (CLD), neurodevelopmental delay, retinopathy of prematurity (ROP), and sepsis. Neonatal CLD causes significant morbidity and mortality in the U.S. CLD is a complication of preterm birth that results from prolonged mechanical ventilation required for chronic respiratory failure. It occurs in up to 70% of mechanically ventilated extremely low birth weight infants (ELBW) with respiratory distress. While surfactant therapy and pre- or postnatal steroids have decreased the severity of CLD, this significant morbidity associated with preterm birth remains common in at-risk infants, with about 8,000 to 10,000 new cases occurring annually in the U.S. The mortality rate due to CLD in ELBW infants remains high from 15-60%. Furthermore, CLD remains the most common cause of long-term hospitalization in neonates and is also associated with developmental delay.

Additional current evidence strongly supports the conclusion that NETs are involved in tissue damage and thrombosis in a variety of inflammatory syndromes. Consequently, a few therapeutic strategies to blunt or interrupt NET formation or the activities of NET components have been investigated. All such strategies identified to date have major limitations, however. Global inhibition of neutrophil function and/or specific inhibitors of oxygen radical generation or key molecular checkpoints such as HIF-1α depress other PMN functions, including migration, phagocytosis, and/or intracellular microbial killing, causing parallel potential for microbial evasion and iatrogenic infections.

Disruption of NETs with DNases, potentially together with inhibition of NET-associated histones and enzymes as a combination strategy, represents a therapeutic approach based on experimental models. Nevertheless, more than twenty different NET-associated proteins have been identified, making this impractical. Furthermore, enzymatic disruption of NETs as an intervention may lead to dissemination of microbes, depending on its timing. Pharmacologic disruption of NETs in the vasculature also has the potential to spread histones and toxic neutrophil enzymes to other vascular beds, initiating or amplifying multiple organ injury. Finally, heparins inhibit NET formation under some conditions, but have bleeding as a well-known complication.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4A is a list of nNIF candidate proteins, expected molecular mass, and protein score.

FIG. 4B is a western blot using a polyclonal antibody against the carboxy-terminus of A1AT comparing nNIF (≈6 kD) expression in cord blood and adult plasma.

FIG. 4C is a comparison of the mass spectroscopy obtained sequences of nNIF, CRISPP, and the A1ATm$^{358}$ cleavage fragment of full length A1AT.

DETAILED DESCRIPTION

Figure 1A:
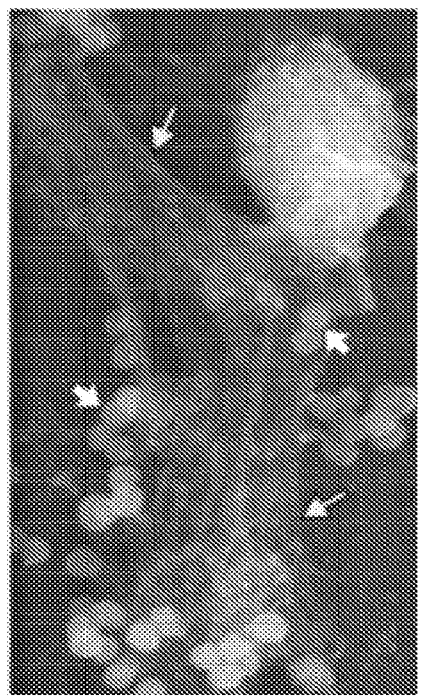
FIG. 1A is an image of adult human PMNs extruding NETs (thin arrows) to trap and kill bacteria, S. aureus (wide arrows).
Figure 1B:
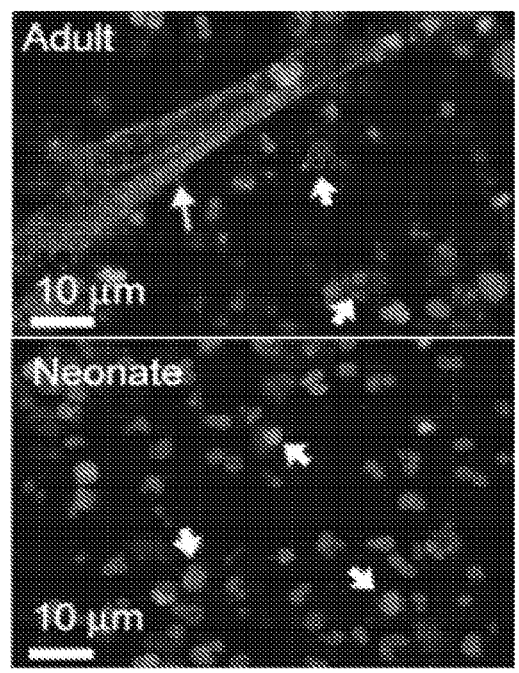
FIG. 1B compares the decoration of NETs (thin arrow) with neutrophil elastase (NE) (thick arrow) formed by adult human PMNs to neonatal PMNs which do express NE but do not form NETs.

This disclosure is related to methods for treatment of and prophylaxis against inflammatory disorders. It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Each and every patent, report, and other reference recited herein is incorporated by reference in its entirety.

DEFINITIONS

A "NET-Inhibitory Peptide (NIP)" is an anti-inflammatory agent that inhibits neutrophil extracellular trap (NET) formation. Examples of NIPs include, but are not limited to: a neonatal NET-Inhibitory Factor (nNIF); a pharmaceutically acceptable salt of a nNIF; an analog of a naturally occurring form of nNIF, which nNIF analog inhibits NETosis and/or the formation of NETs and is structurally altered, relative to a given human nNIF, by at least one amino acid addition, deletion, substitution, or by incorporation of one or more amino acids with a blocking group; a pharmaceutically acceptable salt of a nNIF analog; a nNIF-Related Peptide (nNRP); a pharmaceutically acceptable salt of a nNRP; a nNRP analog; or a pharmaceutically acceptable salt of a nNRP analog.

A "neonatal Neutrophil Inhibitory Factor peptide" or "nNIF peptide" is defined herein as a nNIF which is naturally occurring in mammals.

A "neonatal NIF-related peptide" or "nNRP" is defined herein as a Cancer-Associated SCM-Recognition, Immune Defense Suppression, and Serine Protease Protection Peptide (CRISPP) which is naturally occurring in humans; A1ATm$^{358}$, which has been shown to inhibit NET formation; and other nNIF-related peptides; and as analogs of naturally occurring forms of nNRPs that inhibit NETosis and/or the formation of NETs and are structurally altered, relative to a given human nNRP, by at least one amino acid addition, deletion, substitution, or by incorporation of one or more amino acids with a blocking group.

"Inflammatory disorders" are defined herein as disorders characterized by pathological inflammation. Inflammatory disorders include, but are not limited to, conditions associated with infection, autoimmunity, and allergy. Inflammatory disorders as defined herein may include, but are not limited to, acute respiratory distress syndrome (ARDS), bronchopulmonary dysplasia (BPD), chronic obstructive pulmonary disease (COPD), cystic fibrosis, inflammation in cancer and its complications, inflammatory bowel disease (IBD), inflammatory lung disease (ILD), influenza-induced pneumonitis, necrotizing enterocolitis (NEC), neonatal chronic lung disease (CLD), periodontitis, pre-eclampsia, retinopathy of prematurity (ROP), sepsis, systemic inflammatory response syndrome (SIRS), thrombosis, transfusion-related acute lung injury (TRALI), vasculitis, autoimmune syndromes including, but not limited to, rheumatoid arthritis (RA), systemic lupus erythematosus (SLE), and Wegener's granulomatosis (WG), and disorders of nonresolved inflammation. There are other inflammatory disorders not listed herein but known to those skilled in the art. For example, see Kumar et al., Robbins and Cotran Pathologic Basis of Disease, pp. 43-77, 8th Edition, 2010, Saunders Elsevier, Philadelphia, Pa.; Nathan, Nature, 2002, 420: 846-852; and Amulic et al., Annu Rev Immunol, 2012, 30: 459-489.

The phrase "does not globally depress polymorphonuclear leukocyte (PMN) function," when used in connection with a NIP, means that although the NIP may inhibit or substantially inhibit NETosis, the NIP does not inhibit or substantially inhibit other PMN functions. Other PMN functions include, but are not limited to, chemotaxis, chemokine synthesis and secretion, cytokine synthesis and secretion, extracellular bacterial killing, intracellular bacterial killing, phagocytosis, and/or reactive oxygen species (ROS) generation. Methods of assaying these functions are known in the art. For example, Example 11 describes methods of assaying phagocytic bacterial killing.

Methods

This disclosure relates to therapeutic and related uses of NET Inhibitory Peptides (NIPs), neonatal NET-Inhibitory Factors (nNIFs), nNIF analogs, nNIF-Related Peptides (nNRPs), and nNRP analogs, particularly for inhibiting NETosis and/or the formation of neutrophil extracellular traps (NETs).

A first aspect of the disclosure relates to methods of treating inflammatory disorders.

In certain embodiments, this disclosure provides methods of treating a patient having an inflammatory disorder comprising administering to the patient an effective amount of a pharmaceutical composition comprising a NIP, or a pharmaceutically acceptable salt of a NIP, and a pharmaceutically acceptable carrier to reduce a pathological effect or symptom of the inflammatory disorder. The pathological effects or symptoms may include one or more of the following: pain, heat, redness, swelling and/or edema, hypotension, fibrosis and/or post-inflammatory fibrosis, end organ failure (i.e., renal, cardiac, hepatic), tissue damage, and/or loss of function.

In some embodiments, this disclosure provides methods of treating a patient having an inflammatory disorder comprising administering to the patient an effective amount of a pharmaceutical composition comprising a nNIF, or a pharmaceutically acceptable salt of a nNIF, and a pharmaceutically acceptable carrier to reduce a pathological effect or symptom of the inflammatory disorder.

In other embodiments, the disclosure provides methods of treating a patient having an inflammatory disorder comprising administering to the patient an effective amount of a pharmaceutical composition comprising a nNIF analog, or a pharmaceutically acceptable salt of a nNIF analog, and a pharmaceutically acceptable carrier to reduce a pathological effect or symptom of the inflammatory disorder.

In yet other embodiments, the disclosure provides methods of treating a patient having an inflammatory disorder comprising administering to the patient an effective amount of a pharmaceutical composition comprising a nNRP, or a pharmaceutically acceptable salt of a nNRP, and a pharmaceutically acceptable carrier to reduce a pathological effect or symptom of the inflammatory disorder.

In still other embodiments, the disclosure provides methods of treating a patient having an inflammatory disorder comprising administering to the patient an effective amount of a pharmaceutical composition comprising an nNRP analog, or a pharmaceutically acceptable salt of a nNRP analog, and a pharmaceutically acceptable carrier to reduce a pathological effect or symptom of the inflammatory disorder.

In some embodiments, the patient may be a mammal. In certain embodiments the patient may be a human. Any patient or subject requiring inhibition of NETosis and/or NET formation may potentially be a candidate for treatment with a NIP, a pharmaceutically acceptable salt of a NIP, a nNIF, a pharmaceutically acceptable salt of a nNIF, a nNIF analog, a pharmaceutically acceptable salt of a nNIF analog, a nNRP, a pharmaceutically acceptable salt of a nNRP, a nNRP analog, and/or a pharmaceutically acceptable salt of a nNRP analog.

In some embodiments, the inflammatory disorder may at least partially involve or be at partially caused by neutrophil extracellular trap (NET) formation and/or NETosis. In some embodiments, the inflammatory disorder may be an acute inflammatory disorder, a chronic inflammatory disorder, and/or an immune disorder. In other embodiments, the inflammatory disorder may be an autoimmunity disorder. In yet other embodiments, the inflammatory disorder may be a disorder of coagulation.

In some embodiments, the inflammatory disorder may be one or more of, but not limited to, acute respiratory distress syndrome (ARDS), bronchopulmonary dysplasia (BPD), chronic obstructive pulmonary disease (COPD), cystic fibrosis, inflammation in cancer and its complications, inflammatory bowel disease (IBD), inflammatory lung disease (ILD), influenza-induced pneumonitis, necrotizing enterocolitis (NEC), neonatal chronic lung disease (CLD), periodontitis, pre-eclampsia, retinopathy of prematurity (ROP), sepsis, systemic inflammatory response syndrome (SIRS), thrombosis, transfusion-related acute lung injury (TRALI), vasculitis, autoimmune syndromes including, but not limited to, rheumatoid arthritis (RA), systemic lupus erythematosus (SLE), and Wegener's granulomatosis (WG), and disorders of nonresolved inflammation. There are other inflammatory disorders not listed herein but known to those skilled in the art. For example, see Kumar et al., Robbins and Cotran Pathologic Basis of Disease, pp. 43-77, 8th Edition, 2010, Saunders Elsevier, Philadelphia, Pa.; Nathan, Nature, 2002, 420: 846-852; and Amulic et al., Annu Rev Immunol, 2012, 30: 459-489.

In some embodiments, the pharmaceutical composition may substantially inhibit NET formation and/or NETosis. In other embodiments, the pharmaceutical composition may inhibit or substantially inhibit NET-mediated inflammatory tissue damage.

The particular form of NIP, nNIF, nNIF analog, nNRP, nNRP analog, and/or salt thereof selected for inhibiting NETosis and/or NET formation can be prepared by a variety of techniques known for generating peptide products. For example, vertebrate forms of nNIF and nNRP can be obtained by extraction from the natural source, using an appropriate combination of protein isolation techniques. Other techniques are also within the scope of this disclosure.

In certain embodiments, NIPs, nNIFs, nNIF analogs, nNRPs, nNRP analogs, and/or salts thereof can be synthesized using standard techniques of peptide chemistry and can be assessed for inhibition of NETosis and/or NET formation activity. With respect to synthesis, the selected NIP, nNIF, nNIF analog, nNRP, nNRP analog, and/or salt thereof can be prepared by a variety of techniques for generating peptide products. Those NIPs, nNIFs, nNIF analogs, nNRPs, nNRP analogs, and/or salts thereof that incorporate only L-amino acids can be produced in commercial quantities by application of recombinant DNA technology. For this purpose, DNA coding for the desired NIP, nNIF, nNIF analog, nNRP, and/or nNRP analog is incorporated into an expression vector and transformed into a host cell (e.g., yeast, bacteria, or a mammalian cell) which is then cultured under conditions appropriate for NIP, nNIF, nNIF analog, nNRP, and/or nNRP analog expression. A variety of gene expression systems have been adapted for this purpose, and typically drive expression of the desired gene from expression regulatory elements used naturally by the chosen host.

In an approach applicable to the production of a selected NIP, nNIF, nNIF analog, nNRP, and/or nNRP analog, and one that may be used to produce a NIP, nNIF, nNIF analog, nNRP, and/or nNRP analog that incorporates non-genetically encoded amino acids and N- and C-terminally derivatized forms, the techniques of automated peptide synthesis may be employed, general descriptions of which appear, for example, in Stewart and Young, Solid Phase Peptide Synthesis, 2nd Edition, 1984, Pierce Chemical Company, Rockford, Ill.; Bodanszky and Bodanszky, The Practice of Peptide Synthesis, 1984, Springer-Verlag, New York, N.Y.; and Applied Biosystems 430A Users Manual, 1987, ABI Inc., Foster City, Calif. In these techniques, a NIP, nNIF, nNIF analog, nNRP, and/or nNRP analog is grown from its C-terminal, resin-conjugated residue by the sequential addition of appropriately protected amino acids, using either the 9-fluoroenylmethyloxycarbonyl (Fmoc) or tert-butyloxycarbonyl (t-Boc) protocols, as described for instance by Orskov et al., FEBS Lett, 1989, 247(2): 193-196.

Once the desired NIP, nNIF, nNIF analog, nNRP, and/or nNRP analog has been synthesized, cleaved from the resin and fully deprotected, the peptide may then be purified to ensure the recovery of a single oligopeptide having the selected amino acid sequence. Purification may be achieved using any of the standard approaches, which include, but are not limited to, reversed-phase high-pressure liquid chromatography (RP-HPLC) on alkylated silica columns (e.g., C4-, C8-, or C18-silica). Such column fractionation is generally accomplished by running linear gradients (e.g., 10-90%) of increasing percent organic solvent (e.g., acetonitrile, in aqueous buffer) usually containing a small amount (e.g., 0.1%) of pairing agent such as trifluoroacetic acid (TFA) or triethanolamine (TEA). Alternatively, ion-exchange HPLC can be employed to separate peptide species on the basis of their charge characteristics. Column fractions are collected, and those containing peptide of the desired and/or required purity are optionally pooled. In one embodiment of the invention, the NIP, nNIF, nNIF analog, nNRP, and/or nNRP analog may then be treated in the established manner to exchange the cleavage acid (e.g., TFA) with a pharmaceutically acceptable acid, such as acetic, hydrochloric, phosphoric, maleic, tartaric, succinic, and the like, to generate a pharmaceutically acceptable acid addition salt of the peptide.

Analogs of human NIPs, nNIFs, and/or nNRPs can be generated using standard techniques of peptide chemistry and can be assessed for inhibition of NETosis and/or NET formation activity, all according to the guidance provided herein. Particularly preferred analogs of the invention are those based upon the sequences of human nNIF (SEQ ID NO: 1) and/or CRISPP (SEQ ID NO: 2), as follows (wherein X can be any naturally occurring amino acid):

```
                                              SEQ ID NO: 1
KAVLTIDEKGTEAAGAMFLEAIPMSIPPEVKFNKPFVFLMIEQNTKSPL

FMGKVVNPTQK

SEQ ID NO: 2
MXIPPEVKFNKPFVFLMIDQNTKVPLFMGK
```

Any substitution, addition, or deletion of an amino acid or amino acids of a NIP, nNIF, and/or nNRP that does not destroy the NET-inhibitory activity of the NIP, nNIF, and/or nNRP may be usefully employed in this disclosure. In certain embodiments, the NIP, nNIF, and/or nNRP analogs are at least as active as the native human NIP, nNIF, and/or nNRP. NET-inhibitory activity may be determined in vitro as described in this disclosure. In other embodiments, the NIP, nNIF, and/or nNRP analog has one or more enhanced properties compared with the native human NIP, nNIF, and/or nNRP. For example, such analogs may exhibit enhanced serum stability, enhanced receptor binding and enhanced signal-transducing activity. Other modifications to NIPs, nNIFs, nNIF analogs, nNRPs, and/or nNRP analogs that may usefully be employed in this disclosure are those which render the molecule resistant to oxidation.

A researcher may determine whether a particular NIP, nNIF, nNIF analog, nNRP, nNRP analog, and/or salt thereof may be used to treat an inflammatory disorder by administering the peptide or analog to individuals who have the inflammatory disorder. The researcher may then determine, using diagnostic biomarkers, whether the individuals thus treated show decreased inflammation and improvement of the inflammatory condition.

The disclosure also encompasses non-conservative substitutions of amino acids in any vertebrate NIP, nNIF, and/or nNRP sequence, provided that the non-conservative substitutions occur at amino acid positions known to vary in NIPs, nNIFs, and/or nNRPs isolated from different species. Non-conserved residue positions are readily determined by aligning known vertebrate NIP, nNIF, and/or nNRP sequences.

For administration to patients, the NIP, nNIF, nNIF analog, nNRP, nNRP peptide, and/or salt thereof, may be provided in pharmaceutically acceptable form (e.g., as a preparation that is sterile-filtered, e.g., through a 0.22µ filter, and substantially pyrogen-free). It may be desired that the NIP, nNIF, and/or nNRP peptide to be formulated migrates as a single or individualized peak on HPLC, exhibits uniform and authentic amino acid composition and sequence upon analysis thereof, and otherwise meets standards set by the various national bodies which regulate quality of pharmaceutical products.

The aqueous carrier or vehicle may be supplemented for use as an injectable with an amount of gelatin that serves to depot the NIP, nNIF, nNIF analog, nNRP, nNRP analog, and/or salt thereof at or near the site of injection, for its slow release to the desired site of action. Concentrations of gelatin effective to achieve the depot effect are expected to lie in the range from 10-20%. Alternative gelling agents, such as hyaluronic acid (HA), may also be useful as depoting agents.

The NIPs, nNIFs, nNIF analogs, nNRPs, nNRP analogs, and/or salts thereof of the present disclosure may also be formulated as slow release implantation formulations for extended and sustained administration of the NIP, nNIF, nNIF analog, nNRP, nNRP analog, and/or salt thereof. Examples of such sustained release formulations include composites of biocompatible polymers, such as poly(lactic acid), poly(lactic-co-glycolic acid), methylcellulose, hyaluronic acid, collagen, and the like. The structure, selection, and use of degradable polymers in drug delivery vehicles have been reviewed in several publications, including, Domb et al., Polym Advan Technol, 1992, 3: 279-292. Additional guidance in selecting and using polymers in pharmaceutical formulations can be found in the text by Chasin and Langer (eds.), Biodegradable Polymers as Drug Delivery Systems, Vol. 45 of Dekker, Drugs and the Pharmaceutical Sciences, 1990, New York, N.Y. Liposomes may also be used to provide for the sustained release of a nNIF, nNIF analog, nNRP, nNRP analog, and/or salt thereof. Details concerning how to use and make liposomal formulations of drugs of interest can be found in, among other places, U.S. Pat. Nos. 4,944,948; 5,008,050; 4,921,706; 4,927,637; 4,452,747; 4,016,100; 4,311,712; 4,370,349; 4,372,949; 4,529,561; 5,009,956; 4,725,442; 4,737,323; and 4,920,016. Sustained release formulations may be of particular interest when it is desirable to provide a high local concentration of a NIP, nNIF, nNIF analog, nNRP, nNRP analog, and/or salt thereof (e.g., near the site of inflammation to inhibit NETosis and/or NET formation, etc.).

The NIPs, nNIFs, nNIF analogs, nNRPs, nNRP analogs, and/or salts thereof of the present disclosure may also be incorporated into a device or devices, both implanted or topical, for extended and sustained administration of the NIP, nNIF, nNIF analog, nNRP, nNRP analog, and/or salt thereof.

For therapeutic use, the chosen NIP, nNIF, nNIF analog, nNRP, nNRP analog, and/or salt thereof may be formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to Remington: The Science and Practice of Pharmacy, 22nd Edition, 2012, Pharmaceutical Press, London, UK. In one embodiment of the invention, the compounds may be formulated for administration by infusion or by injection (e.g., subcutaneously, intramuscularly, or intravenously), and may be accordingly utilized as aqueous solutions in sterile and pyrogen-free form and optionally buffered to physiologically tolerable pH (e.g., a slightly acidic or physiological pH). Thus, the compounds may be administered in a vehicle such as distilled water, saline, phosphate buffered saline, or 5% dextrose solution. Water solubility of the NIP, nNIF, nNIF analog, nNRP, nNRP analog, and/or salt thereof may be enhanced, if desired, by incorporating a solubility enhancer, such as acetic acid.

Another aspect of the disclosure relates to methods of treating complications of prematurity.

In embodiments, this disclosure provides for methods of treating a patient having a complication of prematurity comprising administering to the patient an effective amount of a pharmaceutical composition comprising a NIP, or a pharmaceutically acceptable salt of a NIP, and a pharmaceutically acceptable carrier to reduce a pathological effect or symptom of the complication of prematurity, such as the prolonged need for oxygen support associated with neonatal chronic lung disease or the need for surgical intervention or prolonged total parenteral nutrition in infants that develop necrotizing enterocolitis.

In some embodiments, this disclosure provides for methods of treating a patient having a complication of prematurity comprising administering to the patient an effective amount of a pharmaceutical composition comprising a nNIF, or a pharmaceutically acceptable salt of a nNIF, and a pharmaceutically acceptable carrier to reduce a pathological effect or symptom of the complication of prematurity.

In other embodiments, the disclosure provides methods of treating a patient having a complication of prematurity comprising administering to the patient an effective amount of a pharmaceutical composition comprising a nNIF analog, or a pharmaceutically acceptable salt of a nNIF analog, and a pharmaceutically acceptable carrier to reduce a pathological effect or symptom of the complication of prematurity.

In yet other embodiments, the disclosure provides methods of treating a patient having a complication of prematurity comprising administering to the patient an effective amount of a pharmaceutical composition comprising a nNRP, or a pharmaceutically acceptable salt of a nNRP, and a pharmaceutically acceptable carrier to reduce a pathological effect or symptom of the complication of prematurity.

In still other embodiments, the disclosure provides methods of treating a patient having a complication of prematurity comprising administering to the patient an effective amount of a pharmaceutical composition comprising a nNRP analog, or a pharmaceutically acceptable salt of a nNRP analog, and a pharmaceutically acceptable carrier to reduce a pathological effect or symptom of the complication of prematurity.

In some embodiments, the patient may be a mammal. In certain embodiments the patient may be a human.

In some embodiments, the complication of prematurity may at least partially involve or be at least partially caused by neutrophil extracellular trap (NET) formation and/or NETosis. In certain embodiments, the pharmaceutical composition may substantially inhibit NET formation and/or NETosis. In other embodiments, the pharmaceutical composition may inhibit or substantially inhibit NET-mediated inflammatory tissue damage.

In some embodiments, the complication of prematurity may be one or more of, but not limited to, necrotizing enterocolitis (NEC), respiratory distress syndrome (RDS), pneumonia, bronchopulmonary dysplasia (BPD), neonatal chronic lung disease (CLD), neurodevelopmental delay, retinopathy of prematurity (ROP), and/or sepsis.

A further aspect of the disclosure relates to methods of prophylaxis against inflammatory disorders.

In some embodiments, the disclosure provides for methods of prophylaxis against an inflammatory disorder in a patient at risk of developing an inflammatory disorder, comprising administering to the patient an effective amount of a pharmaceutical composition comprising a NIP, or a pharmaceutically acceptable salt of a NIP, and a pharmaceutically acceptable carrier to reduce the risk of developing a pathological effect or symptom of the inflammatory disorder.

In some embodiments, the disclosure provides for methods of prophylaxis against an inflammatory disorder in a patient at risk of developing an inflammatory disorder, comprising administering to the patient an effective amount of a pharmaceutical composition comprising a nNIF, or a pharmaceutically acceptable salt of a nNIF, and a pharmaceutically acceptable carrier to reduce the risk of developing a pathological effect or symptom of the inflammatory disorder.

In other embodiments, the disclosure provides for methods of prophylaxis against an inflammatory disorder in a patient at risk of developing an inflammatory disorder comprising administering to the patient an effective amount of a pharmaceutical composition comprising a nNIF analog, or a pharmaceutically acceptable salt of a nNIF analog, and a pharmaceutically acceptable carrier to reduce the risk of developing a pathological effect or symptom of the inflammatory disorder.

In yet other embodiments, the disclosure provides for methods of prophylaxis against an inflammatory disorder in a patient at risk of developing an inflammatory disorder comprising administering to the patient an effective amount of a pharmaceutical composition comprising a nNRP, or a pharmaceutically acceptable salt of a nNRP, and a pharmaceutically acceptable carrier to reduce the risk of developing a pathological effect or symptom of the inflammatory disorder.

In still other embodiments, the disclosure provides for methods of prophylaxis against an inflammatory disorder in a patient at risk of developing an inflammatory disorder comprising administering to the patient an effective amount of a pharmaceutical composition comprising a nNRP analog, or a pharmaceutically acceptable salt of the nNRP analog, and a pharmaceutically acceptable carrier to reduce the risk of developing a pathological effect or symptom of the inflammatory disorder.

In some embodiments, the patient may be a mammal. In other embodiments the patient may be a human.

In some embodiments, the inflammatory disorder may at least partially involve or be at partially caused by neutrophil extracellular trap (NET) formation and/or NETosis. In some embodiments, the inflammatory disorder may be an acute inflammatory disorder. In other embodiments, the inflammatory disorder may be a chronic inflammatory disorder. In other embodiments, the inflammatory disorder may be an autoimmunity disorder. In yet other embodiments, the inflammatory disorder may be a disorder of coagulation.

In some embodiments, the inflammatory disorder may be one or more of, but not limited to, the inflammatory disorders defined and/or listed above.

In some embodiments, the pharmaceutical composition may substantially inhibit NET formation and/or NETosis. In other embodiments, the pharmaceutical composition may inhibit or substantially inhibit NET-mediated inflammatory tissue damage.

Another aspect of the disclosure relates to methods of prophylaxis against complications of prematurity.

In embodiments, this disclosure provides methods of prophylaxis against complications of prematurity in a patient at risk of developing a complication of prematurity comprising administering to the patient an effective amount of a pharmaceutical composition comprising a neonatal NIP, or a pharmaceutically acceptable salt of a NIP, and a pharmaceutically acceptable carrier to reduce the risk of developing a pathological effect or symptom of the complication of prematurity.

In some embodiments, this disclosure provides methods of prophylaxis against complications of prematurity in a patient at risk of developing a complication of prematurity comprising administering to the patient an effective amount of a pharmaceutical composition comprising a neonatal nNIF, or a pharmaceutically acceptable salt of a nNIF, and a pharmaceutically acceptable carrier to reduce the risk of developing a pathological effect or symptom of the complication of prematurity.

In certain embodiments, the disclosure provides methods of prophylaxis against complications of prematurity in a patient at risk of developing a complication of prematurity, comprising administering to the patient an effective amount of a pharmaceutical composition comprising a nNIF analog, or a pharmaceutically acceptable salt of a nNIF analog, and a pharmaceutically acceptable carrier to reduce the risk of developing a pathological effect or symptom of the complication of prematurity.

In yet other embodiments, the disclosure provides methods of prophylaxis against complications of prematurity in a patient at risk of developing a complication of prematurity, comprising administering to the patient an effective amount of a pharmaceutical composition comprising a nNIF-Related Peptide (nNRP), or a pharmaceutically acceptable salt of a nNRP, and a pharmaceutically acceptable carrier to reduce the risk of developing a pathological effect or symptom of the complication of prematurity.

In still other embodiments, the disclosure provides methods of prophylaxis against complications of prematurity in a patient at risk of developing a complication of prematurity, comprising administering to the patient an effective amount of a pharmaceutical composition comprising a nNRP analog, or a pharmaceutically acceptable salt of a nNRP analog, and a pharmaceutically acceptable carrier to reduce the risk of developing a pathological effect or symptom of the complication of prematurity.

In some embodiments, the patient may be a mammal. In other embodiments the patient may be a human.

In some embodiments, the complication of prematurity may at least partially involve or be at least partially caused by neutrophil extracellular trap (NET) formation and/or NETosis. In other embodiments, the pharmaceutical composition may substantially inhibit NET formation and/or NETosis. In yet other embodiments, the pharmaceutical composition may inhibit or substantially inhibit NET-mediated inflammatory tissue damage.

In other embodiments, the complication of prematurity may be one or more of, but not limited to, necrotizing enterocolitis (NEC), respiratory distress syndrome (RDS), pneumonia, bronchopulmonary dysplasia (BPD), neonatal chronic lung disease (CLD), neurodevelopmental delay, retinopathy of prematurity (ROP), and/or sepsis.

Pharmaceutical Compositions

In a further aspect, this disclosure relates to pharmaceutical compositions comprising NIPs.

In some embodiments, the pharmaceutical composition may comprise a neonatal NET-Inhibitory Factor (nNIF), or a pharmaceutically acceptable salt of a nNIF, and a pharmaceutically acceptable carrier. In another embodiment, the pharmaceutical composition may comprise a nNIF analog, or a pharmaceutically acceptable salt of a nNIF analog, and a pharmaceutically acceptable carrier. In yet other embodiments, the pharmaceutical composition may comprise a nNIF-Related Peptide (nNRP), or a pharmaceutically acceptable salt of a nNRP, and a pharmaceutically acceptable carrier. In still other embodiments, the pharmaceutical composition may comprise a nNRP analog, or a pharmaceutically acceptable salt of a nNRP analog, and a pharmaceutically acceptable carrier.

In certain embodiments, the pharmaceutical composition may comprise nNIF, or the salt thereof, and the nNIF, or the salt thereof, may comprise the amino acid sequence:

```
SEQ ID NO: 1:
KAVLTIDEKGTEAAGAMFLEAIPMSIPPEVKFNKPFVFLMIEQNTKSPL

FMGKVVNPTQK
```

In other embodiments, at least one amino acid of nNIF, the salt of the nNIF, the nNIF analog, the salt of the nNIF analog, the nNRP, the salt of the nNRP, the nNRP analog, or the salt of the nNRP analog, may be bound to a chemical modifier. In some embodiments, the chemical modifier may be selected from at least one of a lipid, a polyethylene glycol (PEG), a saccharide, or any other suitable molecule. Other chemical modifications of the pharmaceutical composition, for example, cationization, methylization, and cyclization, are also within the scope of this disclosure.

Attachment of a lipid to the peptide (lipidization) may increase lipophilicity of the pharmaceutical composition.

Attachment of a PEG to the peptide (PEGylation) increases the molecular weight of the peptide. In some embodiments, PEGylation may improve solubility of the pharmaceutical composition. In other embodiments, PEGylation may reduce dosage frequency and/or toxicity of the pharmaceutical composition. In other embodiments, PEGylation may extend circulating life of the pharmaceutical composition, and/or extend stability of the pharmaceutical composition, and/or may enhance protection of the pharmaceutical composition from proteolytic degradation. PEGylation may also reduce immunogenicity and/or antigenicity of the pharmaceutical composition.

Attachment of one or more saccharides to the peptide (glycosylation) may serve a variety of functional and/or structural roles in the pharmaceutical composition. Glycosylation may improve delivery of the pharmaceutical composition to a target or to targets of choice. Glycosylation may also reduce the toxicity of the pharmaceutical composition.

In some embodiments, the pharmaceutical composition comprising nNIF, the salt of the nNIF, the nNIF analog, the salt of the nNIF analog, the nNRP, the salt of the nNRP, the nNRP analog, or the salt of the nNRP analog, may be present in an amount effective to inhibit, or to substantially inhibit, damage selected from at least one of inflammatory tissue injury and/or inflammatory vascular injury.

In some embodiments, the pharmaceutical composition comprising nNIF, the salt of the nNIF, the nNIF analog, the salt of the nNIF analog, the nNRP, the salt of the nNRP, the nNRP analog, or the salt of the nNRP analog, may not globally depress functions of polymorphonuclear leukocytes (PMNs). The functions of PMNs include, but are not limited to, chemotaxis, phagocytosis, reactive oxygen species (ROS) generation, cytokine/chemokine synthesis and secretion, NET formation/NETosis, and/or intracellular/extracellular bacterial killing. In certain embodiments, the pharmaceutical composition may not inhibit or substantially inhibit PMN phagocytosis. In other embodiments, the pharmaceutical composition may not inhibit or substantially inhibit PMN chemotaxis. In yet other embodiments, the pharmaceutical composition may not inhibit or substantially inhibit generation of ROS. In other embodiments, the pharmaceutical composition may not inhibit or substantially inhibit PMN intracellular bacterial killing.

In some embodiments, the pharmaceutical composition may comprise a nNIF analog, a salt of a nNIF analog, a nNRP analog, or a salt of a nNRP analog, and the analog or the salt of the analog may not be a naturally occurring analog or salt of the analog.

In some embodiments, the pharmaceutical composition may be present in an amount effective to inhibit, or to substantially inhibit, NET formation and/or NETosis. In some embodiments, the NET formation and/or NETosis may be stimulated by a bacterium, a fungus, a parasite, a virus, and/or any other appropriate stimulator of NET formation and/or NETosis. In certain embodiments, the virus may be a hemorrhagic fever virus. Hemorrhagic fever viruses are described, e.g., in Borio et al., JAMA, 2002, 287(18): 2391-2405 and include, but are not limited to, filoviruses such as Ebola virus and Marburg virus, arenaviruses such as Lassa virus, hantaviruses, and flaviviruses such as dengue virus and yellow fever virus. In other embodiments, the NET formation and/or NETosis may be stimulated by one or more bacterial species, including, but not limited to, *Bacillus* species, *Escherichia* species, *Francisella* species, *Streptococcus* species, *Staphylococcus* species, *Yersinia* species, and/or any other appropriate gram-negative or gram-positive bacterium or bacteria. In embodiments, the *Bacillus* species may be *Bacillus anthracis* (anthrax). In embodiments, the *Escherichia* species may be *Escherichia coli*. In embodiments, the *Francisella* species may be *Francisella tularensis* (tularemia). In embodiments, the *Staphylococcus* species may be *Staphylococcus aureus*.

In other embodiments, the NET formation and/or NETosis may be stimulated by beta-defensin 1, HIV-1, lipopolysaccharide (LPS), phorbol myristate acetate (PMA), and/or *Staphylococcus aureus* alpha-toxin.

In some embodiments, the pharmaceutical composition may comprise nNRP, Cancer-Associated SCM-Recognition, Immune Defense Suppression, and Serine Protease Protection Peptide (CRISPP), and/or a CRISPP analog. In some other embodiments, the pharmaceutical composition may comprise A1ATm$^{358}$, and/or an A1ATm$^{358}$ analog, as A1ATm$^{358}$ also inhibits NET formation. In other embodiments, the pharmaceutical may comprise another nNRP. In other embodiments, the nNRP may be an isolated and purified component of umbilical cord blood.

In an additional aspect, this disclosure relates to compositions for inhibiting the formation of NETs and/or NETosis in a mammal.

In some embodiments, a composition for inhibiting the formation of NETs and/or NETosis in a mammal may comprise an nNIF, a pharmaceutically acceptable salt of the nNIF, a nNIF analog, a pharmaceutically acceptable salt of the nNIF analog, an nNRP, a pharmaceutically acceptable salt of the nNRP, a nNRP analog, or a pharmaceutically acceptable salt of the nNRP analog, and a pharmaceutically acceptable carrier. In certain embodiments the mammal may be a human.

Isolated and Purified Peptides

In a further aspect, this disclosure relates to a NET-inhibitory peptide (NIP).

In some embodiments, the NIP may be an isolated and purified nNIF protein comprising SEQ ID NO: 1. In certain other embodiments, the isolated and purified nNIF protein may comprise at least twenty-four contiguous amino acids of SEQ ID NO: 1. In yet other embodiments, the isolated and purified nNIF protein may comprise at least twelve contiguous amino acids of SEQ ID NO: 1. In still other embodiments, the isolated and purified nNIF protein may comprise at least six contiguous amino acids of SEQ ID NO: 1.

In some embodiments, the NIP may be an isolated and purified nNIF protein wherein the sequence may be at least eighty percent identical to SEQ ID NO: 1. In other embodiments, the isolated and purified nNIF may be at least sixty percent identical to SEQ ID NO: 1. In yet other embodiments, the isolated and purified nNIF may be at least forty percent identical to SEQ ID NO: 1. In still other embodiments, the isolated and purified nNIF may be at least twenty percent identical to SEQ ID NO: 1.

In another aspect, this disclosure relates to a nNIF protein analog. In some embodiments, the nNIF protein analog may be an isolated and purified nNIF analog.

An effective dosage and treatment protocol may be determined by conventional means, e.g., by starting with a low dose in laboratory animals and then increasing the dosage while monitoring the effects, and systematically varying the dosage regimen as well. Numerous factors may be taken into consideration by a clinician when determining an optimal dosage for a given subject. Primary among these is whether any NIPs are normally circulating in the plasma and, if so, the amount of any such NIPs. Additional factors include the size of the patient, the age of the patient, the general condition of the patient, the particular disorder being treated, the severity of the disorder, the presence of other drugs in the patient, the in vivo activity of the NIP, nNIF, nNIF analog, nNRP, nNRP analog, salt thereof, and the like. The trial dosages may be chosen after consideration of the results of animal studies and the clinical literature.

There are many specific therapeutic regimens used to assess whether a molecule has a desired effect. A researcher faced with the task of determining whether a particular NIP, nNIF, nNIF analog, nNRP, and/or nNRP analog may be used for inhibition of NETosis and/or NET formation would choose the appropriate regimen to make this determination.

Delivery methods and formulations useful for administering peptides to individuals are known in the art, and a skilled person would be able to determine the suitability of any particular method of delivery of a peptide to an individual for particular circumstances. For the purposes of illustration only, the following examples of methods and formulations for administering peptides to individuals are provided.

Peptides may be administered to individuals orally; however, actions of the digestive system may reduce the bioavailability of the peptide. In order to increase peptide oral bioavailability, peptides may be administered in formulations containing enzyme inhibitors, or the peptides may be administered as part of a micelle, nanoparticle, or emulsion in order to protect the peptide from digestive activity.

Peptides may also be administered by means of an injection. The peptides may be injected subcutaneously, intramuscularly, or intravenously. Further disclosure regarding methods of administering peptides through injection is found, e.g., in U.S. Pat. No. 5,952,301.

Peptides may further be administered by pulmonary delivery. A dry powder inhalation system may be used, wherein peptides are absorbed through the tissue of the lungs, allowing delivery without injection, while bypassing the potential reduction in bioavailability seen with oral administration. See Onoue et al., Expert Opin Ther Pat, 2008, 18: 429.

For use in inhibiting NETosis and/or NET formation in a mammal, including a human, the present disclosure provides in one of its aspects a package or kit, in the form of a sterile-filled vial or ampoule, that contains a NETosis and/or NET formation inhibiting amount of a NIP, nNIF, nNIF analog, nNRP, nNRP analog, and/or salt thereof in either unit dose or multi-dose amounts, wherein the package or kit incorporates a label instructing use of its contents for the inhibition of such NETosis and/or NET formation. In one embodiment of the invention, the package or kit contains the NIP, nNIF, nNIF analog, nNRP, nNRP analog, and/or salt thereof and the desired carrier, as an administration-ready formulation. Alternatively, and according to another embodiment of the invention, the package or kit provides the NIP, nNIF, nNIF analog, nNRP, nNRP analog, and/or salt thereof, in a form, such as a lyophilized form, suitable for reconstitution in a suitable carrier, such as phosphate-buffered saline.

In one embodiment, the package or kit is a sterile-filled vial or ampoule containing an injectable solution which comprises an effective, NETosis and/or NET formation inhibiting amount of NIP, nNIF, nNIF analog, nNRP, nNRP analog and/or salt thereof dissolved in an aqueous vehicle.

EXAMPLES

To further illustrate these embodiments, the following examples are provided. These examples are not intended to limit the scope of the claimed invention, which should be determined solely on the basis of the attached claims.

Example 1—Comparing Human Adult and Neonatal PMNs

NET-formation was assessed in human and neonatal PMNs. In contrast to adult human PMNs, as shown in FIG.

Figure 1C:
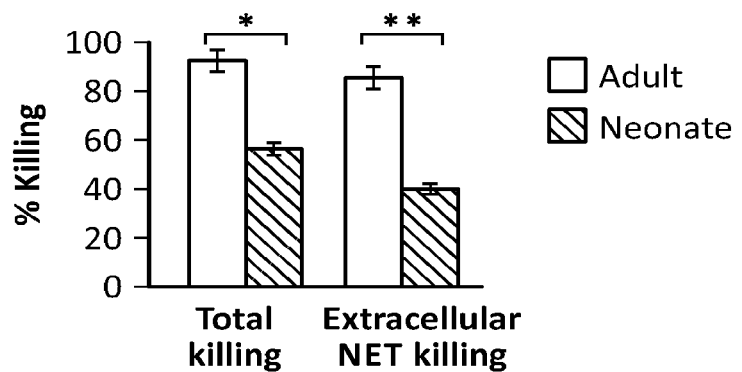
FIG. 1C is a graph indicating that neonatal PMNs demonstrate significantly decreased total and NET-mediated bacterial killing as compared to adult PMNs. * $p<0.05$, ** $p<0.001$.

1B, neonatal PMNs isolated from cord blood do not form NETs. Further, NET-mediated bacterial killing was assessed in human adult and neonatal PMNs. As indicated in FIG. 1C, neonatal PMNs demonstrate significantly decreased total and NET-mediated bacterial killing as compared to adult PMNs. * $p<0.05$, ** $p<0.001$.

Example 2—Inducing NET Formation by *S. aureus* Sepsis

Figure 2A:
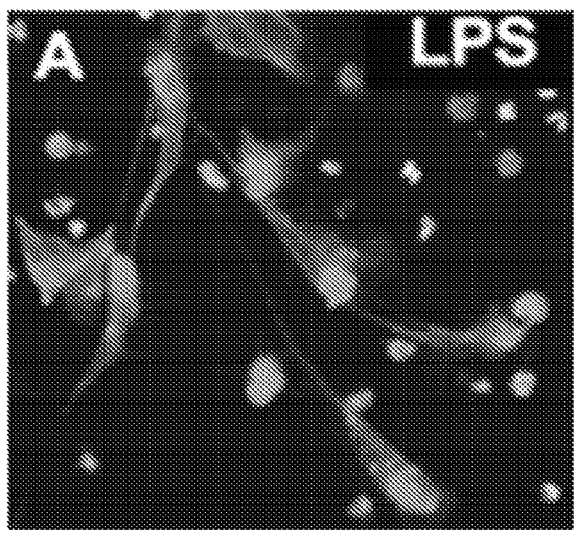
FIG. 2A is an image of NET formation by human PMNs stimulated with LPS (1 hour time point).
Figure 2B:
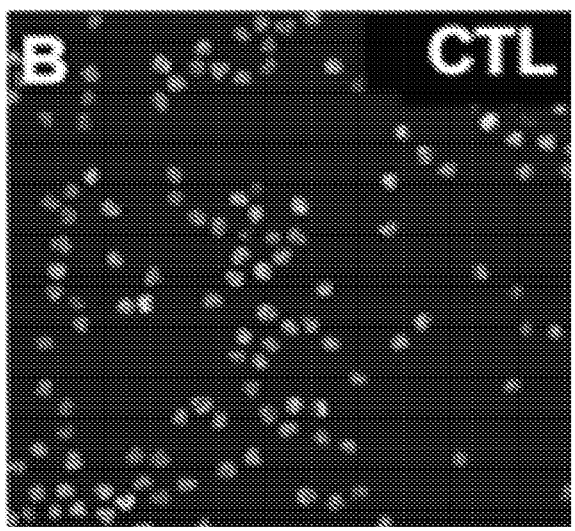
FIG. 2B is an image of human PMNs incubated in control plasma (1 hour time point).
Figure 2C:
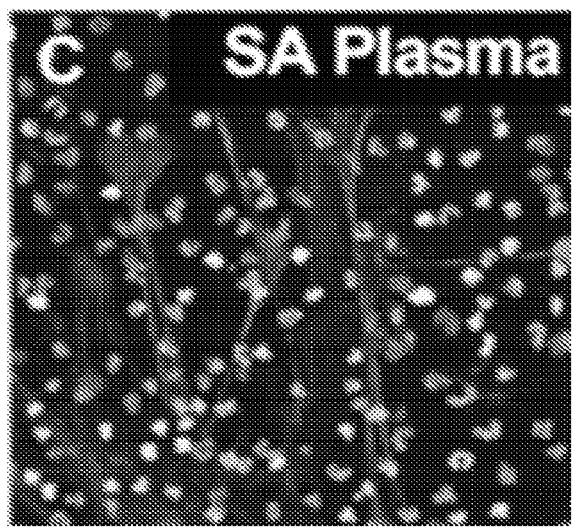
FIG. 2C is an image of NET formation by human PMNs incubated in plasma isolated from patients with S. aureus sepsis (1 hour time point).

NET-formation was assessed in control and stimulated human PMNs at a 1 hour time point. Human PMNs were stimulated with either LPS, control plasma, or with plasma isolated from patients with *S. aureus* sepsis. Plasma from patients with *S. aureus* sepsis induces NET formation by human PMNs, as shown in FIGS. 2A-2C.

Example 3—Observing Impaired NET Formation at Birth

Figure 3A:
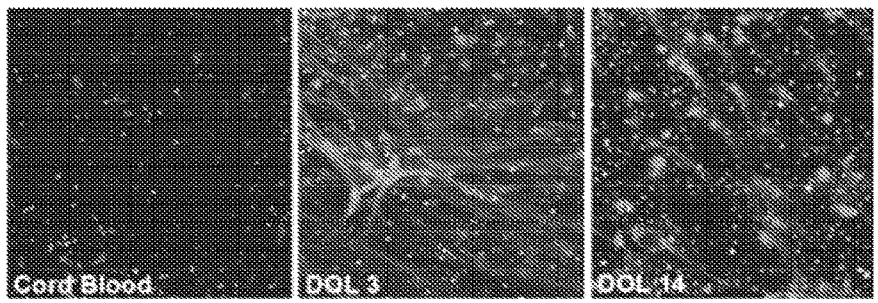
FIG. 3A is a series of images showing LPS-stimulated preterm PMNs isolated from the same preterm infant. PMNs were isolated from cord blood, at day of life 3, and day of life 14, as indicated.
Figure 3B:
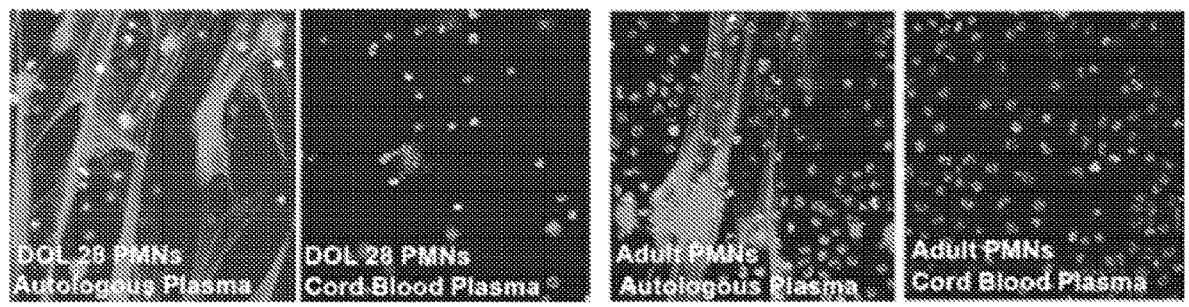
FIG. 3B is a series of images (left to right) showing the results of pre-incubation experiments: day of life 28 PMNs pre-incubated in autologous plasma, day of life 28 PMNs pre-incubated with cord blood plasma, adult PMNs pre-incubated with autologous plasma, and adult PMNs pre-incubated with cord blood plasma. NET formation was then induced with LPS stimulation.
Figure 3C:
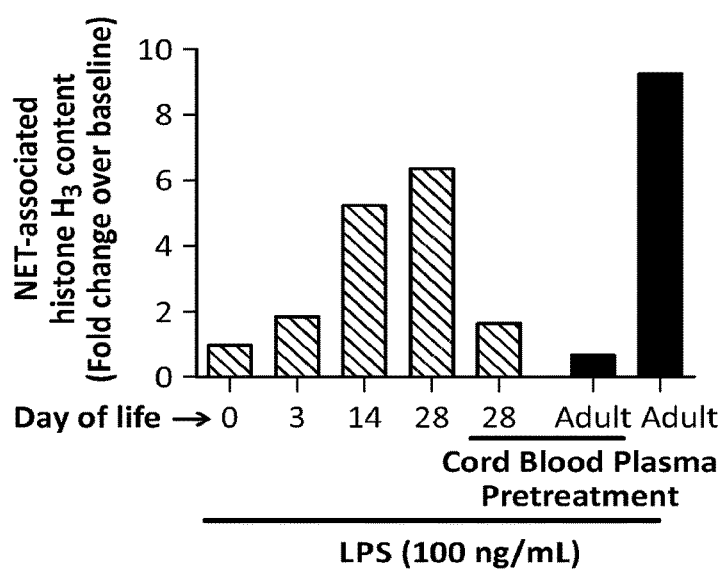
FIG. 3C is a graph depicting extracellular histone $H_3$ release. Extracellular histone content (fold change over baseline) is represented on the y-axis. Data from one preterm infant's PMNs through day of life 28 and one adult's PMNs from the plasma switch experiments of FIG. 3B are represented on the x-axis.
Figure 5A:
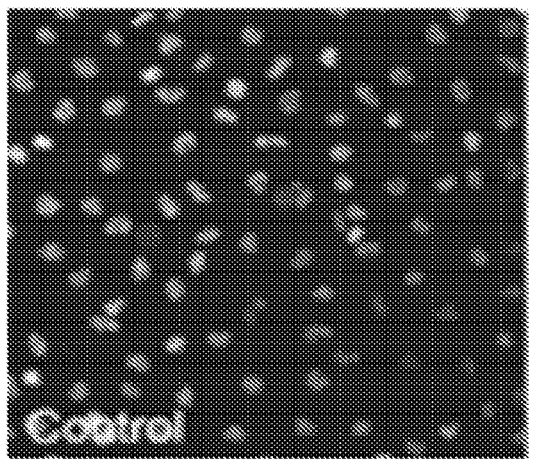
FIG. 5A is an image of untreated control adult PMNs.
Figure 5B:
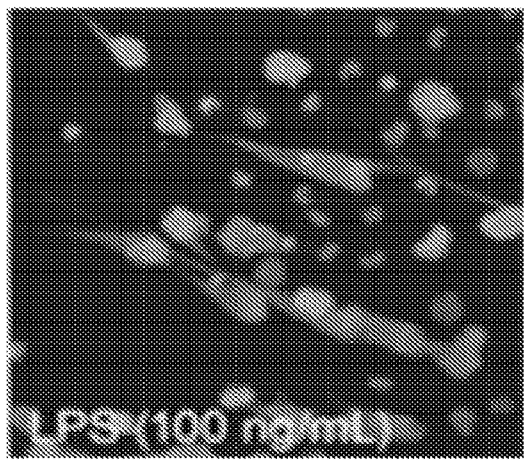
FIG. 5B is an image of adult PMNs with LPS treatment.
Figure 5C:
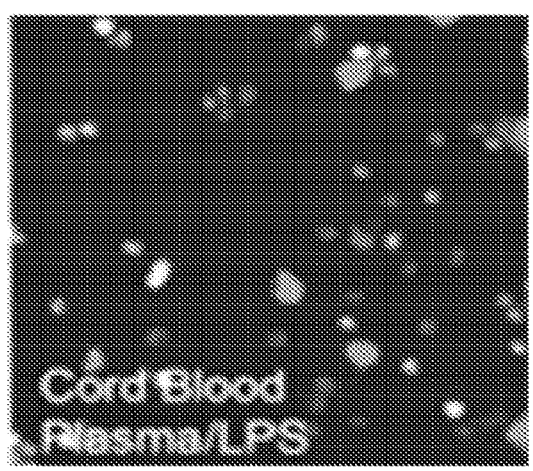
FIG. 5C is an image of adult PMNs with LPS treatment following pre-incubation with untreated cord blood plasma.
Figure 5D:
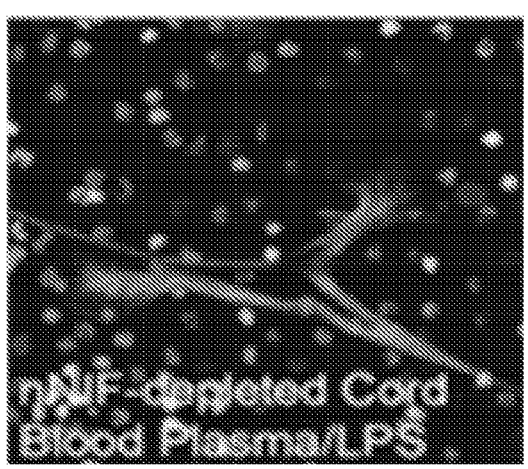
FIG. 5D is an image of adult PMNs with LPS treatment following pre-incubation with nNIF-depleted cord blood plasma.
Figure 5E:
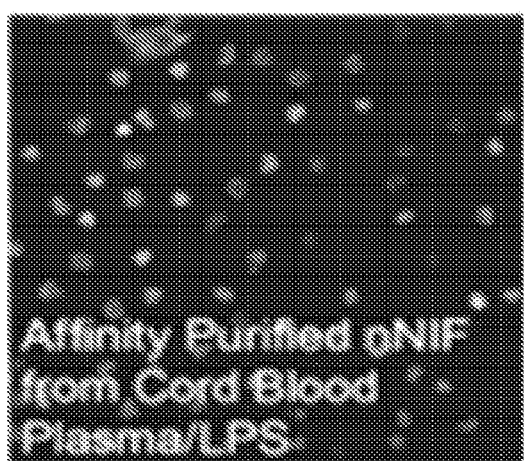
FIG. 5E is an image of adult PMNs with LPS treatment following pre-incubation with affinity purified nNIF from cord blood plasma.
Figure 5F:
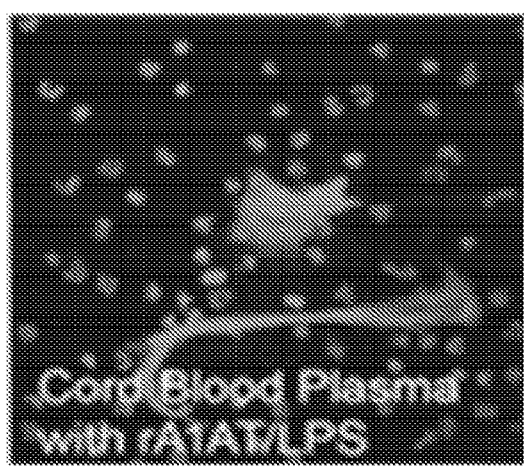
FIG. 5F is an image of adult PMNs with LPS treatment following pre-incubation with full length rA1AT.

PMNs were isolated from the cord blood of infants born at less than 30 weeks gestation and, subsequently, from serially drawn peripheral blood from the same infants through the first 60 days of life. As shown in FIGS. 3A-3C, NET formation was assessed qualitatively and quantitatively, and impaired NET formation by PMNs was observed at the time of birth. In contrast, robust NET formation by PMNs was observed from blood samples isolated on day of life 3 or later.

Example 4—Demonstrating NET Formation Inhibitor in Cord Blood

PMNs from healthy adult donors and from 28 day old preterm infants were pre-incubated for one hour with thawed cord blood plasma from that particular preterm infant or with autologous plasma collected that day from either the preterm infant peripheral blood sample or the blood sample from the healthy adult. NET formation was then assessed in vitro following LPS-stimulation (100 ng/mL) for 2 hours. Cord blood plasma pre-incubation significantly decreased NET formation by both neonatal and adult LPS-stimulated PMNs as compared to PMNs pre-incubated with control plasma (see FIGS. 3B and 14C).

Figure 14A:
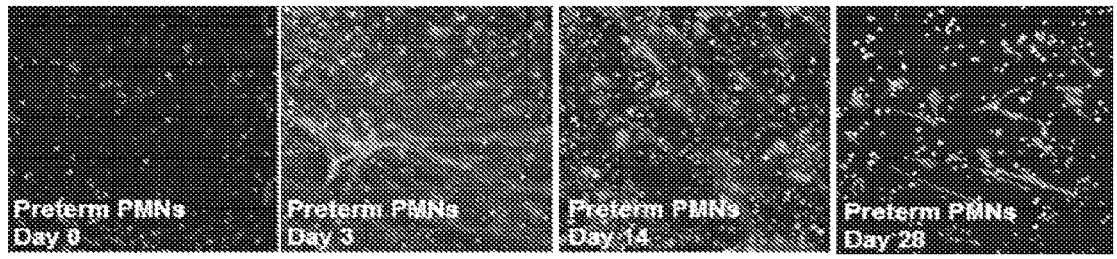
FIG. 14A is a series of images showing LPS-stimulated preterm PMNs isolated from the same preterm infant. PMNs were isolated at day of life 0, day of life 3, day of life 14, and day of life 28, as indicated.
Figure 14B:
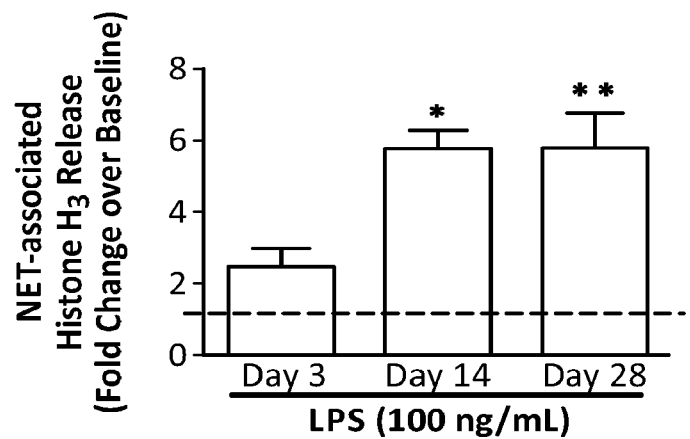
FIG. 14B is a graph depicting extracellular histone $H_3$ release. Extracellular histone content (fold change over baseline) is represented on the y-axis. Data from 7 preterm infant's PMNs through day of life 28 are represented on the x-axis. * denotes p<0.05 and ** denotes p<0.01 compared to the control (dashed line), arbitrarily set at 1.
Figure 14C:
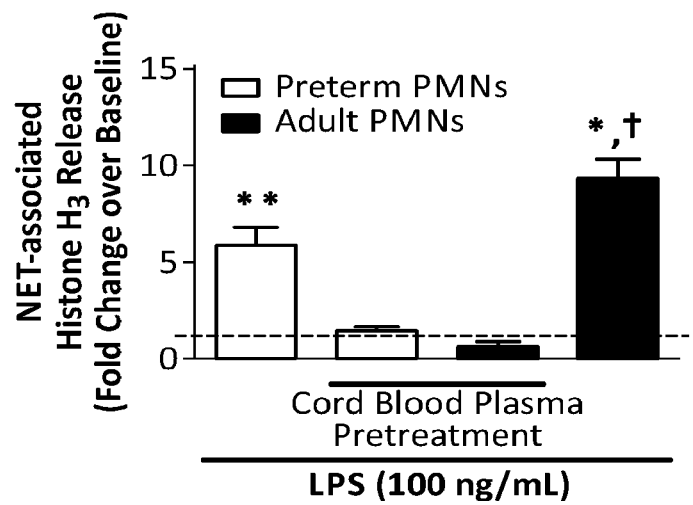
FIG. 14C is a graph depicting extracellular histone $H_3$ release. Extracellular histone content (fold change over baseline) is represented on the y-axis. Data from five preterm infant's PMNs on day of life 28 and five adult's PMNs from the plasma switch experiments of FIG. 3B are represented on the x-axis. * denotes p<0.05 LPS/Adult versus LPS/Preterm, ** denotes p<0.01 LPS/Preterm versus cord blood LPS/Preterm, and † denotes p<0.001 LPS/Adult versus cord blood LPS/Adult.

As illustrated in FIGS. 3B and 14C, human cord blood pre-incubation experiments demonstrate that cord blood plasma can inhibit NET formation by day of life 28 autologous preterm infant PMNs and by healthy adult donor PMNs, while pre-incubation with autologous plasma isolated from the respective study subjects on that day may not. FIG. 3B shows NET-associated, extracellular DNA and nuclear DNA (60× magnification).

Extracellular histone $H_3$ release was used as a quantifiable surrogate for NET formation as depicted in FIG. 14C. As illustrated, extracellular histone content (fold change over baseline) is represented on the y-axis, and data from five preterm infant's PMNs on day of life 28 and five adult's PMNs, from the above-described plasma switch experiments, are represented on the x-axis. * denotes $p<0.05$ LPS/Adult versus LPS/Preterm, ** denotes $p<0.01$ LPS/Preterm versus cord blood LPS/Preterm, and † denotes $p<0.001$ LPS/Adult versus cord blood LPS/Adult. The one-way ANOVA statistical tool with Tukey's post-hoc testing was employed.

Cord blood and peripheral blood plasma switch experiments demonstrated that autologous cord blood plasma inhibits NET formation by NET-competent PMNs isolated from the same infant on day of life 28, and also by PMNs isolated from healthy adults, indicating that an inhibitory factor that blocks PMN NET formation is present in cord blood, but that activity of the factor disappears or is dramatically reduced after birth (see FIGS. 3B and 3C).

Example 5—Identifying Neonatal NET-Inhibitory Factor (nNIF)

Proteomic techniques were used to compare the cord blood plasma proteome with that of plasma isolated from the same preterm infant at 28 days of age (see FIGS. 3B and 14C). Following abundant protein removal, parallel 2-dimensional gel electrophoresis was performed on each plasma sample, separating proteins first by isoelectric focusing and then by molecular weight. Six protein spots were noted to be differentially present upon comparison of the two gels. Four protein clusters were present in the gel of cord blood plasma but not in the 28 day plasma gel; two protein clusters were present in the 28 day plasma gel but not the cord blood plasma gel. Each of these protein clusters were cut out of the respective gels for protein identification. The oligopeptide sequences following trypsin-digest and tandem mass spectroscopy were compared to the NCBI Human trypsin-specific database (current through May 13, 2011). A partial list of proteins identified by mass spectroscopy on one of the protein clusters present on the cord blood gel but not on the 28 day plasma gel is included in FIG. 4A. Of the proteins identified in this protein cluster, two related peptides with predicted molecular weights of ≈4 kD and protein scores of >100 became candidate peptides for NET-inhibitory activity. The novel peptide was named neonatal NET-inhibitory Factor (nNIF). A nNIF-related peptide (NRP) was known in the literature: Cancer-Associated SCM-Recognition, Immunedefense Suppression, and Serine Protease Protection Peptide (CRISPP). Next, it was determined that nNIF and CRISPP have significant homology to the carboxy terminus of full length alpha 1-antitrypsin (AAT, also referred to herein as A1AT) (see FIG. 4C). Using a polyclonal antibody generated against the last 18 amino acids of AAT, it was demonstrated using western blotting that nNIF is present in increased amounts in cord blood plasma as compared to healthy adult plasma (see FIGS. 15A and 15B).

Figure 15A:
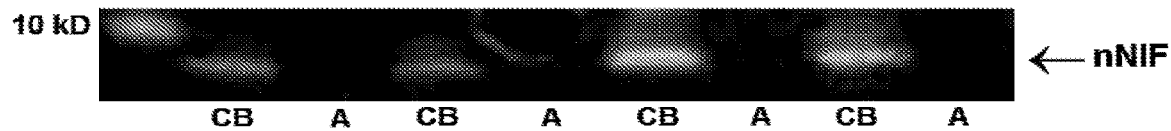
FIG. 15A is a western blot using a polyclonal antibody against the carboxy-terminus of alpha 1-antitrypsin (AAT, also referred to herein as A1AT) comparing nNIF (≈4-6 kD) expression in cord blood (CB) and adult plasma (A).
Figure 15B:
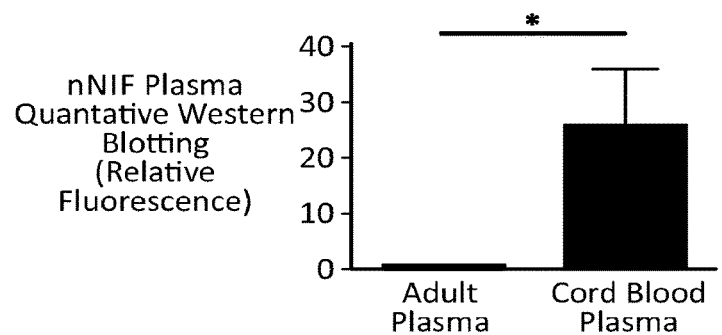
FIG. 15B is a graph quantitating the results of FIG. 15A. * denotes p<0.05.

As discussed, protein expression in cord blood plasma and day of life 28 plasma from the same preterm infant was compared using 2D-gel electrophoresis, and a protein spot present in cord blood but not in day of life 28 plasma was detected. A list of nNIF candidate proteins from that protein spot following mass spectroscopy is outlined with expected molecular masses and protein scores in FIG. 4A. The list includes full length AAT and two 29 amino-acid peptides with significant homology to the carboxy-terminus of AAT: nNIF and CRISPP. As illustrated in FIG. 4C, nNIF and AAT share significant carboxy terminus homology. The sequences obtained from mass spectroscopy are shown and compared, and the published sequence of CRISPP is also compared. Western blotting using a polyclonal antibody against the carboxy-terminus of AAT is shown in FIG. 15A, demonstrating increased expression of nNIF (≈4-6 kD) in cord blood as compared to adult plasma. As shown in FIG. 15B, these results were quantified using relative fluorescence and a statistically significant difference was found between four cord blood plasma nNIF levels (CB) and those of four healthy adult controls (A). * denotes $p<0.05$. The Student's t-test statistical tool was used.

In summary, protein expression in cord blood and day of life 28 plasma from the same preterm infant was compared using 2D-gel electrophoresis. A protein spot present in cord blood but not in day of life 28 plasma was detected. An endogenous peptide (≈4-6 kD) with significant NET inhibitory activity was identified. This peptide was provisionally named neonatal NET-inhibitory factor (nNIF).

Example 6—Characterizing the nNIF Peptide

Mass spectroscopy was used to further characterize the nNIF peptide of Example 5 and to resolve major portions of its sequence. A list of nNIF candidate proteins from the protein spot of Example 5 following mass spectroscopy is outlined with expected molecular mass and protein score in FIG. 4A. As shown in FIG. 4C, nNIF was found to have significant homology to a carboxy-terminus cleavage fragment of A1AT. An antibody against the carboxy terminus of A1AT was used to detect a 4-6 kD peptide in cord blood plasma that was only minimally present in adult plasma (see FIG. 4B).

Example 7—Further Characterization of the nNIF Peptide

Cord blood plasma was depleted of all full length and fragmented A1AT using affinity purification (AP) with the A1AT carboxy-terminus antibody. As shown in FIGS. 5A-5F, cord blood plasma depleted of nNIF failed to inhibit NET formation, while pretreatment with the AP eluted proteins inhibited NET formation by LPS-stimulated PMNs. Addition of recombinant full length A1AT to the depleted plasma did not inhibit NET formation. These data suggest that nNIF is a cleavage fragment of A1AT or a similar peptide and not the full length protein.

Example 8—Identifying the nNIF-Related Peptide (nNRP), CRISPP

Significant homology was identified between nNIF and Cancer-Associated SCM-Recognition, and Serine Protease Protection Peptide (CRISPP) (see FIG. 4C). CRISPP peptide was synthesized and it was observed that CRISPP blocked NET formation by LPS-stimulated PMNs in a concentration dependent manner. A scrambled control peptide did not block NET formation by LPS-stimulated PMNs.

Example 9—Inhibiting NET Formation with CRISPP Treatment

Figure 6A:
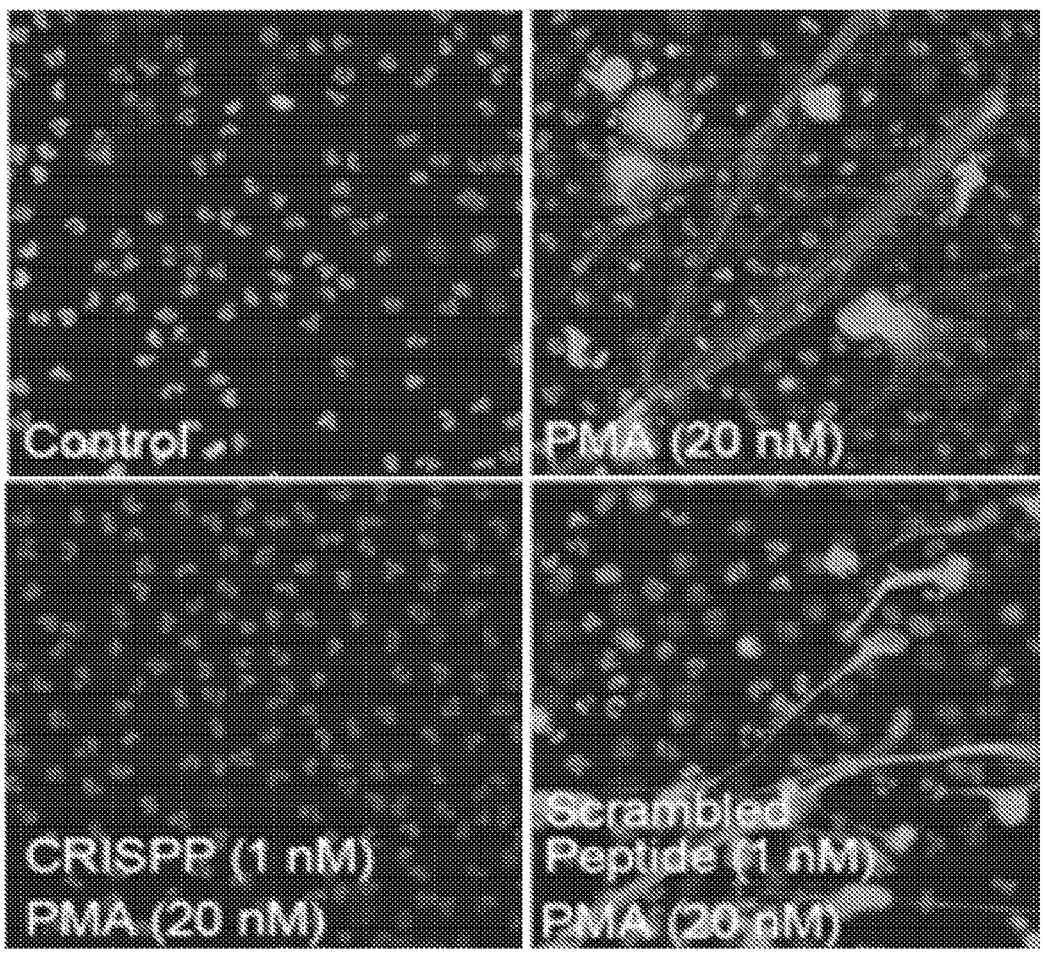
FIG. 6A is a series of images (clockwise from top left) showing adult human PMN NET formation in: control PMNs, PMA-stimulated (20 nM) PMNs, PMA-stimulated (20 nM) PMNs with scrambled peptide (1 nM) pre-incubation, and PMA-stimulated (20 nM) PMNs with CRISPP (1 nM) pre-incubation.
Figure 6B:
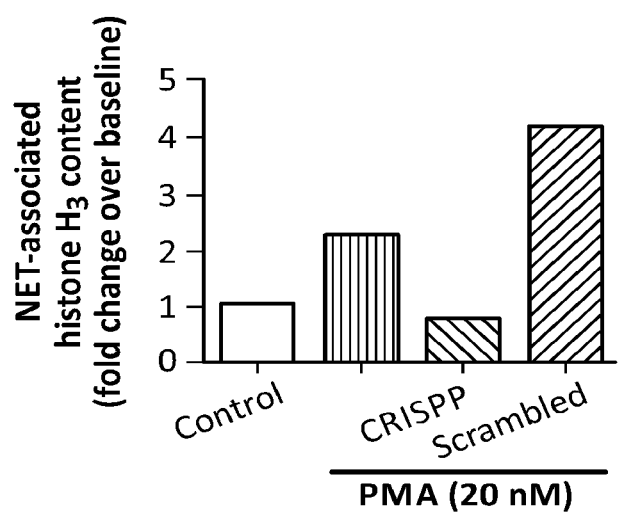
FIG. 6B is a graph showing the results of a human histone $H_3$ release assay to quantify NET formation. Extracellular histone content (fold change over baseline) is represented on the y-axis. Data from human PMNs stimulated under indicated conditions are represented on the x-axis.

NET formation by PMA-stimulated adult PMNs with or without CRISPP pre-incubation was assessed. As shown in FIGS. 6A and 6B, CRISPP pretreatment (1 nM) for 1 hour prior to stimulation inhibited NET formation while pretreatment with a scrambled control peptide (1 nM) did not. CRISPP was observed to block NET formation induced by PMA.

Example 10—Analyzing NET Formation in Multiple In Vitro Infection Models

Figure 7A:
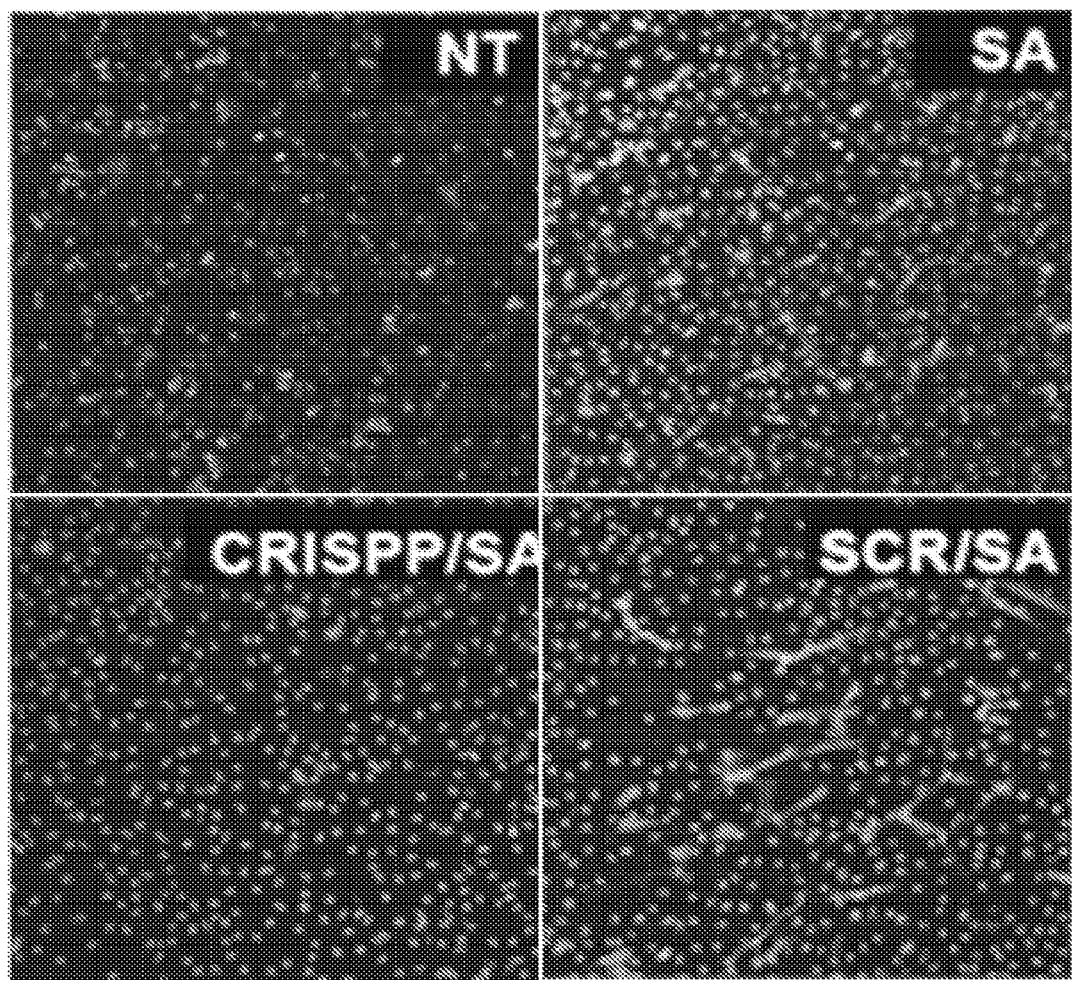
FIG. 7A is a series of images (clockwise from top left) showing human PMN NET formation by: no treatment, S. aureus incubation, S. aureus incubation and scrambled control peptide (1 nM) pre-incubation, and S. aureus incubation and CRISPP (1 nM) pre-incubation.
Figure 7B:
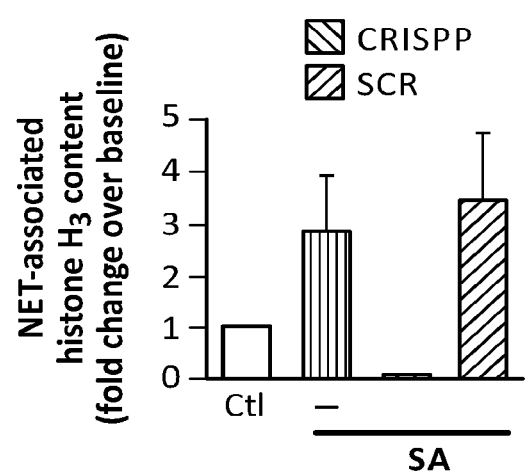
FIG. 7B is a graph showing the results of a human histone $H_3$ release assay to quantify NET formation (n=2). Extracellular histone content (fold change over baseline) is represented on the y-axis. Data from human PMNs stimulated under indicated conditions are represented on the x-axis.

A human histone $H_3$ release assay was used to quantify NET formation (n=2). NET-inhibitory activity of CRISPP was tested using in vitro models of two human infectious diseases: *Staphylococcus aureus* bacteremia and dengue fever. *S. aureus* has previously been shown to induce NET formation by PMNs from human adults. Pretreatment with CRISPP completely blocked NET formation by human PMNs incubated with live *S. aureus* (see FIGS. 7A and 7B). In contrast, incubation with a scrambled control peptide did not block NET formation by human PMNs.

Figure 8A:
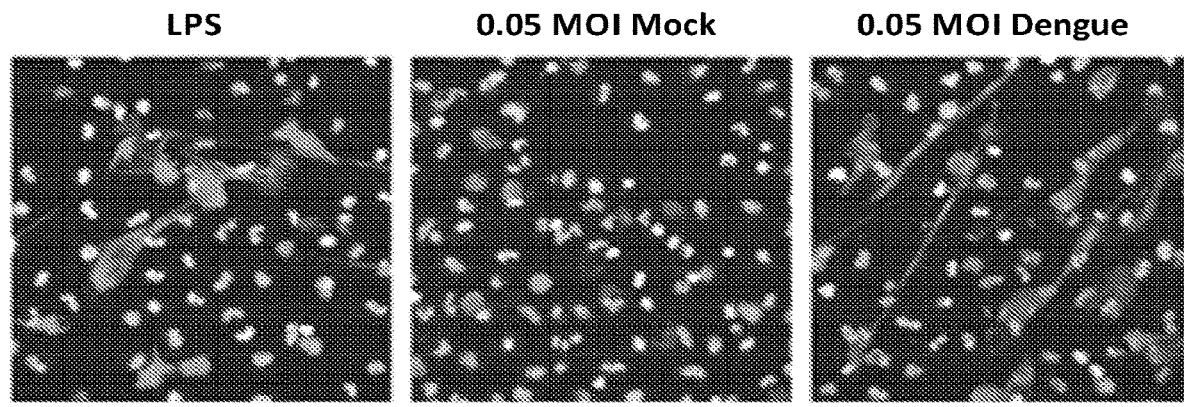
FIG. 8A is a series of images (left to right) showing NET formation in human PMNs incubated with: LPS (100 ng/mL), dengue virus media without infection, and dengue virus (0.05 MOI).
Figure 8B:
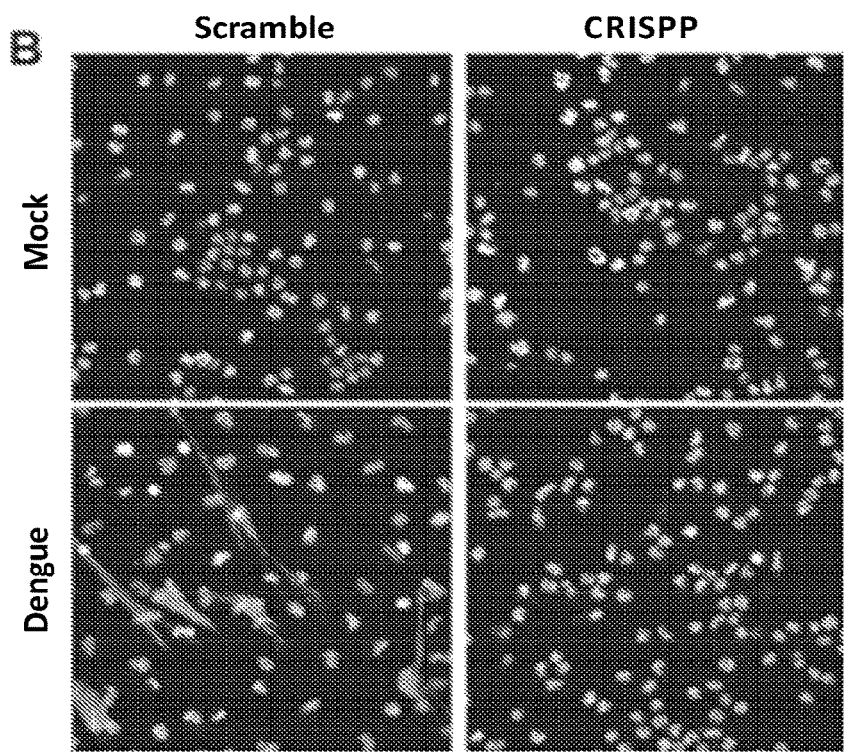
FIG. 8B is a series of images showing (clockwise from top left) human PMNs incubated with: dengue virus media without infection and pretreated with scrambled control peptide (1 nM), dengue virus media without infection and pretreated with CRISPP (1 nM), dengue virus and pretreated with CRISPP (1 nM), and dengue virus and pretreated with scrambled control peptide (1 nM).

As shown in FIGS. 8A and 8B, human PMNs were incubated with dengue virus (0.05 MOI) and qualitatively assessed for NET formation. Mock incubation using dengue virus media without infection served as a control. Dengue virus induced NET formation by PMNs from human adults. Pretreatment with CRISPP (1 nM) for 1 hour prior to stimulation completely blocked NET formation by human PMNs incubated with dengue virus. In contrast, incubation with a scrambled control peptide (1 nM) did not block NET formation by human PMNs.

Example 11—Determining Effect of CRISPP Treatment on PMN Functions

Figure 9:
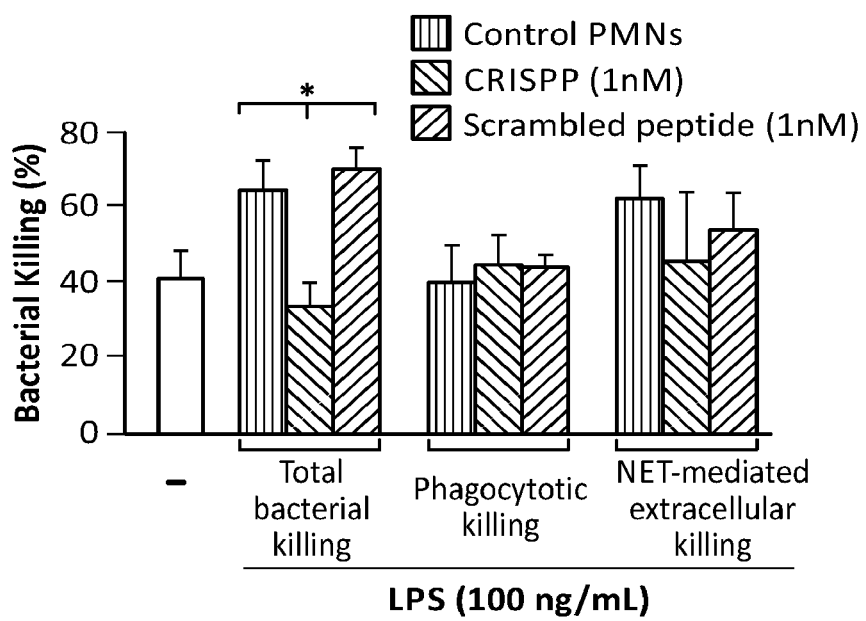
FIG. 9 is a graph showing total, phagocytotic, and NET-mediated extracellular bacterial killing of a pathogenic strain of E. coli by human PMNs with or without LPS stimulation (100 ng/mL). PMNs were also pretreated with CRISPP (1 nM), or a scrambled peptide control (1 nM). * denotes statistical significance (p<0.05).

Total, phagocytotic, and NET-mediated extracellular bacterial killing of a pathogenic strain of *E. coli* by human PMNs±LPS stimulation (100 ng/mL) was assessed, and the results are summarized in FIG. 9. PMNs were also pretreated with CRISPP (1 nM), or a scrambled control peptide control (1 nM). Phagocytotic killing was inhibited with cytochalasin B and D pretreatment (10 μM). NET-mediated killing was inhibited using DNase treatment to dismantle NETs prior to addition of the bacteria. CRISPP pretreatment significantly decreased total and NET-mediated bacterial killing of *E. coli*, but did not alter phagocytic killing, as measured using the one-way ANOVA statistical tool with Newman-Keuls Multiple Comparison Test post-hoc analysis.

Example 12—Assessing Effect of CRISPP Treatment in Murine Models

Figure 17A:
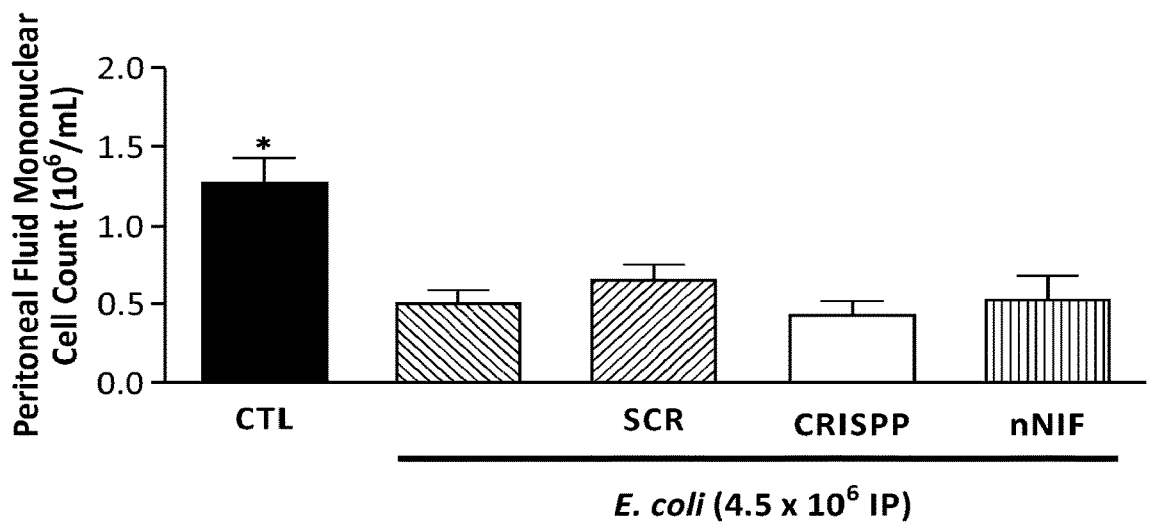
FIG. 17A is a graph depicting mononuclear cell counts in peritoneal fluid under indicated conditions. * denotes $p<0.05$ for CTL versus all other groups.
Figure 17B:
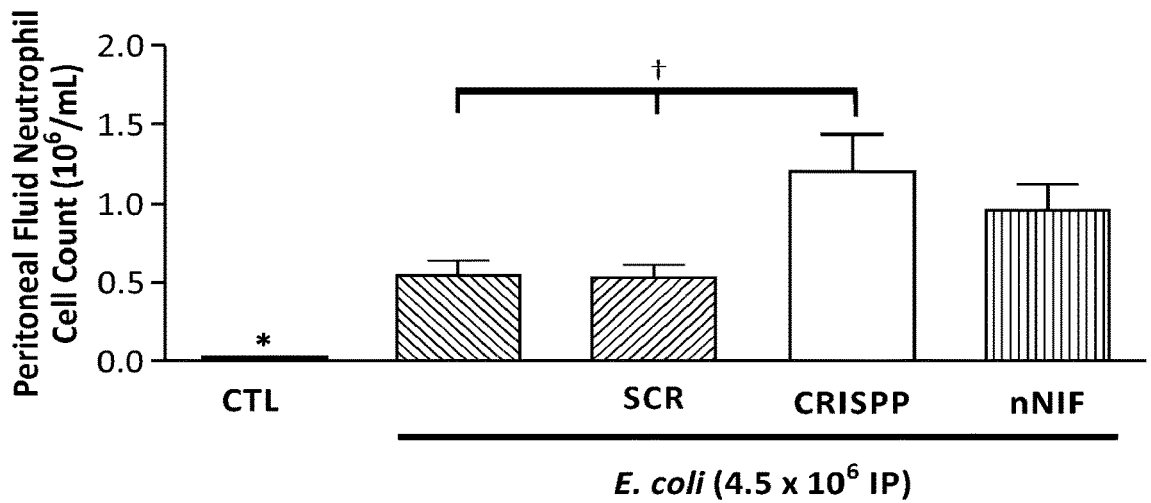
FIG. 17B is a graph depicting neutrophil cell counts in peritoneal fluid under indicated conditions. * denotes $p<0.05$ for CTL versus all other groups and † denotes $p<0.05$ for CRISPP/*E. coli* versus SCR/*E. coli* and *E. coli* groups.
Figure 17C:
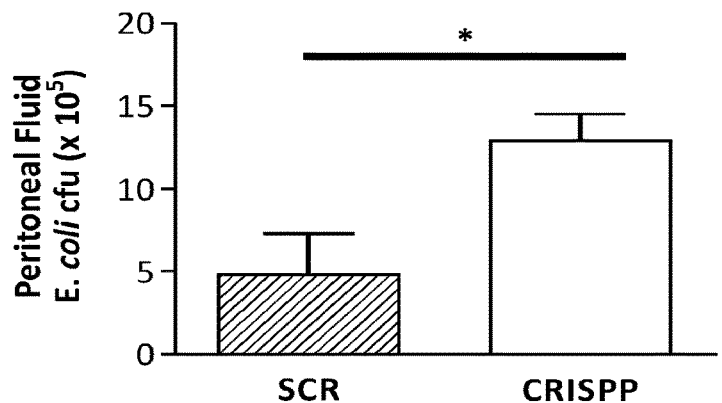
FIG. 17C is a graph depicting *E. coli* colony-forming units (cfu) in peritoneal fluid under indicated conditions. * denotes $p≤0.05$.

The ability of CRISPP to inhibit NET formation in vivo was assessed using murine models of *E. coli* peritonitis. Outbred Swiss-Webster mice were injected intraperitoneally with $4.5 \times 10^7$ colony-forming units (cfu) of *E. coli*±nNIF, CRISPP, or scrambled control peptide (SCR) (10 mg/kg, IP injection) one hour prior to *E. coli* infection. At the 3 hour time point after infection, 3 mice were sacrificed and the peritoneal fluid and peritoneal tissue were collected and analyzed for leukocyte accumulation, bacteriology, and in vivo NET formation. Total mononuclear and polymorphonuclear leukocyte counts were determined in the peritoneal fluid and demonstrated a statistically significant increase in peritoneal PMN accumulation in all experimental groups compared to control (see FIG. 17A). Mice pretreated with CRISPP demonstrated a significant increase in PMN accumulation compared to *E. coli* alone or SCR pretreated mice (see FIGS. 17A and 17B). This result appears consistent with a CRISPP-mediated decrease in neutrophil cell death through inhibition of NETosis. See Fuchs et al., J Cell Biol, 2007, 176: 231-241. The number of *E. coli* cfu/mL of peritoneal fluid in CRISPP pretreated mice was also determined compared to SCR mice (see FIG. 17C). A significant increase in peritoneal fluid bacterial concentration was detected in CRISPP pretreated animals compared to SCR, indicating that the inhibition of NETosis and NET formation may lead to decreased bacterial killing and higher peritoneal fluid concentrations of bacteria.

Figure 10A:
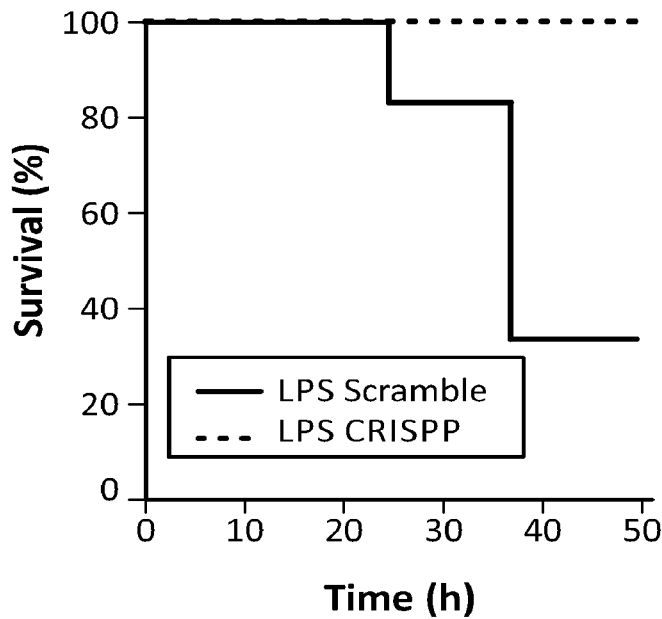
FIG. 10A is a graph tracking survival of C57BL6 mice in various treatment arms following intraperitoneal injection of LPS (20 mg/kg). CRISPP-treated mice (10 mcg/kg/dose) received 2 doses intraperitoneally; one given 1 hour prior to infection and one dose given 6 hours after infection. The same dose, delivery route, and schedule were followed for the scrambled peptide control mice. Six mice were assessed in both groups. The LPS plus CRISPP group survival was statistically greater than the LPS plus scrambled peptide group (p=0.02).
Figure 10B:
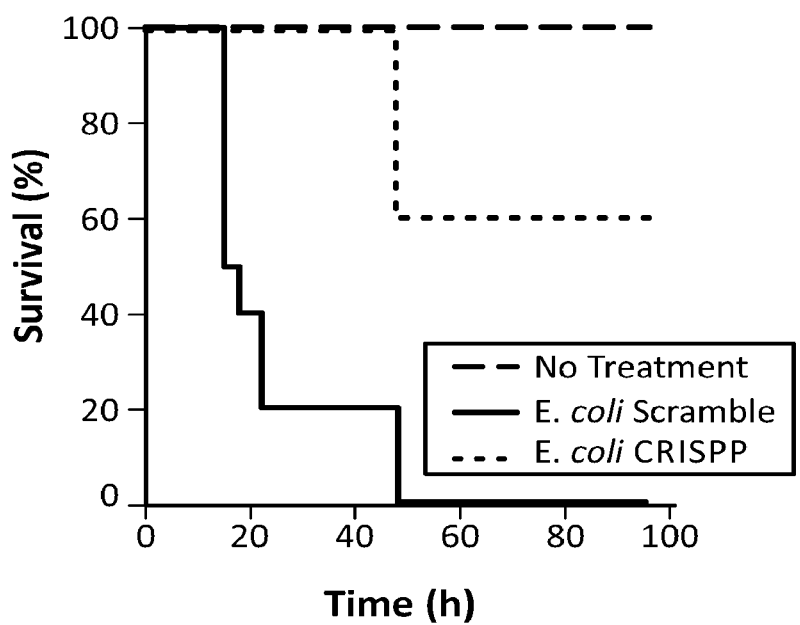
FIG. 10B is a graph tracking survival of outbred Swiss mice in various treatment arms following intraperitoneal injection of E. coli ($4 \times 10^7$ bacteria). As in FIG. 10A, CRISPP-treated mice (10 mcg/kg/dose) received 2 doses intraperitoneally; one given 1 hour prior to infection and one dose given 6 hours after infection. The same dose, delivery route, and schedule were followed for the scrambled peptide control mice. Here, 10 mice were assessed in each group: no treatment, E. coli plus CRISPP, and E. coli plus scrambled peptide. The E. coli plus CRISPP group survival was statistically greater than the E. coli plus scrambled peptide group (p<0.0001).
Figure 11:
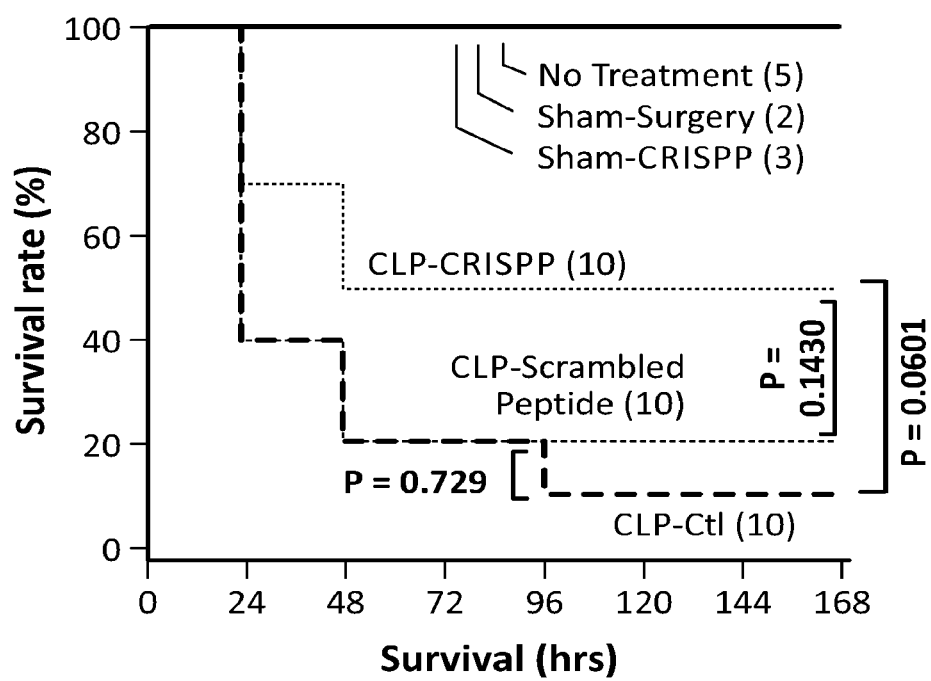
FIG. 11 is a graph tracking survival of outbred Swiss mice in various treatment arms of a murine CL/P model. CRISPP treated mice (10 mcg/kg) received 2 doses intraperitoneally; one given 1 hour prior to surgery or sham surgery and one dose given 6 hours after surgery. The same dose, delivery route, and schedule were followed for the scrambled peptide control mice. Ten mice were assessed in each of the CL/P groups. The CL/P plus CRISPP group survival approached statistical significance compared with the CL/P-control group (p=0.06).
Figure 20:
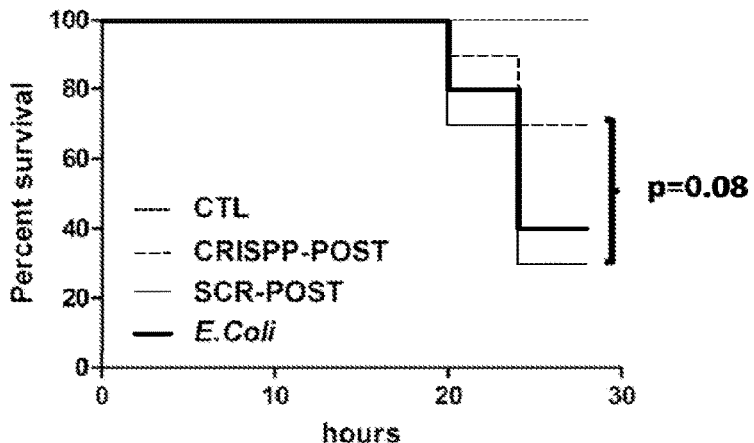
FIG. 20 is a graph depicting an assessment of ten mice in each of four groups: no treatment, *E. coli*, CRISPP-Post/*E. coli*, and SCR-Post/*E. coli*.

Survival of outbred Swiss mice was tracked in various treatment arms following intraperitoneal injection of either LPS (20 mg/kg) or *E. coli* ($4 \times 10^7$ bacteria), as shown in FIGS. 10A and 10B. CRISPP treated mice (10 mcg/kg/dose) received 2 doses intraperitoneally; one given 1 hour prior to infection and one dose given 6 hours after infection. The same dose, delivery route, and schedule were followed for the scrambled control peptide control mice. Six mice were assessed in both groups: LPS+CRISPP and LPS+scrambled control peptide. The LPS+CRISPP group survival was statistically greater than the LPS+scrambled control peptide group (p=0.02). Ten mice were assessed in each group: no treatment, E. coli+CRISPP, and E. coli+scrambled control peptide. No antibiotics were given. No deaths occurred in the no treatment group. The E. coli+CRISPP group survival was statistically greater than the E. coli+scrambled control peptide group (p<0.0001). Referring to FIG. 11, CRISPP was also evaluated in a murine model of polymicrobial infection caused by cecal ligation and puncture (CL/P). CL/P was also performed without concomitant antibiotic treatment. Ten mice were assessed in each of the CL/P groups. The CL/P+CRISPP group survival approached statistical significance compared with the CL/P control group (p=0.06). FIG. 20 is a graph depicting the assessment of ten mice in each of the following groups: no treatment, E. coli, CRISPP-Post/E. coli, and SCR-Post/E. coli. The survival increase seen in CRISPP-Post/E. coli mice compared to SCR-Post/E. coli mice approached statistical significance. For all experiments in each of the three murine models, the Log-rank (Mantel-Cox) statistical tool was used to compare the survival curves between groups and employed the post hoc Bonferroni correction. For all experiments in all three models, * denotes p<0.05,  denotes p<0.01, and * denotes p<0.001.

Example 13—Analyzing NET Formation in CLD Using Human Tissue and a Sheep Model

Figure 12A:
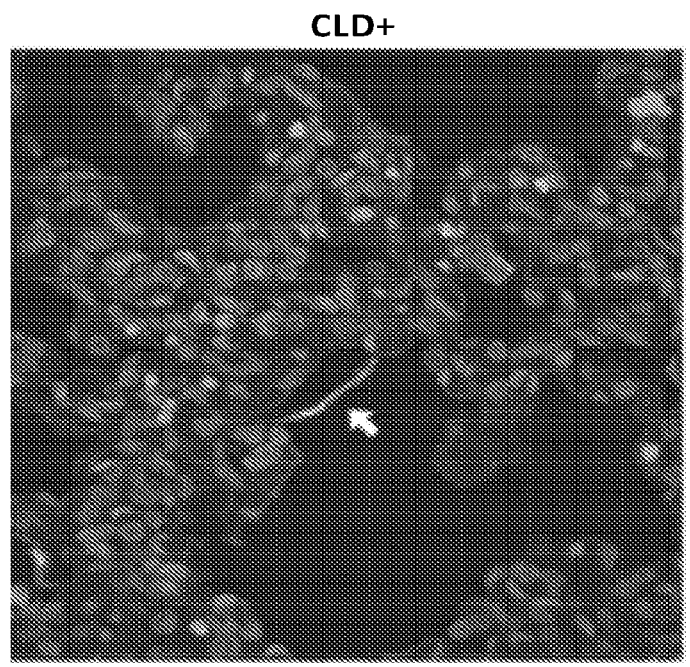
FIG. 12A is an image showing NET formation in paraffin-embedded human lung tissue obtained at autopsy of neonates who died with CLD. Extracellular, alveolar histone $H_3$ accumulation consistent with NET formation is indicated by the white arrow.
Figure 12B:
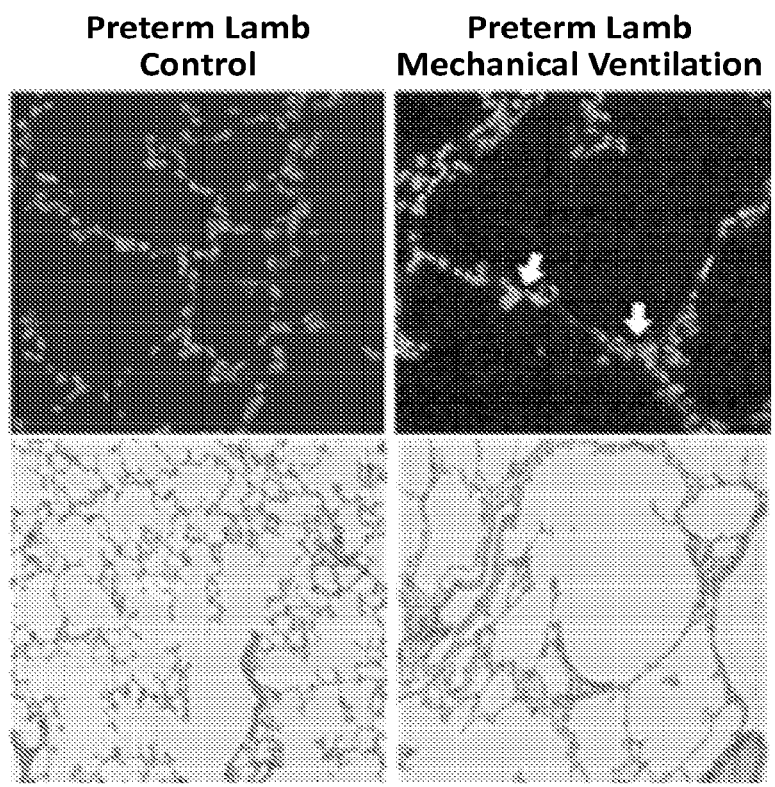
FIG. 12B is a series of images assessing NET formation in paraffin-embedded preterm lamb lung tissue in a sheep model of CLD. Referring to the top two images, extracellular, alveolar NET formation is indicated by the white arrows. Referring to the bottom two images, H&E staining demonstrates other hallmarks of neonatal CLD including hypercellularity and alveolar simplification.

De-identified human lung tissue from preterm infants who died with CLD was immunohistochemically analyzed for extracellular DNA and histone $H_3$, two key indicators of NET formation (see FIGS. 12A and 12B). Using similar techniques, lung tissue samples collected from prematurely born lambs in the sheep model of CLD were also examined. Lung tissue samples from preterm lambs mechanically ventilated for 18-21 days demonstrated all of the hallmarks of CLD while control tissue samples taken from lambs born either at term or prematurely but supported with CPAP alone did not. Lung tissue samples from the mechanically ventilated preterm lambs demonstrated robust NET formation while that from control lambs did not.

NET formation was assessed in paraffin-embedded human lung tissue obtained at autopsy of neonates who died with CLD. In a preliminary analysis, extracellular, alveolar histone $H_3$ accumulation consistent with NET formation was found. NET formation was also assessed in paraffin-embedded preterm lamb lung tissue in the sheep model of CLD. Extracellular, alveolar NET formation was detected in the preterm lamb CLD specimen but not in the control preterm lamb. Similar deposition of NETs has been reported in a murine model of TRALI. Other hallmarks of neonatal CLD in both human and lamb CLD samples, including hypercellularity and alveolar simplification, were also observed.

Example 14—Characterizing NET Formation in Sheep PMNs

Figure 13A:
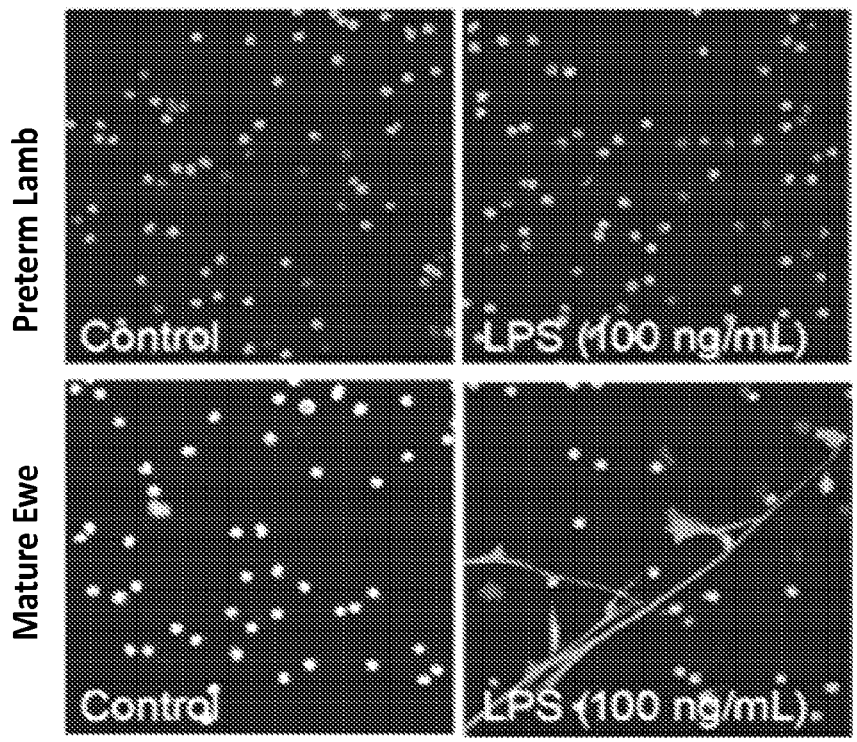
FIG. 13A is a series of images showing PMNs isolated from preterm lamb cord blood and from mature ewes. Control samples, and samples stimulated with LPS (100 ng/mL) for 1 hour are shown, as indicated.
Figure 13B:
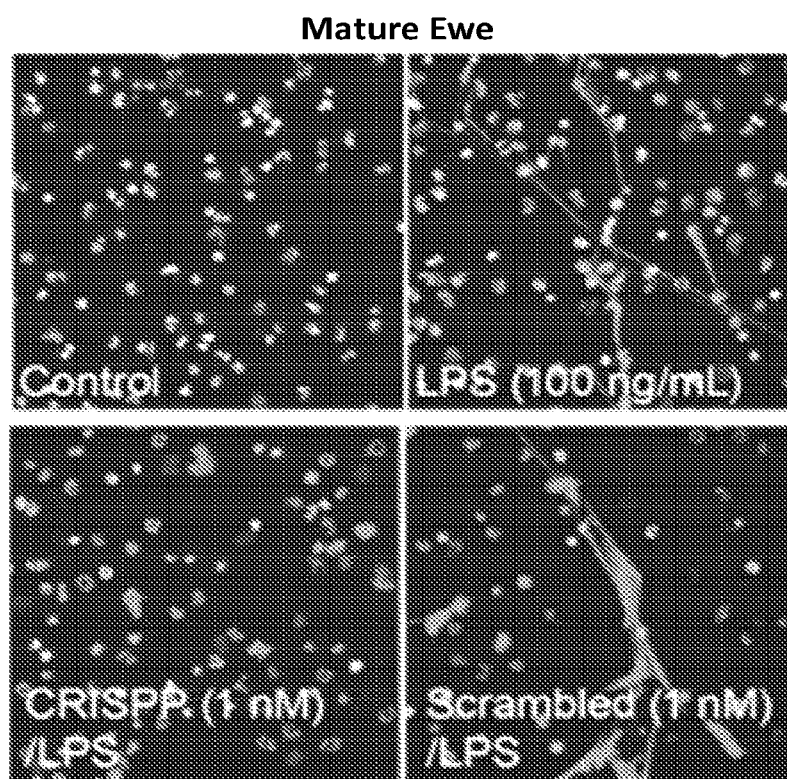
FIG. 13B is a series of images showing mature ewe PMNs pretreated with CRISPP (1 nM) or a scrambled control peptide (1 nM) for 1 hour prior to LPS-stimulation (100 ng/mL), as indicated.

Referring to FIGS. 13A and 13B, PMNs from preterm lamb cord blood and from mature ewes were isolated. The isolated PMNs were stimulated with LPS (100 ng/mL) for 1 hour and NET formation was assessed qualitatively. Mature ewe PMNs were treated with CRISPP (1 nM) or a scrambled control peptide (1 nM) for 1 hour prior to LPS-stimulation (100 ng/mL) and NET formation was assessed qualitatively. PMNs isolated from lamb cord blood failed to form NETs in vitro, but PMNs isolated from mature sheep robustly formed NETs following LPS stimulation. CRISPP pre-treatment of sheep PMNs inhibited NET formation in a dose-dependent manner while the scrambled control peptide did not. CRISPP pre-treatment of sheep PMNs inhibited NET formation stimulated with PMA.

Example 15—Isolating PMNs

PMNs were isolated from acid-citrate-dextrose (ACD) or ethylenediaminetetraacetic acid (EDTA) anticoagulated venous blood of healthy adults, healthy term infants, and prematurely born infants. For the 11 prematurely born infants from whom cord and peripheral blood samples were collected, cord and peripheral blood plasma and PMN preparations were obtained at 5 separate time points throughout the first 2 months of life. PMN suspensions (>96% pure) were prepared by positive immunoselection using anti-CD15-coated microbeads and an auto-MACS cell sorter (MILTENYI BIOTEC, INC.) and were resuspended at $2 \times 10^6$ cells/mL concentration in serum-free M-199 media at 37° C.

Table 1 (below) provides the demographics associated with the preterm infant cohort (n=11).

TABLE 1

| Preterm Infant Demographic Information[1] | |
|---|---|
| Gestational ages at birth | 23⁶/₇-29⁰/₇ weeks |
| Birth weight | 570-1160 g |
| Indication for pre-term delivery | |
| Prolonged premature rupture of membranes or preterm labor | 8 |
| Pregnancy induced hypertension | 1 |
| Placental abruption/preterm labor | 0 |
| Bacterial blood culture results | |
| E. coli | 0 |
| Coagulase (−) Staphlococcus | 2 |
| Group B Streptococcus | 0 |
| Negative | 6 |
| Meningitis | 2 |
| Pneumonia | 2 |
| Antibiotic treatment | All treated, 2-14 d |

[1]Clinical characteristics and infectious complications of preterm infant participants.

It was found that PMNs isolated from newborn infants, whether born at term or prematurely, rapidly gained the ability to form NETs, as demonstrated by qualitative and quantitative assays of NET formation following in vitro stimulation with LPS (see FIGS. 14A and 14B; see also Yost et al., Blood, 2009, 113: 6419-1154; and McInturff et al., Blood, 2012, 120: 3118-3125). Robust NET formation was demonstrated as early as the third day of life even for the most prematurely born infants and NET competency remained intact in PMNs isolated serially through two months of age.

Example 16—Isolating Platelets

Human platelets were isolated as described in Weyrich et al., J Clin Invest, 1996, 97: 1525-1534. Briefly, ACD anticoagulated whole blood was spun at 100×g for 20 minutes. The platelet rich plasma (PRP) was collected, transferred to a new 50 mL conical tube, and prostaglandin E1 (PGE; 100 nM; CAYMAN CHEMICAL) was added. The PRP was then centrifuged at 1500 RPM for 20 minutes. After centrifugation, the supernatant was removed and the platelet pellet was resuspended with 10 mL of 37° C. PSG media and PGE (100 nM). Platelets were resuspended in serum-free M-199 media to 1×10$^8$ cells/mL with platelet counts acquired using a BECKMAN COULTER Particle Counter (BECKMAN COULTER).

Example 17—Live Cell Imaging of NET Formation

It was determined whether nNIF and CRISPP inhibit NET formation by human PMNs using qualitative and quantitative assays of in vitro NET formation. Human PMNs isolated from healthy adult donors were stimulated with LPS (100 ng/mL) or phorbal-12-mystirate (PMA; 20 nM), ±nNIF (1 nM) or CRISPP (1 nM), pre-incubation (1 hour). Scrambled control peptide (SCR) generated using the identical amino acid content as CRISPP but linked in a random order was used as a control. NET formation was assessed 2 hours after stimulation. It was found that both nNIF and CRISPP significantly inhibited NET formation in the in vitro system as compared to the SCR peptide control (see FIGS. 6A and 16A-16D).

Figure 16A:
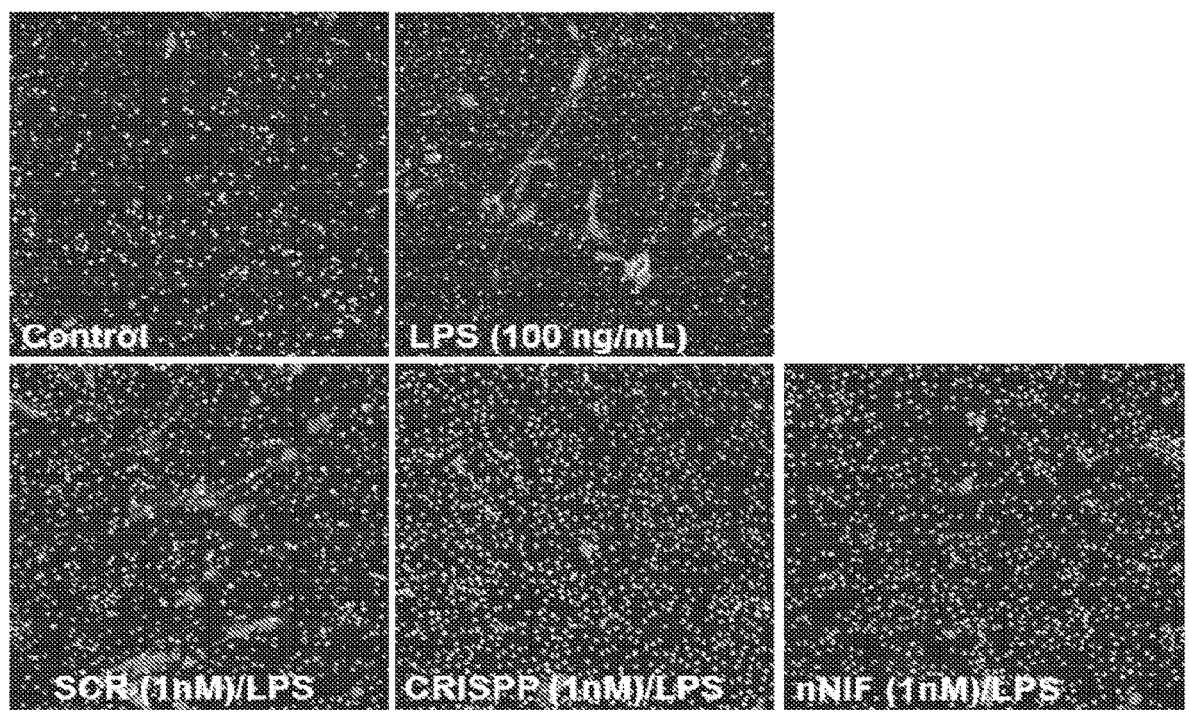
FIG. 16A is a series of images (clockwise from top left) showing NET formation in: control PMNs, LPS-stimulated (100 ng/mL) PMNs, nNIF (1 nM) pre-incubated LPS-stimulated PMNs, CRISPP (1 nM) pre-incubated LPS-stimulated PMNs, and SCR (1 nM) pre-incubated LPS-stimulated PMNs.
Figure 16B:
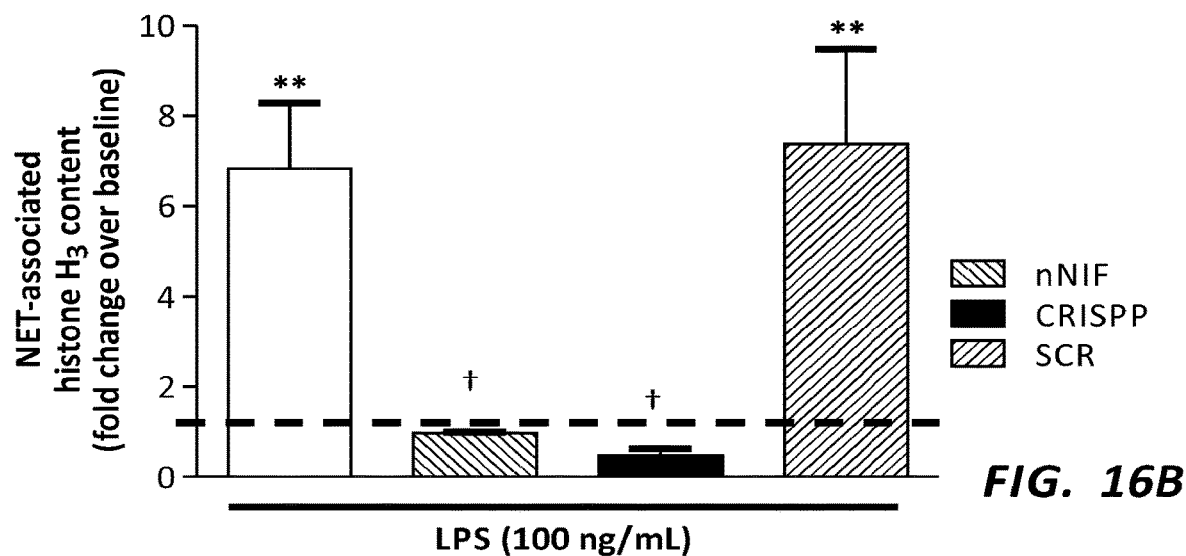
FIG. 16B is a graph depicting extracellular histone $H_3$ content (fold change over baseline) on the y-axis. Data from human PMNs under indicated conditions are represented on the x-axis. The dashed line represents the control values, arbitrarily set at 1. ** denotes $p<0.05$ for LPS and SCR/LPS compared to control, and † denotes $p<0.05$ for CRISPP/LPS and nNIF/LPS compared to both the LPS and SCR/LPS groups.
Figure 16C:
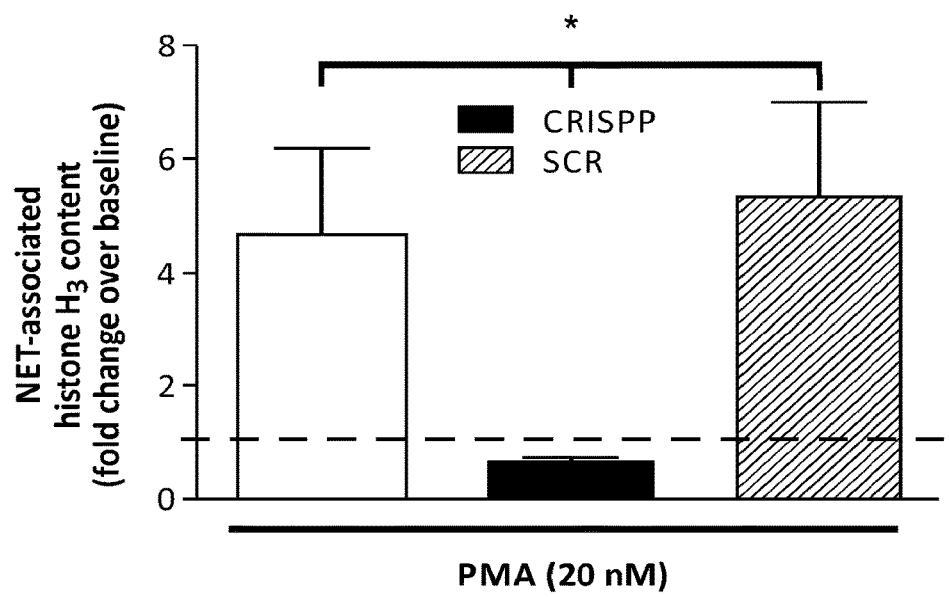
FIG. 16C is a graph depicting extracellular histone $H_3$ content (fold change over baseline) on the y-axis. Data from human PMNs under indicated conditions are represented on the x-axis. The dashed line represents the control values, arbitrarily set at 1. * denotes $p<0.05$ for CRISPP/PMA compared to PMA and SCR/PMA groups.
Figure 16D:
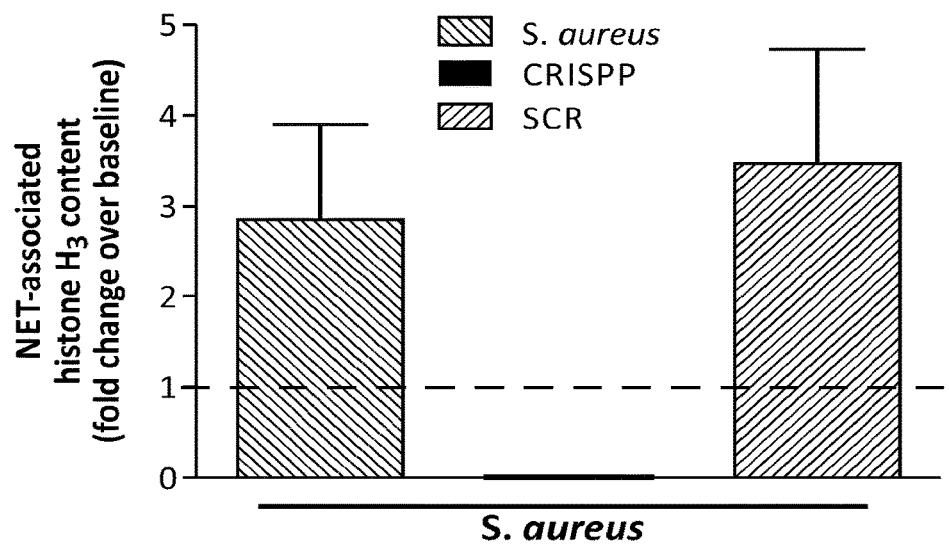
FIG. 16D is a graph showing the results of a human histone $H_3$ release assay to quantify NET formation (n=2). Extracellular histone content (fold change over baseline) is represented on the y-axis. Data from human PMNs stimulated under indicated conditions are represented on the x-axis.

NET formation was assessed by stimulated adult PMNs±nNIF or CRISPP pre-incubation, both qualitatively and quantitatively (see FIGS. 6A and 16A-16D). nNIF or CRISPP pre-incubation (1 nM) for 1 hour prior to stimulation (LPS, 100 ng/mL or PMA, 20 nM) inhibited NET formation, while pretreatment with SCR (1 nM) did not appear to inhibit NET formation. The representative images of FIG. 16A (20× magnification) and FIG. 6A (60× magnification) show extracellular NET-associated DNA and nuclear DNA. The human histone $H_3$ release assay was used to quantify NET formation in stimulated PMNs pre-incubated±nNIF or CRISPP. As depicted in FIGS. 16B and 16C, extracellular histone content (fold change over baseline) is represented on the y-axis, and the dashed line represents the control values, arbitrarily set at 1. The data presented are representative of 3 separate experiments performed using PMNs isolated from 3 different participants. * denotes p<0.05 for CRISPP/PMA compared to PMA and SCR/PMA groups, ** denotes p<0.05 for LPS and SCR/LPS compared to control, while † denotes p<0.05 for CRISPP/LPS and nNIF/LPS compared to both the LPS and SCR/LPS groups. The one-way ANOVA statistical tool with Tukey's post-hoc testing was employed.

Figure 17D:
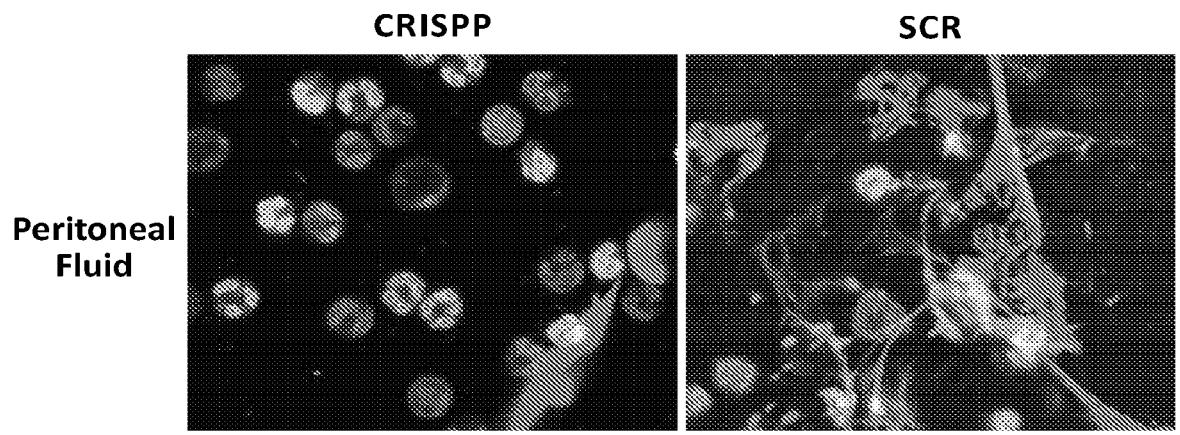
FIG. 17D are images depicting NET formation in peritoneal fluid following *E. coli* injection±pre-injection of CRISPP (10 mg/kg) or SCR (10 mg/kg), as indicated.
Figure 17E:
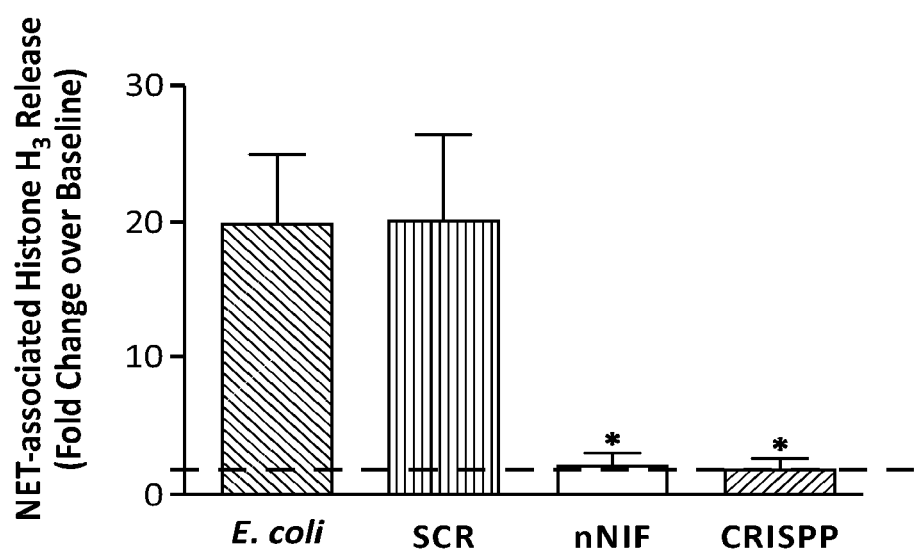
FIG. 17E is a graph depicting histone $H_3$ release to assess NET formation. Extracellular histone content (fold change over baseline) is represented on the y-axis. The dashed line represents the control values, arbitrarily set at 1. * denotes $p<0.05$ for CRISPP/*E. coli* and nNIF/*E. coli* groups compared to *E. coli* and SCR/*E. coli* groups.
Figure 17F:
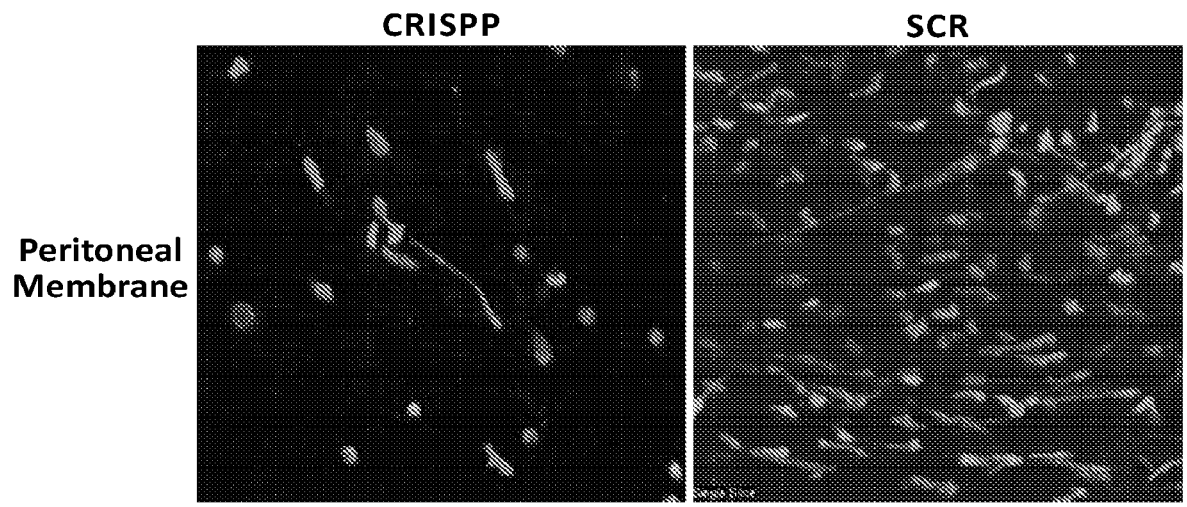
FIG. 17F are images depicting NET formation on peritoneal tissue following *E. coli* injection±pre-injection of CRISPP (10 mg/kg) or SCR (10 mg/kg), as indicated.
Figure 17G:
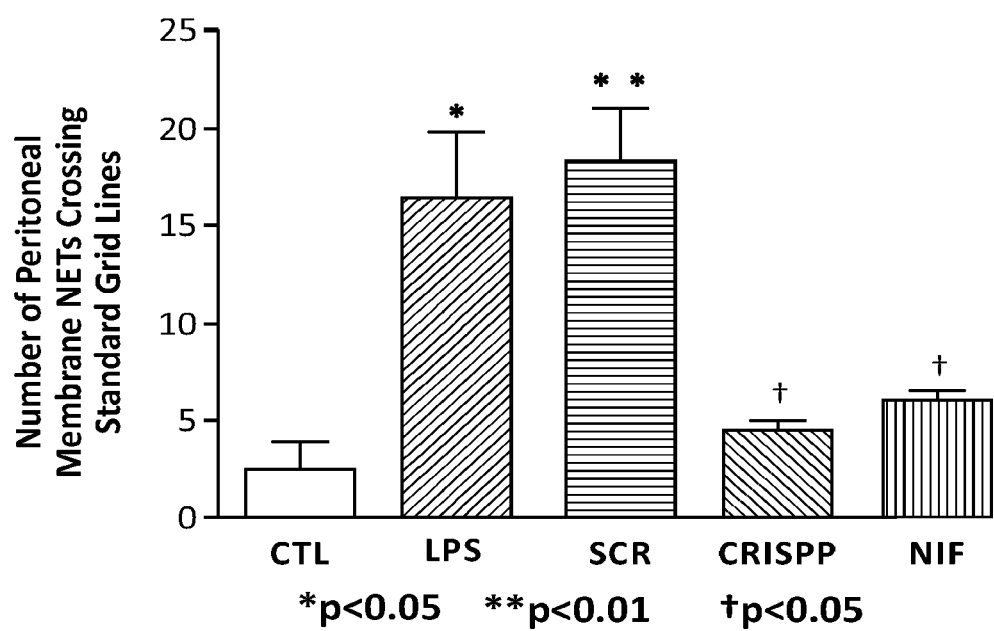
FIG. 17G is a graph depicting quantitation of NET formation using IMAGEJ software and a standardized grid in 5 randomly selected visual fields for each sample on confocal microscopy. The graph represents the number of NETs crossing the standardized grid lines shown on the y-axis and the experimental groups shown on the x-axis. * denotes $p<0.05$ for LPS v. Control, ** denotes $p<0.01$ for SCR/LPS group v. Control, and † denotes $p<0.05$ for CRISPP/LPS and nNIF/LPS groups v. SCR/LPS.

NET formation was assessed in the peritoneum using live cell imaging. A cell impermeable DNA dye stained all extracellular DNA, and a cell permeable DNA dye served as a nuclear counterstain. A qualitative decrease in NET formation in the peritoneal fluid of nNIF or CRISPP pretreated mice was found compared to the SCR control and a significant quantitative decrease in NET formation as assayed by histone $H_3$ release assay of the peritoneal fluid (see FIGS. 17D and 17E). NET formation was also examined on freshly resected peritoneal membrane tissue using live cell imaging. A qualitative and quantitative decrease in peritoneal membrane-associated NET formation was seen (see FIGS. 17F and 17G). These results demonstrate that nNIF and the NRP CRISPP can inhibit NET formation stimulated in in vivo as well as in vitro model systems.

The ability of CRISPP to inhibit NET formation induced by bacterial and viral pathogens was also tested. CRISPP inhibited NET formation induced by incubation with S. aureus bacteria (MOI 100) and Dengue viral infection (MOI 0.05) (see FIGS. 7A, 8A, and 8B; see also Example 18) demonstrating that nNIF can inhibit NET formation in reductionist experimental models of bacterial and viral infection.

Qualitative assessment of NET formation was performed as previously referenced in Yost et al., Blood, 2009, 113: 6419-6427 and McInturff et al., Blood, 2012, 120: 3118-3125. Briefly, primary PMNs isolated from preterm infants, healthy term infants, and healthy adults (2×10$^6$ cells/mL) were incubated with control buffer or stimulated with LPS (100 ng/mL), PMA (20 nM), or S. aureus bacteria (MOI 100) for 1 hour at 37° C. in 5% $CO_2$/95% air on glass coverslips coated with poly-L-lysine. For selected experiments, primary PMNs were pre-incubated with autologous plasma, cord blood plasma, nNIF (1 nM), CRISPP (1 nM), or SCR (1 nM) for 1 hour prior to imaging. After pre-incubation and/or stimulation, PMNs were gently washed with PBS and incubated with a mixture of cell permeable (SYTO Green, MOLECULAR PROBES) and impermeable (SYTOX Orange, MOLECULAR PROBES) DNA fluorescent dyes. Confocal microscopy was accomplished using a FV300 1×81 Microscope and FLUOVIEW software (OLYMPUS). Both 20× and 60× objectives were used. Z-series images were obtained at a step size 1 μm over a range of 20 μm for each field. OLYMPUS FLUOVIEW and ADOBE PHOTOSHOP CS2 software were used for image processing.

Example 18—Imaging of Dengue Virus-Induced NET Formation

Primary PMNs isolated from healthy adults (2×10$^6$ cells/mL) were incubated with mock infection buffer or live dengue virus (MOI 0.05), as for the live cell imaging discussed above. After a 1 hour incubation, the infected PMNs were fixed with 2% p-FA for 10 minutes prior to incubation with fluorescently-labeled, cell permeable and cell impermeable DNA dyes, and imaged as for live cell imaging using confocal microscopy.

Example 19—Quantitating NET Formation and Supernatant Histone $H_3$ Content

Supernatant total histone $H_3$ content was determined as previously referenced in McInturff et al., Blood, 2012, 120: 3118-3125. After live cell imaging of control and stimulated primary PMNs (2×10$^6$/mL; various agonists), the cells were incubated with PBS containing DNase (40 U/mL) for 15 minutes at room temperature to break down and release NETs formed in response to stimulation. The supernatant was gently removed and centrifuged at 420×g for 5 minutes. The cell-free supernatant was then mixed 1:3 with 4× Laemmli buffer prior to western blotting. A polyclonal primary antibody against human histone $H_3$ protein (CELL SIGNALING TECHNOLOGY) and infrared secondary antibodies (LI-COR BIOSCIENCES) were used. Imaging and densitometry were performed on the ODYSSEY™ infrared imaging system (LI-COR BIOSCIENCES).

Example 20—Isolating and Identifying nNIF in Umbilical Cord Blood Plasma

Two plasma samples from a single preterm infant, one from the umbilical cord blood, and one from a peripheral blood sample taken on day of life 28, underwent abundant plasma protein removal (PROTEOSPIN, NORGEN) prior to 2D-electrophoresis using separation first by isoelectric focusing (pH range 3-8) and then by size (TGX PRECAST GEL, BIORAD). The resulting gels were compared for differential protein content. Six differentially expressed protein clusters were analyzed. Following trypsin digestion and tandem mass spectrometry using an LTQ-FT ion-trap/FTMS hybrid mass spectrometer (THERMOELECTRON), candidate proteins/peptides were identified as potential NET-inhibitory substances.

Example 21—Affinity Purifying nNIF

Figure 15C:
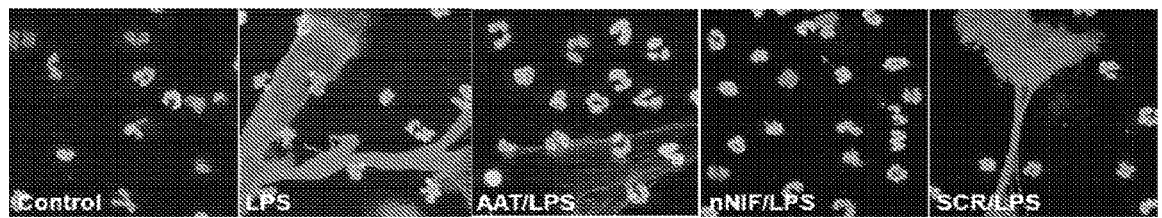
FIG. 15C is a series of images (left to right) showing adult human PMN NET formation in: control PMNs, LPS-stimulated PMNs, AAT pre-incubated LPS-stimulated PMNs, nNIF pre-incubated LPS-stimulated PMNs, and scrambled control peptide (SCR) pre-incubated LPS-stimulated PMNs.

To determine whether the 29 amino acid peptide identified in Example 5 were the substances circulating in umbilical cord blood responsible for the inhibition of NET formation, cord blood plasma was depleted of nNIF via affinity purification using the carboxy-terminus AAT antibody. nNIF was then eluted from the column and used in experiments to assess the NET-inhibitory activity of unaltered cord blood plasma, nNIF-depleted cord blood plasma, and affinity purified nNIF from cord blood plasma. As a control, recombinant AAT in nNIF-depleted cord blood was also assessed (see FIGS. 5A-5F). PMNs isolated from healthy adult donors responded with robust NET formation following 2 hour incubation with LPS (100 ng/mL). Pre-incubation with unaltered cord blood plasma inhibited in vitro NET formation, consistent with earlier results (see FIGS. 3B and 14C). Pre-incubation with nNIF-depleted cord blood plasma±rAAT (1 nM) did not. Pre-incubation with affinity purified nNIF, however, inhibited NET formation by LPS-stimulated PMNs to a similar degree as the unaltered umbilical cord blood. Further experiments also showed that full-length, enzymatically active human AAT failed to inhibit NET formation by PMNs isolated from healthy adult donors while nNIF did (see FIG. 15C). These results suggested that the 29 amino acid peptides nNIF and CRISPP detected in umbilical cord blood have NET-inhibitory activity. Synthesis of nNIF and CRISPP for in vitro studies of their NET inhibitory capacities was then performed.

As discussed above, following abundant plasma protein removal (PROTEOSPIN, NORGEN), a polyclonal antibody raised against the last 18 amino acids of the carboxy terminus of full length AAT (LIFESPAN BIOSCIENCES) was used to affinity purify nNIF from cord blood plasma using an immunoprecipitation kit (THERMO SCIENTIFIC). Cord blood plasma depleted of both nNIF and full length AAT was collected as were the peptides captured by affinity purification for use in in vitro assays of NET formation. Full length, enzymatically active AAT (SIGMA) was also resuspended in elution buffer and tested in parallel.

Example 22—Analyzing Peritoneal Fluid and Membranes

Animals were treated with CRISPP (10 mg/kg), nNIF (10 mg/kg), or SCR (10 mg/kg) by i.p. injection 1 hour prior to infection (*E. coli*, 4.5×10$^7$ cfu/mouse, i.p. injection) or stimulation (LPS, 25 mg/kg, i.p. injection (SIGMA)). Control mice were injected with saline alone. The mice were sacrificed in a $CO_2$ chamber 3 hours post-infection/stimulation with the peritoneal contents harvested and analyzed. Briefly, the skin of the abdomen was cut open in the midline after thorough disinfection and without injuring the muscle. The peritoneal cavity was lavaged with sterile saline solution (100 mL) and analyzed for in vivo NET formation, bacteriology, and leukocyte accumulation. NETs in the peritoneal fluid were qualitatively and quantitatively analyzed using live cell imaging with confocal microscopy and histone release assays. NETs on the inner surface of the peritoneal membrane were assessed quantitatively using live cell imaging followed by standardized grid analysis of 5 randomly selected high power visual fields per tissue sample (IMAGE-J software, NIH). Peritoneal bacterial colony forming units (cfu) counts were quantified by permeabilizing all recovered leukocytes with 0.1% Triton-X 100 for 10 minutes and performing serial dilutions and bacterial cultures on 5% sheep blood agar plates (HARDY DIAGNOSTICS). After a 24-hour incubation, bacterial counts were determined. Total leukocyte counts in the peritoneal lavage were determined in Neubauer chambers using an optical microscope after dilution in Turk's solution (2% acetic acid). Differential leukocyte analysis was performed using a 60× oil immersion objective to assess morphology of cytocentrifuged cells stained with May-Grunwald-Giemsa dye.

Example 23—Assaying Chemotaxis

Figure 18A:
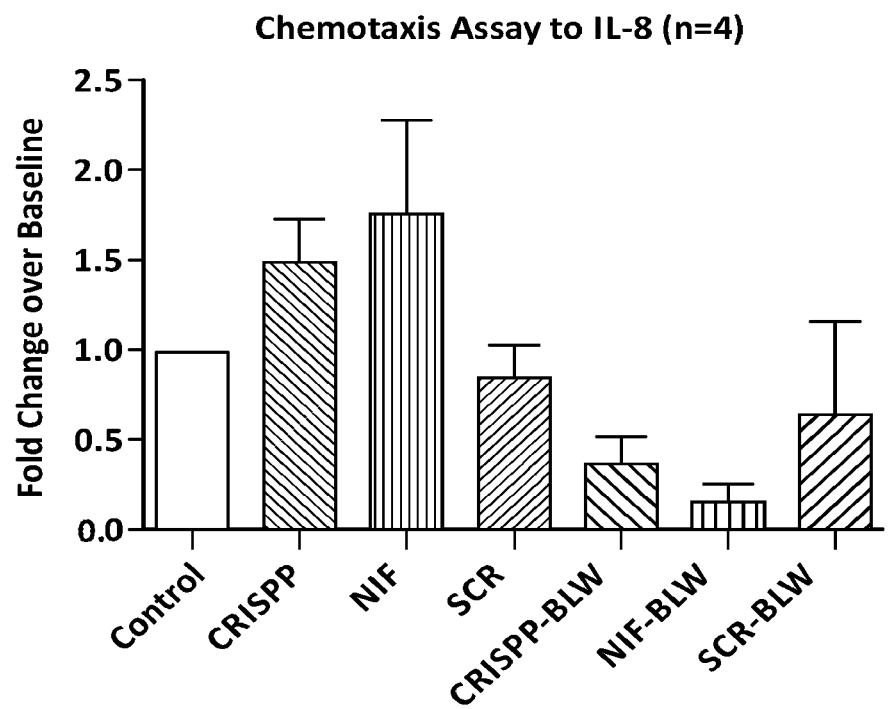
FIG. 18A is a graph depicting chemotaxis induced by IL-8 (2 ng/mL) for PMNs isolated from healthy adults following treatment±nNIF, CRISPP, or SCR peptide control, as indicated. The ability of nNIF and CRISPP to induce chemotaxis on their own was also measured (CRISPP-BLW, NIF-BLW, and SCR-BLW columns). The y-axis shows fold change over baseline of PMN chemotaxis±standard error of the mean (SEM).
Figure 18B:
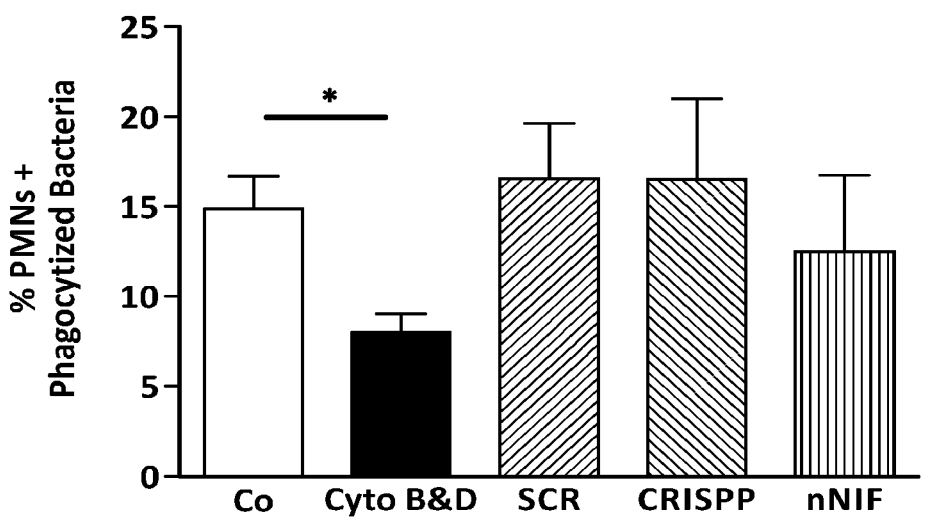
FIG. 18B is a graph depicting phagocytosis by PMNs isolated from healthy adults following a four hour incubation with fluorescently labelled *E. coli* BIOPARTICLES ($6×10^6$ particles/mL). The y-axis depicts the percent of PMNs positive for intracellular *E. coli*±SEM as assessed via confocal microscopy with multi-plane assessment. Cytochalasin B and D (10 µM) pretreatment was used as a control for phagocytosis inhibition. * denotes $p<0.05$.
Figure 18C:
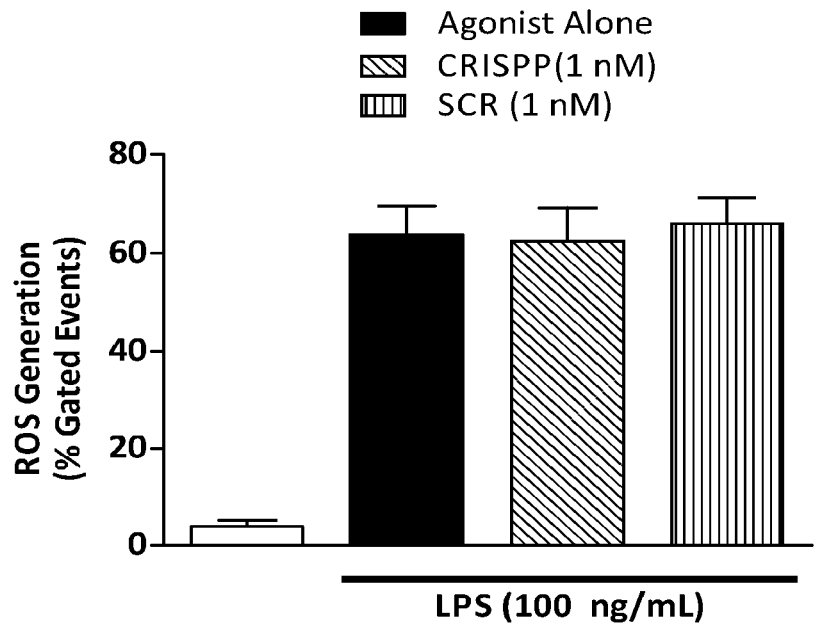
FIG. 18C is a graph depicting respiratory burst activity in LPS-stimulated PMNs (100 ng/mL)±pre-incubation for 1 hour with CRISPP (1 nM) or SCR (1 nM). ROS generation was measured using a dihydrorhodamine assay. The columns indicate ROS generation shown as percent gated events±SEM.

Potential CRISPP-mediated effects on key neutrophil activities besides NET formation were assessed: chemotaxis, phagocytosis, reactive oxygen species generation, and bacterial killing. It was found that nNIF and CRISPP did not significantly inhibit PMN chemotaxis, phagocytosis, or reactive oxygen species generation (see FIGS. 18A-18C). Total, phagocytotic, and NET-mediated bacterial killing of a pathogenic strain of *E. coli* was also assessed. It was found that while CRISPP pre-incubation of LPS-stimulated PMNs significantly decreased total and NET-mediated extracellular bacterial killing in comparison to control PMNs, the phagocytotic component of bacterial killing was not different between the three groups (see FIG. 18D).

Chemotaxis by PMNs isolated from healthy adult donors was assessed using a modified Boyden Chamber assay±a one hour pre-incubation with nNIF (1 nM), CRISPP (1 nM), or SCR (1 nM). Recombinant human IL-8 (2 ng/mL) was used as the chemoattractant. Chemotaxis through a 5 micron filter was determined by counting PMNs in 10 randomly selected high-power fields as previously described in Hill et al., Lancet, 1974, 2: 617-619. In separate experiments, nNIF, CRISPP, or SCR (all at 1 nM) were evaluated for chemoattractant activity using the same system.

Example 24—Assaying Phagocytosis

As discussed above, it was found that nNIF and CRISPP did not significantly inhibit phagocytosis activity in neutrophils. PMNs were isolated from blood of healthy adult donors and resuspended in M-199 at a concentration of 2×10$^6$ cells/mL. Leukocytes were pre-incubated for 60 minutes under standard conditions with cytochalasin B and D (10 μM), nNIF (1 nM), CRISPP (1 nM), or SCR (1 nM). Following pre-incubation, PMNs were incubated with 6×10$^6$ *E. coli* BIOPARTICLES (E-13231, MOLECULAR PROBES) on a rotator for 4 hours under standard conditions. The PMNs were then washed and resuspended in the starting volume in M-199 before being spun down onto glass coverslips and fixed with 2% paraformaldehyde for 10 minutes and permeabilized with 0.1% Triton-X-100 for 10 minutes. Leukocytes were stained with WGA 555 (INVITROGEN) and TOPRO-3 (MOLECULAR PROBES) and randomly selected high power visual field images were captured using confocal microscopy. IMAGE-J software (NIH) was used to determine the percentage of PMNs that were positive for fluorescently labeled *E. coli* BIOPARTICLES detected at 488 nm.

Example 25—Assaying Reactive Oxygen Species Generation

Also, as discussed above, it was found that nNIF and CRISPP did not significantly inhibit ROS generation activity in neutrophils. Human PMNs isolated from healthy adult whole blood were resuspended to a concentration of $2\times10^6$ cells/mL in M-199 media and pre-incubated±CRISPP (1 nM) or SCR (1 nM) peptide for 1 hour under standard conditions. The PMNs were then stimulated with LPS (100 ng/mL) for 1 hour, washed, and resuspended with a dihydrorhodamine (7.25 mM; D-632, MOLECULAR PROBES) and catalase (1000 Units/mL; C-40, SIGMA) mixture and incubated at 37° C. for 10 minutes. After incubation, samples were placed at 4° C. and analyzed for ROS-dependent fluorescence using a BECTON-DICKINSON FACSCAN device equipped with CELLQUEST software.

Example 26—Assaying Platelet Activation

Figure 21A:
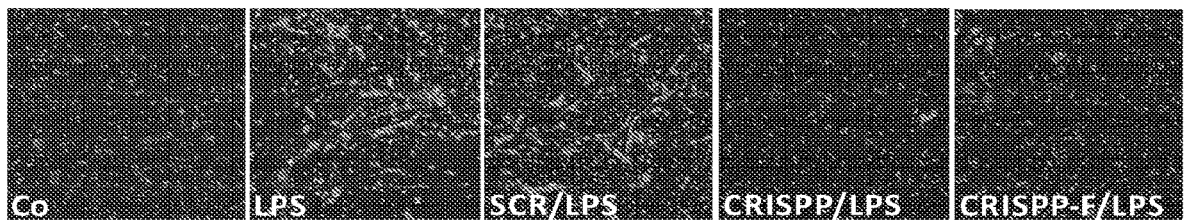
FIG. 21A is a series of images showing NET formation following LPS-stimulation±pretreatment with CRISPP, CRISPP-F, or SCR-F, as indicated.
Figure 21B:
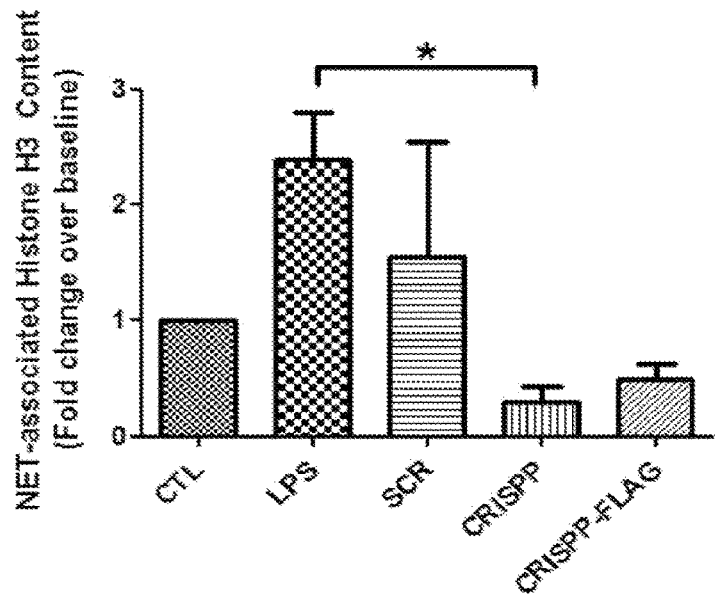
FIG. 21B is a graph showing the results of a histone $H_3$ release assay to quantify NET formation in response to LPS stimulation following pre-incubation with SCR, CRISPP, or CRISPP-FLAG. Extracellular histone content (fold change over baseline±SEM) is represented on the y-axis. * denotes $p<0.05$.

Platelets reportedly play a role in regulating NET formation by human PMNs (see Clark et al., Nat Med, 2007, 13: 463-469). It was determined whether CRISPP alters platelet activation and platelet-PMN interactions. P-selectin expression was determined by platelets pre-incubated with CRISPP and SCR peptides followed by stimulation with thrombin. It was found that CRISPP and SCR peptides did not alter platelet p-selectin expression when given alone or following thrombin stimulation (see FIG. 18E). Furthermore, in experiments where LPS-stimulated PMNs were mixed with thrombin-stimulated platelets isolated from the same donor, CRISPP and SCR did not alter platelet/PMN association as assessed via flow cytometry (see FIG. 18F). To further assess whether platelets take up CRISPP from the inflammatory milieu, CRISPP and SCR peptides were synthesized with a FLAG tag motif added to the carboxy terminus of each peptide (CRISPP-F, SCR-F). It was then demonstrated that the CRISPP-F maintains NET-inhibitory activity similar to that of un-tagged CRISPP (see FIGS. 21A and 21B), and immunocytochemical experiments were performed with freshly isolated human platelets to determine whether platelets take up CRISPP-F from the inflammatory milieu. It was found that platelets do not take CRISPP-F or SCR-F into their cytoplasm (see FIG. 18G) while PMNs co-incubated with platelets do. This may suggest that the NET inhibitory effects of nNIF and CRISPP do not result from alterations in platelet activation or signaling to trigger NET formation by PMNs.

Using protocols modified from van Velzen, et al., Thromb Res, 2012, 130: 92-98, human platelets ($1\times10^8$ cells/mL) were incubated with CRISPP or SCR (0.1-10 ng/ml) for 1 hour followed by stimulation with thrombin (0.1 IU/mL) or control M-199 media for 15 minutes. The cells were prepared for FACS analysis with the following primary, monoclonal antibodies for 20 minutes: PE-conjugated CD41a (platelet-specific marker) and FITC-conjugated CD62P (P-selectin). Isotype and fluorochrome matched control antibodies were used. After incubation at room temperature in the dark, the cells were lysed with FACS lysis buffer and analyzed by flow cytometry (BECTON-DICKINSON FACSCAN, CELLQUEST software).

Example 27—Assaying Platelet/PMN Aggregation

Using protocols modified from Saboor et al., Malays J Med Sci, 2013, 20: 62-66, human PMNs ($2\times10^6$ cells/mL) were isolated and incubated with CRISPP or SCR (0.1-10 ng/ml) for 1 hour prior to addition of freshly isolated human platelet at a ratio of 100:1 for another 15 minute incubation. After this period, the cells (PMNs and platelets) were stimulated with thrombin (0.1 IU/mL) or control M-199 media for 1 hour. The cells were stained for 20 minutes with the following primary monoclonal antibodies: PE-conjugated CD41 and FITC-conjugated CD16. Isotype and fluorochrome matched control antibodies were used. Flow cytometry was performed using BECTON-DICKINSON FACSCAN and CELLQUEST software.

Example 28—Assaying Nuclear Decondensation

Figure 18G:
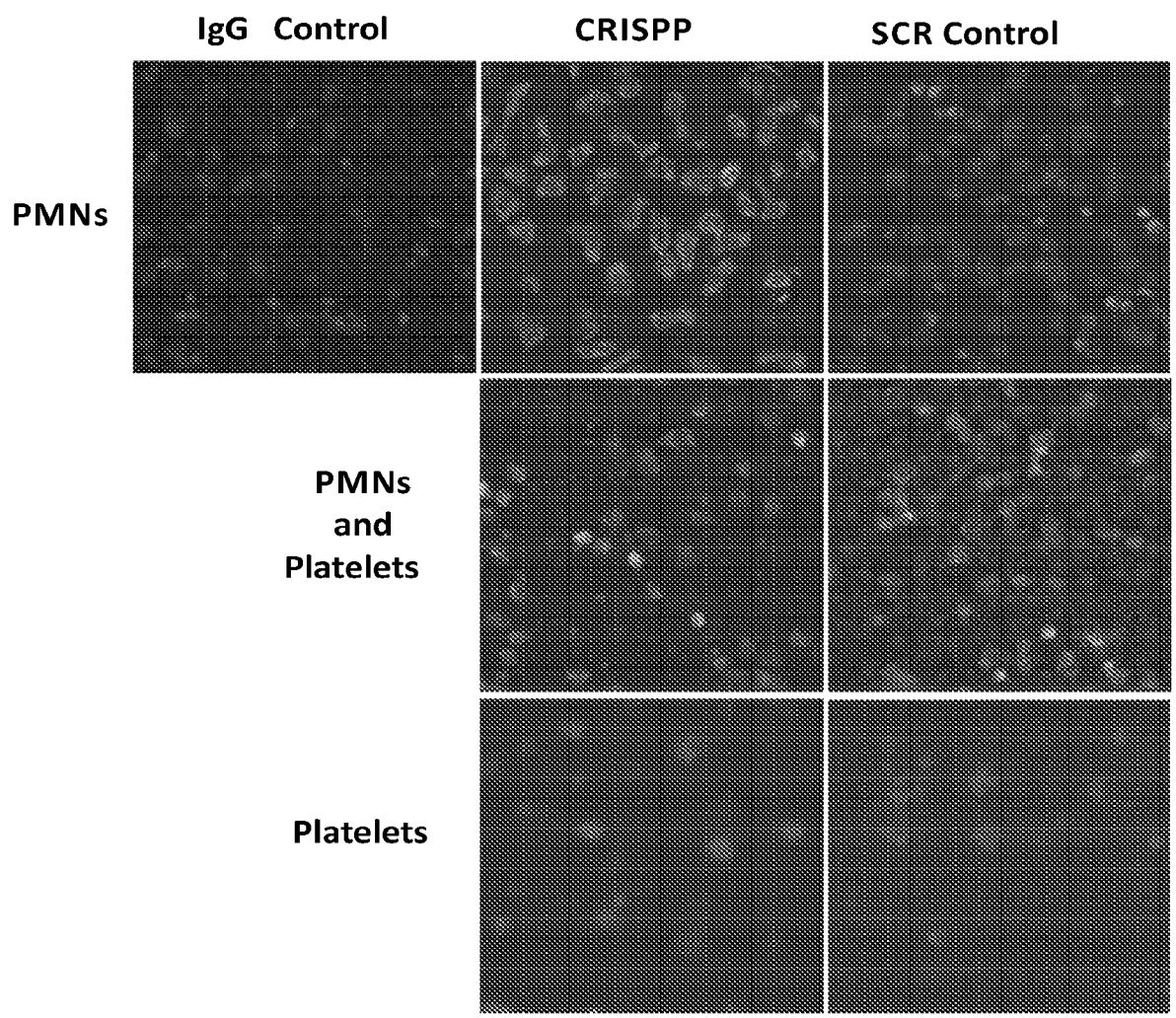
FIG. 18G is a series of images depicting CRISPP-FLAG Tagged (1 nM) and SCR-FLAG Tagged (1 nM) uptake by PMNs, co-incubated platelets and PMNs, and platelets, as indicated.
Figure 19A:
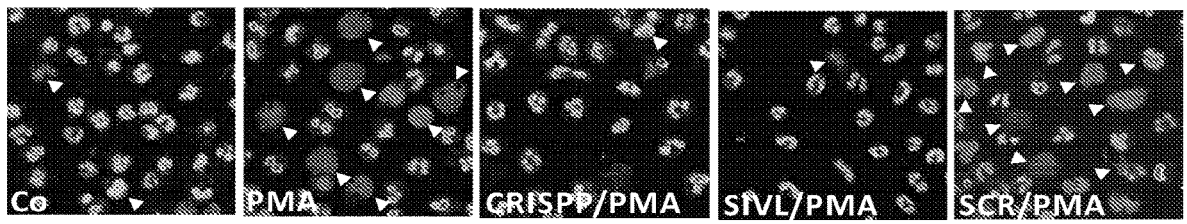
FIG. 19A is a series of images depicting the nuclear area of PMNs pre-incubated with CRISPP (1 nM), SCR (1 nM), or Sivelestat (200 nM) prior to stimulation with PMA (20 nM), as indicated. White arrowheads highlight decondensed nuclei.
Figure 19B:
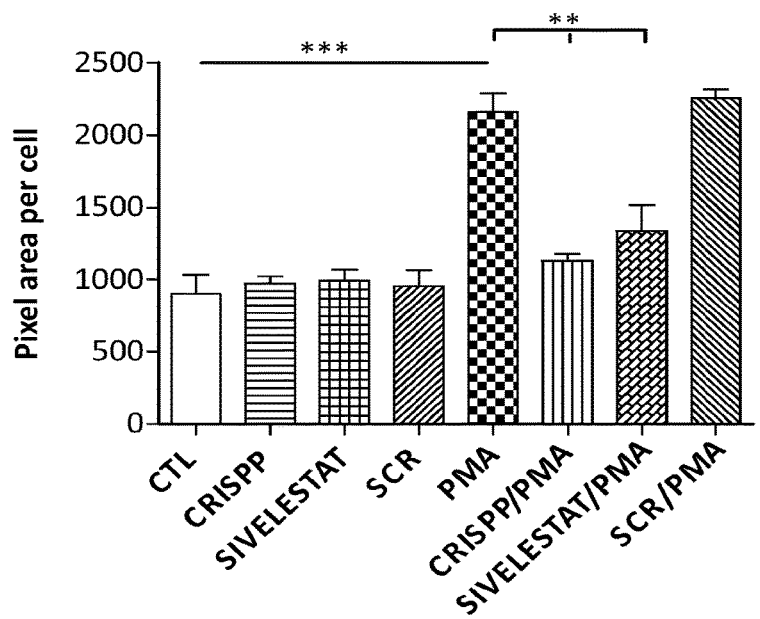
FIG. 19B is a graph quantifying the results of the assays depicted in FIG. 19A.  denotes $p<0.01$ and * denotes $p<0.001$.
Figure 19C:
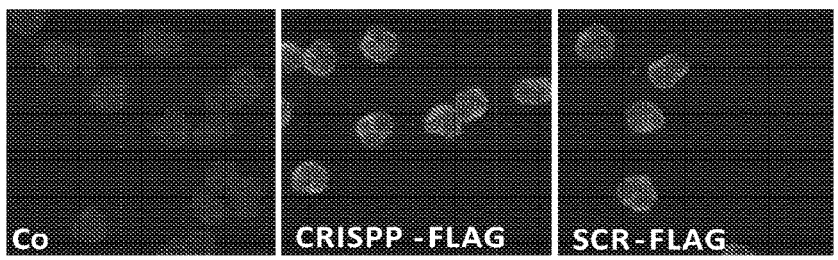
FIG. 19C is a series of images showing FLAG-tagged CRISPP and SCR peptide cellular localization, as indicated.
Figure 19D:
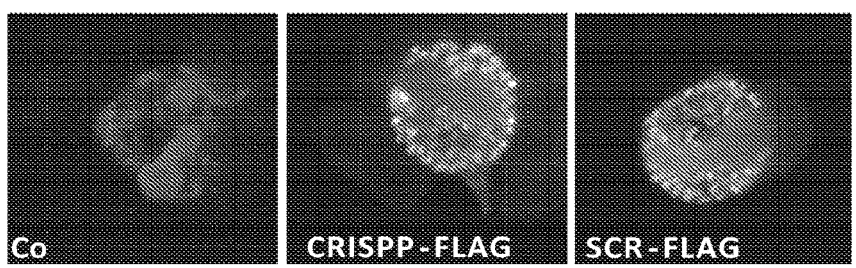
FIG. 19D is a series of images depicting neutrophil elastase and CRISPP-F peptide co-localization. The control image (Co) depicts PMNs treated with both antibodies but without FLAG-tagged peptide treatment.

A possible mechanism by which nNIF and CRISPP inhibit NET formation was ascertained. Using techniques modified from Papayannopoulos et al., J Cell Biol, 2010, 191: 677-691, nuclear area assays were used for PMA-stimulated PMNs as a surrogate for NET formation. PMNs were stimulated with PMA (20 nM) for 2 hours and then visualized via live cell imaging with a cell permeable DNA dye. Images from 5 randomly selected high power fields were captured and the nuclear area of all PMNs on each visual field was quantitated using IMAGEJ software. Nuclear areas were compared for PMNs stimulated with PMA with PMNs pre-incubated with CRISPP (1 nM), SCR (1 nM), or the NE inhibitor Sivelestat (200 nM). Qualitative and quantitative results of these assays demonstrated a significant increase in nuclear area for PMA-stimulated PMNs as compared to control PMNs or PMNs pre-incubated with each of the three reagents but without PMA (see FIG. 19A). Pre-incubation of PMA-stimulated PMNs with CRISPP and Sivelestat, however, resulted in a significant decrease in nuclear area compared to PMA alone while no change was seen in the SCR group (see FIGS. 19A and 19B). Next, immunocytochemical experiments designed to see whether CRISPP is taken up by human PMNs were performed. The CRISPP-F and SCR-F peptides and FLAG-tag specific primary antibodies were used to assess cellular location. It was found that CRISPP-F and SCR-F are taken up into the cytoplasm by PMNs during a one hour incubation (see FIGS. 18G and 19C). No evidence was found of nuclear translocation of CRISPP-F or SCR-F (see FIGS. 18G, 19C, and 19D). These results may suggest that NRPs rapidly enter PMNs but not platelets (see FIGS. 18G, 19C, and 19D), and that uptake of NRPs by PMNs is a function of size and may not be dependent on amino acid sequence or specific receptor-mediated transport. Furthermore, protein co-localization assays using the DUOLINK protein proximity assay (see Carlo et al., FASEB J, 2013, 27: 2733-2741) and primary antibodies targeting F-CRISPP and NE, demonstrate that F-CRISPP and NE can co-localize within 40 nm of each other following CRISPP incubation for 1 hour (see FIG. 19D). CRISPP can inhibit nuclear chromatin decondensation, which is consistent with the selective inhibition of NET formation by CRISPP and nNIF. This process may involve inhibition of NE activity.

PMNs were isolated and resuspended to $2\times10^6$ cells/mL in M-199 media. They were pre-incubated with CRISPP (1 nM), SCR (1 nM), or the neutrophil elastase inhibitor Sivelestat (100 µM) under standard conditions. Under the same conditions, cells were treated±PMA (20 nM) on poly-L-Lysine coated glass coverslips for 2 hours. 5 randomly selected high power visual fields per sample were captured via confocal microscopy and analyzed for nuclear area using the cell-permeable, fluorescent DNA dye SYTO Green. The nuclear pixel areas of >100 individual cells per high power field were determined using IMAGE-J software (NIH).

Example 29—Determining CRISPP Peptide Cellular Localization

The cellular locations of FLAG-tagged CRISPP (F-CRISPP) and FLAG-tagged SCR (F-SCR) peptides were determined using immunocytochemistry. Adult neutrophils were pre-incubated with either F-CRISPP (1 nM) or F-SCR (1 nM) for 1 hour under standard conditions followed by stimulation with LPS (100 ng/mL) for 2 hours. The PMNs were then spun down onto glass coverslips with 2% p-FA fixation and 0.1% Triton-X-100 permeabilization. FLAG-tagged peptide was detected using a monoclonal anti-FLAG antibody (F1804, SIGMA) with TOPRO-3 as a nuclear counterstain.

Example 30—Using a DUOLINK Protein Proximity Assay

The DUOLINK Protein Proximity Assay (SIGMA) was used to determine whether CRISPP and NE co-localize within PMNs isolated from healthy adults. PMNs were isolated and pre-incubated for 1 hour with F-CRISPP (10 nM) or F-SCR (10 nM) under standard conditions prior to stimulation with LPS (100 ng/mL) on poly-L-lysine coated glass coverslips. The DUOLINK Protein Proximity Assay was performed using a rabbit anti-neutrophil elastase antibody (ab131260, ABCAM) and a mouse anti-FLAG antibody (F1804, SIGMA). Fluorescence detected via confocal microscopy at 546 nm indicated FLAG-tagged peptide and NE co-localization.

Example 31—Assaying Bacterial Killing

Figure 18D:
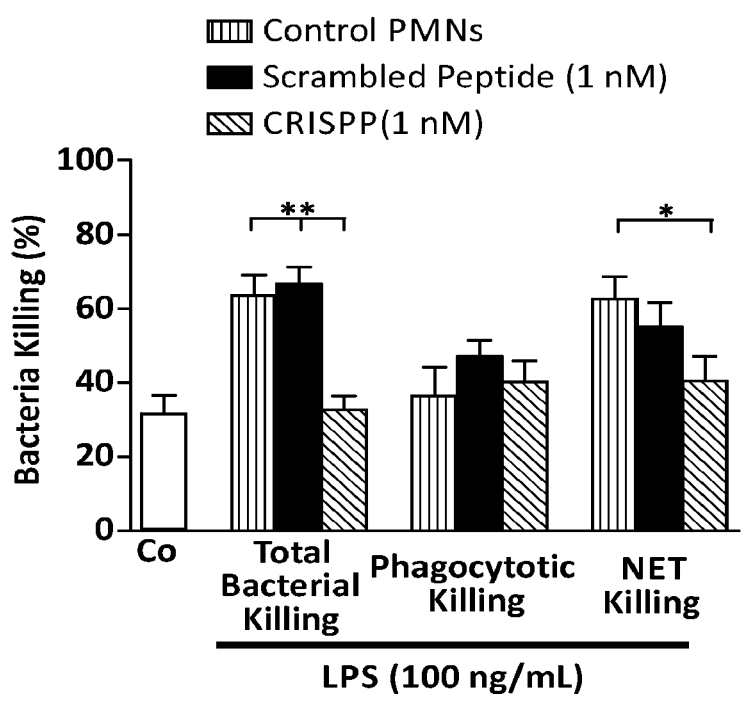
FIG. 18D is a graph depicting total, phagocytic, and extracellular NET-mediated bacterial killing by LPS-stimulated human PMNs (100 ng/mL)±pretreatment with CRISPP (1 nM) or SCR (1 nM). * denotes $p<0.05$ and ** denotes $p<0.01$.
Figure 18E:
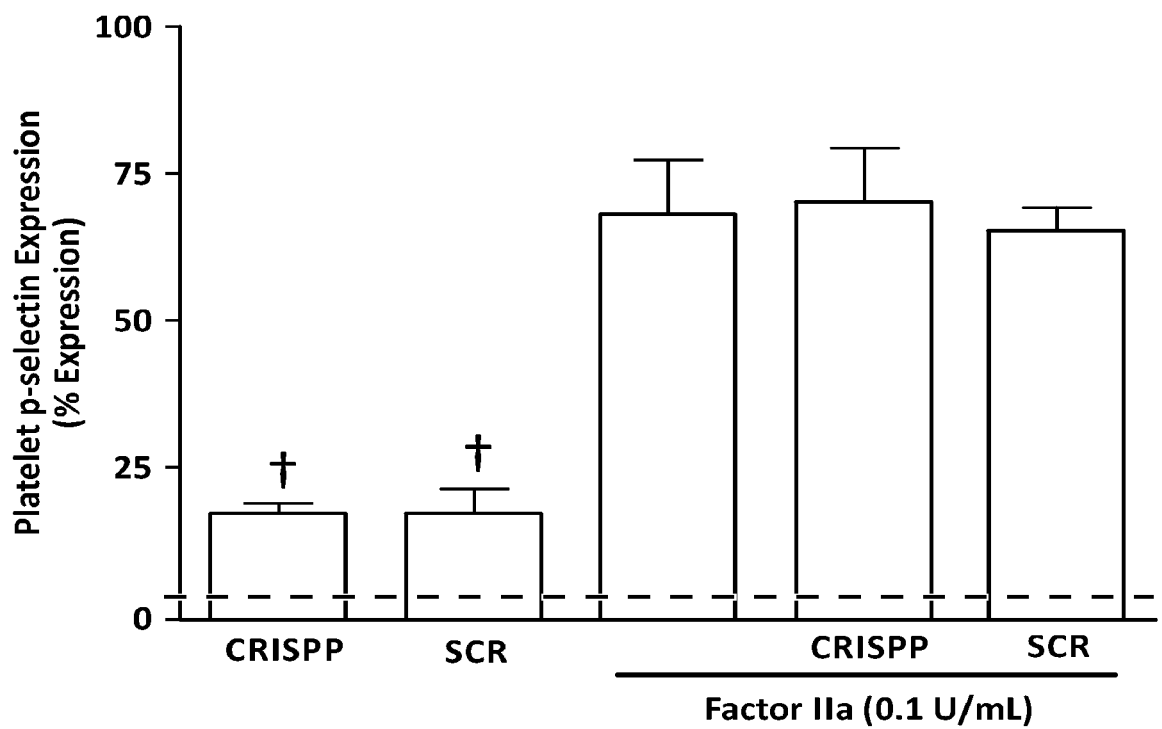
FIG. 18E is a graph depicting platelet p-selectin expression following pre-incubation with CRISPP (1 nM) or SCR (1 nM) prior to thrombin stimulation (0.1 IU/mL), as indicated. The dashed line indicates the level of platelet p-selectin expression at baseline. † denotes $p<0.001$ for CRISPP and SCR groups compared with all three thrombin-stimulated groups and baseline.
Figure 18F:
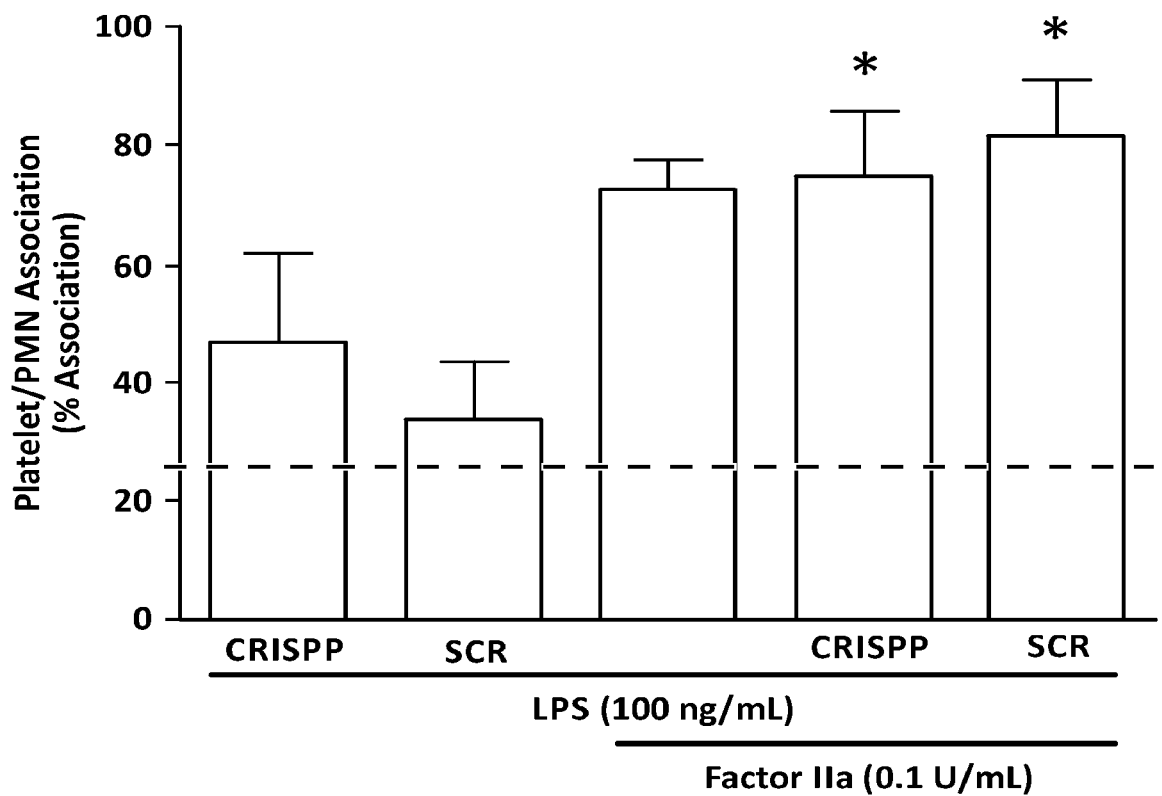
FIG. 18F is a graph depicting LPS-stimulated PMN aggregation with thrombin (0.1 IU/mL) activated platelets±CRISPP (10 nM) or SCR (10 nM) pre-incubation. The dashed line represents the LPS control group. * denotes $p<0.05$ for CRISPP/Factor IIa and SCR/Factor IIa groups compared to baseline.

As discussed above, it was found that while CRISPP pre-incubation of LPS-stimulated PMNs significantly decreased total and NET-mediated extracellular bacterial killing in comparison to control PMNs, the phagocytotic component of bacterial killing was not different between total, phagocytotic, and NET-mediated bacterial killing of a pathogenic strain of E. coli (see FIG. 18D).

Bacterial killing efficiency of primary human PMNs was determined as previously described in Yost et al., Blood, 2009, 113: 6419-6427. PMNs were incubated for 30 minutes at 37° C. in 5% $CO_2$/95% air alone or with the phagocytosis inhibitors cytochalasin B and D (10 µM). The leukocytes were then stimulated with LPS (100 ng/mL), placed in poly-L-lysine-coated wells of a 24-well tissue culture plate, and incubated at 37° C. for 1 hour to induce cellular activation and formation of NETs. To inhibit NET-mediated bacterial killing, we incubated selected wells with DNase (40 U/mL) for 15 minutes prior to addition of bacteria. E. coli (1 cfu/100 PMN) were added to the PMNs, followed by continued incubation for 2 hours. The PMNs were then permeabilized with 0.1% Triton-X 100 for 10 minutes and each well was scraped to free all cells. Serial dilutions were performed and bacterial cultures were grown on 5% sheep blood agar plates (HARDY DIAGNOSTICS). After a 24-hour incubation, bacterial counts were determined. Total, phagocytotic, and fractional NET-mediated bacterial killing were determined as described above.

Example 32—Studying Survival in Murine Models of Sepsis

Animals were treated with CRISPP (10 mg/kg), nNIF (10 mg/kg), or SCR (10 mg/kg) by i.p. injection 1 hour prior to and 6 hours after infection (E. coli, $4.5 \times 10^7$ cfu/mouse, i.p. injection) or stimulation (LPS, 25 mg/kg, i.p. injection). Other mice were subjected to CL/P as a model of polymicrobial sepsis (see Araujo et al., Microvasc Res, 2012, 84: 218-221). Still other mice were injected with nNIF, CRISPP, or SCR 4 hours after injection/stimulation to evaluate post-infection impact of nNIF/CRISPP on survival. Control mice were injected with saline alone and control mice for the CL/P mice were subjected to sham surgery. The mice in these studies were not treated with fluid resuscitation or antibiotic treatment, but were provided with ample food and water during the experiments. Survival was assessed over 6 days at 6 hour to 12 hour intervals.

Example 33—Performing Statistical Analysis

GRAPHPAD PRISM statistical software (version 4, GRAPHPAD SOFTWARE) was used to analyze results. Reported values are the mean±SEM. To assess differences between more than two sets of normally distributed data the one-way ANOVA test with Tukey's or Bonferroni's post-hoc testing was employed. For comparison of two groups of continuously distributed data, the unpaired, single or two tailed Student's t-test was used where appropriate. For comparison of murine survival curves, the Log-rank (Mantel-Cox) test was used. All P values of less than 0.05 were considered statistically significant.

It will be apparent to those having skill in the art that many changes may be made to the details of the above-described embodiments without departing from the underlying principles of the invention. The scope of the present invention should, therefore, be determined only by the following claims.

The invention claimed is:

1. A pharmaceutical composition, comprising:
    a peptide consisting of the amino acid sequence of SEQ ID NO:4, wherein the amino acid sequence comprises at least one amino acid substitution or a pharmaceutically acceptable salt thereof, and a pharmaceutically acceptable carrier.

2. The pharmaceutical composition of claim 1, wherein the amino acid substitution is a nonconservative substitution.

3. The pharmaceutical composition of claim 1, wherein the peptide is in an amount effective to substantially inhibit damage from inflammatory tissue injury.

4. The pharmaceutical composition of claim 1, wherein the peptide does not substantially inhibit on more activities of a polymorphonuclear leukocyte (PMN) selected from the group consisting of chemotaxis, chemokine synthesis and secretion, cytokine synthesis and secretion, extracellular bacterial killing, intracellular bacterial killing, phagocytosis, and reactive oxygen species (ROS) generation.

5. The pharmaceutical composition of claim 1, wherein the peptide is present in an amount effective to treat a patient having an inflammatory disorder selected from the group consisting of: acute respiratory distress syndrome (ARDS), bronchopulmonary dysplasia (BPD), chronic obstructive pulmonary disease (COPD), cystic fibrosis, inflammation in cancer, inflammatory bowel disease (IBD), inflammatory lung disease (ILD), influenza-induced pneumonitis, necrotizing enterocolitis (NEC), neonatal chronic lung disease (CLD), periodontitis, pre-eclampsia, retinopathy of prematurity (ROP), sepsis, systemic inflammatory response syndrome (SIRS), thrombosis, transfusion-related acute lung injury (TRALI), vasculitis, rheumatoid arthritis (RA), systemic lupus erythematosus (SLE), and Wegener's granulomatosis (WG).

6. The pharmaceutical composition of claim 1, wherein the peptide is present in an amount effective to substantially inhibit NETosis or neutrophil extracellular trap (NET) formation.

7. The pharmaceutical composition of claim 6, wherein the NETosis or NET formation is stimulated by at least one of a bacterium, a fungus, a parasite, or a virus.

8. The pharmaceutical composition of claim 7, wherein the virus is selected from the group consisting of hemorrhagic fever virus, filovirus, Ebola virus, Marburg virus, arena virus, Lassa virus, hantavirus, flavivirus, dengue virus, yellow fever virus, or HIV-1.

9. The pharmaceutical composition of claim 7, wherein the NETosis or NET formation is stimulated by at least one of the group selected from a *Bacillus* species, an *Escherichia* species, a *Francisella* species, a *Staphylococcus* species, a *Streptococcus* species, or a *Yersinia* species.

10. A method for treating neutrophil extracellular trap (NET) mediated inflammatory tissue damage in a patient, comprising:
administering to the patient an effective amount of a pharmaceutical composition comprising a peptide consisting of the amino acid sequence of SEQ ID NO:4, wherein the amino acid sequence comprises at least one amino acid substitution or a pharmaceutically acceptable salt thereof,
and a pharmaceutically acceptable carrier.

11. The method of claim 10, wherein the pharmaceutical composition substantially inhibits NET-mediated inflammatory damage.

12. The method of claim 10, wherein the peptide does not substantially inhibit one or more activities of a polymorphonuclear leukocyte (PMN) selected from the group consisting of chemotaxis, chemokine synthesis and secretion, cytokine synthesis and secretion, extracellular bacterial killing, intracellular bacterial killing, phagocytosis, and reactive oxygen species (ROS) generation.

13. The method of claim 10, wherein the peptide is present in an amount effective to treat a patient having an inflammatory disorder selected from the group consisting of: acute respiratory distress syndrome (ARDS), bronchopulmonary dysplasia (BPD), chronic obstructive pulmonary disease (COPD), cystic fibrosis, inflammation in cancer, inflammatory bowel disease (IBD), inflammatory lung disease (ILD), influenza-induced pneumonitis, necrotizing enterocolitis (NEC), neonatal chronic lung disease (CLD), periodontitis, pre-eclampsia, retinopathy of prematurity (ROP), sepsis, systemic inflammatory response syndrome (SIRS), thrombosis, transfusion-related acute lung injury (TRALI), vasculitis, rheumatoid arthritis (RA), systemic lupus erythematosus (SLE), and Wegener's granulomatosis (WG).

14. The method of claim 10, wherein the peptide is present in an amount effective to substantially inhibit NETosis or neutrophil extracellular trap (NET) formation.

15. The method of claim 14, wherein the NETosis or NET formation is stimulated by at least one of a bacterium, a fungus, a parasite, or a virus.

16. The method of claim 15, wherein the NETosis or NET formation is stimulated by a virus selected from at least one of a hemorrhagic fever virus, a Filovirus, an arenavirus, a hantavirus, a flavivirus, dengue virus, yellow fever virus or HIV-1.

17. The method of claim 15, wherein the NETosis or NET formation is stimulated by a bacterium selected from at least one of a *Bacillus* species, and *Escherichia* species, a *Francisella* species, a *Staphylococcus* species, a *Streptococcus* species, or a *Yersinia* species.

18. The method of claim 10, wherein the pharmaceutical formulation is for oral, subcutaneous, intramuscular, or intravenous administration, or administration by inhalation.

19. The method of claim 10, wherein the patient is human.

20. A pharmaceutical kit, comprising:
a sterile-filled vial or ampoule comprising the pharmaceutical composition according to claim 1 for injection in an amount effective to inhibit NETosis or neutrophil extracellular trap (NET) formation.

21. The pharmaceutical composition of claim 1, wherein the substitution is an incorporation of one or more amino acids with a blocking group.

\* \* \* \* \*

SEQUENCE LISTING

```
<160> NUMBER OF SEQ ID NOS: 5

<210> SEQ ID NO 1
<211> LENGTH: 60
<212> TYPE: PRT
<213> ORGANISM: Homo sapiens

<400> SEQUENCE: 1

Lys Ala Val Leu Thr Ile Asp Glu Lys Gly Thr Glu Ala Ala Gly Ala
1               5                   10                  15

Met Phe Leu Glu Ala Ile Pro Met Ser Ile Pro Pro Glu Val Lys Phe
            20                  25                  30
```

```
Asn Lys Pro Phe Val Phe Leu Met Ile Glu Gln Asn Thr Lys Ser Pro
         35                  40                  45

Leu Phe Met Gly Lys Val Val Asn Pro Thr Gln Lys
 50                  55                  60

<210> SEQ ID NO 2
<211> LENGTH: 30
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 2

Met Xaa Ile Pro Pro Glu Val Lys Phe Asn Lys Pro Phe Val Phe Leu
 1               5                  10                  15

Met Ile Asp Gln Asn Thr Lys Val Pro Leu Phe Met Gly Lys
             20                  25                  30

<210> SEQ ID NO 3
<211> LENGTH: 38
<212> TYPE: PRT
<213> ORGANISM: homo sapiens

<400> SEQUENCE: 3

Pro Met Ser Ile Pro Pro Glu Val Lys Phe Asn Lys Pro Phe Val Phe
 1               5                  10                  15

Leu Met Ile Glu Gln Asn Thr Lys Ser Pro Leu Phe Met Gly Lys Val
             20                  25                  30

Val Asn Pro Thr Gln Lys
         35

<210> SEQ ID NO 4
<211> LENGTH: 29
<212> TYPE: PRT
<213> ORGANISM: homo sapiens

<400> SEQUENCE: 4

Lys Phe Asn Lys Pro Phe Val Phe Leu Met Ile Glu Gln Asn Thr Lys
 1               5                  10                  15

Ser Pro Leu Phe Met Gly Lys Val Val Asn Pro Thr Gln
             20                  25

<210> SEQ ID NO 5
<211> LENGTH: 28
<212> TYPE: PRT
<213> ORGANISM: homo sapiens

<400> SEQUENCE: 5

Ile Pro Pro Glu Val Lys Phe Asn Lys Pro Phe Val Phe Leu Met Ile
 1               5                  10                  15

Asp Gln Asn Thr Lys Val Pro Leu Phe Met Gly Lys
             20                  25
```